United States Patent
Roberts et al.

(10) Patent No.: US 11,366,100 B2
(45) Date of Patent: Jun. 21, 2022

(54) P13K-MTORC1-S6K1 SIGNALING PATHWAY BIOMARKERS PREDICTIVE OF ANTI-CANCER RESPONSES

(71) Applicants: Dana-Farber Cancer Institute, Inc., Boston, MA (US); President and Fellows of Harvard College, Cambridge, MA (US)

(72) Inventors: Thomas M. Roberts, Cambridge, MA (US); Haoxuan Tong, Cambridge, MA (US); Jean Zhao, Brookline, MA (US); John Blenis, New York, NY (US)

(73) Assignees: Dana-Farber Cancer Institute, Inc., Boston, MA (US); President and Fellows of Harvard College, Cambridge, MA (US)

( * ) Notice: Subject to any disclaimer, the term of this patent is extended or adjusted under 35 U.S.C. 154(b) by 93 days.

(21) Appl. No.: 15/116,319

(22) PCT Filed: Feb. 12, 2015

(86) PCT No.: PCT/US2015/015544
§ 371 (c)(1),
(2) Date: Aug. 3, 2016

(87) PCT Pub. No.: WO2015/123377
PCT Pub. Date: Aug. 20, 2015

(65) Prior Publication Data
US 2017/0184565 A1    Jun. 29, 2017

Related U.S. Application Data

(60) Provisional application No. 61/938,816, filed on Feb. 12, 2014.

(51) Int. Cl.
| | | |
|---|---|---|
| *G01N 33/50* | (2006.01) | |
| *A61K 31/58* | (2006.01) | |
| *A61K 45/06* | (2006.01) | |
| *C12Q 1/6886* | (2018.01) | |
| *G01N 33/574* | (2006.01) | |

(52) U.S. Cl.
CPC .......... *G01N 33/5011* (2013.01); *A61K 31/58* (2013.01); *A61K 45/06* (2013.01); *C12Q 1/6886* (2013.01); *G01N 33/5088* (2013.01); *G01N 33/57492* (2013.01); *C12Q 2600/106* (2013.01); *C12Q 2600/118* (2013.01); *C12Q 2600/136* (2013.01); *C12Q 2600/156* (2013.01); *C12Q 2600/158* (2013.01); *G01N 2333/91215* (2013.01); *G01N 2500/10* (2013.01)

(58) Field of Classification Search
None
See application file for complete search history.

(56) References Cited

U.S. PATENT DOCUMENTS

| | | | | |
|---|---|---|---|---|
| 8,008,246 B2* | 8/2011 | Breffa | ............ | A61K 8/4973 |
| | | | | 510/474 |
| 8,008,346 B2* | 8/2011 | Pelletier | ............ | A61K 31/055 |
| | | | | 435/375 |
| 2006/0275262 A1 | 12/2006 | Mathis et al. | | |
| 2009/0186839 A1* | 7/2009 | Lowe | ............ | A01K 67/0271 |
| | | | | 514/34 |
| 2015/0087598 A1* | 3/2015 | Kufe | ............ | A61K 31/357 |
| | | | | 514/19.3 |
| 2015/0219624 A1* | 8/2015 | Wendel | ............ | A61K 31/357 |
| | | | | 514/173 |
| 2017/0304261 A1* | 10/2017 | Baiocchi | ............ | A61K 39/0011 |

FOREIGN PATENT DOCUMENTS

| | | |
|---|---|---|
| WO | WO-2006/122053 A2 | 11/2006 |
| WO | WO-2012/130720 A2 | 10/2012 |
| WO | WO-2012/131594 A1 | 10/2012 |
| WO | WO-2013/166150 A1 | 11/2013 |

OTHER PUBLICATIONS

De Sousa E Melo et al. EMBO reports (2013) 14, 686-695 (Year: 2013).*
Ruggero et al. Nature Medicine (2004) 10, 484-486 (Year: 2004).*
Gutierrez et al. "High frequency of PTEN, PI3K, and AKT abnormalities in T-cell acute lymphoblastic leukemia," Blood, Jul. 16, 2009, 114, 3, 647-650; (Year: 2009).*
Guo et al. "Multi-genetic events collaboratively contribute to Pten-null leukaemia stem-cell formation," Nature, May 22, 2008, 453, 529-532. (Year: 2008).*
Extended European Search Report issued by the European Patent Office in corresponding Application No. 15749226.5, dated Sep. 28, 2017.
Guo et al., "Multi-genetic events collaboratively contribute to Pten-null leukaemia stem-cell formation," Nature, 453(7194):529-533 (2008).
Lin et al., "c-Myc and eIF4F constitute a feedforward loop that regulates cell growth: implications for anticancer therapy," Cancer Res, 69(19):7491-7494 (2009).
Finver et al., "Sequence analysis of the MYC oncogene involved in the t(8;14)(q24;q11) chromosome translocation in a human leukemia T-cell line indicates that putative regulatory regions are not altered," Proc. Natl. Acad. Sci. USA 85:3052-3056 (1988).
GenBank NM_001416.3 submitted by Qi et al., "Over-expression of human cytomegalovirus miR-US25-2-3p downregulates eIF4A1 and inhibits HCMB replication," FEBS Lett. 587:2266-2271 (2013) (Oct. 16, 2005).

(Continued)

Primary Examiner — Jeffrey S Lundgren
Assistant Examiner — Michael J Schmitt
(74) Attorney, Agent, or Firm — Foley Hoag LLP

(57) ABSTRACT

The present invention is based, in part, on the identification of novel FI.3K-mTORCI-S6K 1 signaling pathway biomarkers predictive of responsiveness to anti-cancer therapies.

4 Claims, 18 Drawing Sheets

Specification includes a Sequence Listing.

(56) References Cited

OTHER PUBLICATIONS

GenBank J03253.1 submitted by Finver et al., "Sequence analysis of the MYC oncogene involved in the t(8;14)(q24;q11) chromosome translocation in a human leukemia T-cell line indicates that putative regulatory regions are not altered," Proc. Natl. Acad. Sci. USA 85:3052-3056 (1988) (Jan. 7, 1995).

Hannan et al., "Signaling to the Ribosome in Cancer—It Is More Than Just mTORC1," IUBMB Life, 63(2):79-85 (2011).

Ilic et al., "P13K-targeted therapy can be evaded by gene amplification along the MYC-eukaryotic translation initiation factor 4E (eIF4E) axis," PNAS, 108(37):E699-E708 (2011).

International Search Report dated Jul. 16, 2015 from PCT/US15/15544.

Liu et al., "Oncogenic PIK3CA-driven mammary tumors frequently recur via P13K pathway-dependent and -independent mechanisms," Nat. Med. 17:1116-1120 (2011).

Qi et al., "Over-expression of human cytomegalovirus miR-US25-2-3p downregulates eIF4A1 and inhibits HCMV replication," FEBS Lett. 587:2266-2271 (2013).

Wolfe et al., "RNA G-quadruplexes cause eIF4A-dependent oncogene translation in cancer," Nature 513:65-70 (2014).

* cited by examiner

A

B

C

D

A

B

C

D

E

F

PI3K-MTORC1-S6K1 SIGNALING PATHWAY BIOMARKERS PREDICTIVE OF ANTI-CANCER RESPONSES

RELATED APPLICATIONS

The present application is the U.S. National Stage Application of International Application No. PCT/US2015/15544, filed on Feb. 12, 2015, which claims the benefit of priority to U.S. Provisional Application No. 61/938,816, filed on 12 Feb. 2014; the entire contents of each of said applications is incorporated herein in its entirety by this reference.

GOVERNMENT FUNDING

This invention was made with government support under grant numbers CA030002, CA050661, and CA172461 awarded by The National Institutes of Health and W81XWH-12-1-0078 awarded by The Department of The Army. The government has certain rights in the invention.

BACKGROUND OF THE INVENTION c-Myc is a basic-helix-loop-helix leucine zipper (bHLH-LZ) transcription factor that functions as a master regulator of the transcriptome, thus governing many cellular processes, including cell proliferation and transformation (Lin et al. (2012) *Cell* 151:56-67 and Nie et al. (2012) *Cell* 151:68-79). A wide spectrum of genomic and genetic alterations of MYC have been found in various tumors, including gene translocations, amplification, overexpression and occasional point mutations (Beroukhim et al. (2010) *Nature* 463:899-905; Eilers and Eisenman (2008) *Genes Dev.* 22:2755-2766; Meyer and Penn (2008) *Nat. Rev. Cancer* 8:976-990; Pomerantz et al. (2009) *Nat. Genet.* 41:882-884; Setoodeh et. al. (2013) *Int. J. Clin. Exp. Pathol.* 6:155-167; and Wright et al. (2010) *Mol. Cell Biol.* 30:1411-1420). In addition, increased abundance of the c-MYC protein is also frequently observed in cancer via distinct mechanisms such as alterations in upstream regulators or posttranslational modifications (Choi et al. (2010) *Genes Dev.* 24:1236-1241; Huang et al. (2004) *Mol. Cell Biol.* 24:1582-1594; Malempati et al. (2006) *Leukemia* 20:1572-1581; and Wiegering et al. (2013) *PLoS One* 8:e75292). The upregulation of c-MYC occurs in a majority of human malignancies, and is usually associated with poor prognosis (Miyawaki et al. (2012) *Cancer Sci.* 103:1558-1566; Pedersen et al. (2013) *Eur. J. Haematol.* 92:42-48; and Ryan et al. (2012) *Acta Neuropathol.* 123:501-513). Therefore, c-MYC represents a major target for cancer therapy.

Despite decades of enormous effort to develop therapeutics to inhibit its function, direct targeting c-MYC via pharmacological agents has remained challenging, in part due to the fact that the c-MYC protein lacks a conventional druggable pocket (Darnell (2002) *Nat. Rev. Cancer* 2:740-749). Although it is known that the oncogenic activity of c-MYC requires dimerization with its binding partner MAX (Amati et al. (1993) *Cell* 72:233-245 and Blackwood and Blackwood and Eisenman (1991) *Science* 251:1211-1217), efforts trying to inhibit such protein-protein interaction have also been unsuccessful (Nair and Burley (2003) *Cell* 112: 193-205). Recent studies demonstrated the existence of synthetic lethal interactions between c-MYC activation and certain elements in a number of cellular pathways, such as protein sumorylation (Kessler et al. (2012) *Science* 335:348-353), cell division (Horiuchi et al. (2012) *J. Exp. Med.* 209:679-696 and Yang et al. (2010) *Proc. Natl. Acad. Sci. U.S.A.* 107:13836-13841), and initiation of protein translation (Lin et al. (2012) *Cell Rep.* 1:325-333). In addition, pharmaceutically targeting BET bromodomain proteins has been shown to effectively suppress MYC transcription, and consequently, the growth of some classes of c-MYC dependent tumors (Bandukwala et al. (2012) *Proc. Natl. Acad. Sci. U.S.A.* 109:14532-14537; Cheng et al. (2013) *Clin. Cancer Res.* 19:1748-1759; Da Costa et al. (2013) *Blood Cancer J.* 3:e126; Delmore et al. (2011) *Cell* 146:904-917; Filippakopoulos et al. (2010) *Nature* 468:1067-1073; Henssen et al. (2013) *Oncotarget* 4:2045-2056; Lockwood et al. (2012) *Proc. Natl. Acad. Sci. U.S.A.* 109:19408-19413; Mertz et al. (2011) *Proc. Natl. Acad. Sci. U.S.A.* 108:16669-16674; Ott et al. (2012) *Blood* 120:2843-2852; Shimamura et al. (2013) *Clin. Cancer Res.* 19:6183-6192; Tolani et al. (2013) *Oncogene* epub 24 Jun. 2013; and Zuber et al. (2011) *Nature* 478:524-528). These findings have underscored the potential of indirectly targeting c-MYC through intervening in the molecular mechanisms that regulate c-MYC.

Based on the inability to directly target c-MYC in c-MYC-dependent cancers, there is a great need in the art to identify indirect targets to regulate c-MYC in such cancers, as well as a need in the art to identify biomarkers which are predictive of patient responsiveness to inhibitors of the PI3K-mTORC1-S6K1 signaling pathway in order to appropriately determine an efficacious and cost-effective course of therapeutic intervention.

SUMMARY OF THE INVENTION

The present invention is based, at least in part, on the discovery that the amount of cy-MYC protein is highly dependent on hyper-activation of the PI3K-mTORC1-S6K1 signaling pathway such that the signaling pathway regulates a 5' untranslated (5' UTR)-dependent, eIF4A- and eIF4B-mediated mechanism that governs the translation of c-MYC in c-MYC-dependent cancers. S6K1 regulates c-MYC 5'UTR through the translation initiation factor eIF4A, an RNA helicase critical of unwinding the structured 5'UTR of c-MYC for its translation initiation. Thus, the presence, absence, amount (e.g., copy number or level of expression), and/or activity of the c-MYC 5' UTR or portion thereof is a biomarker for predicting the response of c-MYC-dependent cancers to inhibitors of the PI3K-mTORC1-S6K1 signaling pathway. In addition, eIF4A and eiF4B, as well as inhibitors thereof, are useful in the diagnosis, prognosis, and treatment of c-MYC-dependent cancers. These results contrast with previous findings that c-MYC overexpression renders cells resistant to PI3K/mTOR inhibition (Clegg et al. (2011) *PLoS One* 6:e17449; Ilic et al. (2011) *Proc. Natl. Acad. Sci. U.S.A.* 108:E699-E708; and Liu et al. (2011) *Nat. Med.* 17:1116-1120).

In one aspect, a method of identifying the likelihood of a cellular avian myelocytomatosis viral oncogene homolog (c-MYC)-dependent cancer in a subject to be responsive to phosphoinositide 3-kinase (PI3K)-mammalian target of rapamycin complex 1 (mTORC1)-ribosomal S6 kinase 1 (S6K1) signaling pathway inhibitor therapy, the method comprising: a) obtaining or providing a sample from a patient having a c-MYC-dependent cancer; b) measuring the presence, absence, amount, or activity of at least one biomarker listed in Table 1 in the subject sample; and c) comparing said presence, absence, amount, or activity of the at least one biomarker listed in Table 1 in a control sample, wherein the presence of the at least one biomarker listed in Table 1 or a significantly increased amount or activity of the at least one biomarker listed in Table 1 in the subject sample relative to the control sample identifies the c-MYC-dependent cancer as being more likely to be responsive to PI3K-mTORC1-S6K1 signaling pathway inhibitor therapy, and wherein the absence of the at least one biomarker or a significantly decreased amount or activity of the at least one biomarker listed in Table 1 in the subject sample relative to the control sample identifies the c-MYC-dependent cancer as being less likely to be responsive to PI3K-mTORC1-S6K1 signaling pathway inhibitor therapy is provided.

In another aspect, a method of identifying the likelihood of a cellular c-MYC-dependent cancer in a subject to be responsive to PI3K-mTORC1-S6K1 signaling pathway inhibitor therapy, the method comprising: a) obtaining or providing a sample from a patient having a c-MYC-dependent cancer, wherein the sample comprises nucleic acid molecules from the subject; b) determining the copy number of at least one biomarker listed in Table 1 in the sample; and c) comparing said copy number to that of a control sample, wherein an increased copy number of the biomarker in the sample relative to the control sample identifies the c-MYC-dependent cancer as being more likely to be responsive to the PI3K-mTORC1-S6K1 signaling pathway inhibitor therapy and wherein a decreased copy number of the biomarker in the sample relative to the control sample identifies the c-MYC-dependent cancer as being less likely to be responsive to the PI3K-mTORC1-S6K1 signaling pathway inhibitor therapy is provided.

In one embodiment of any aspect of the present invention, the method further comprises recommending, prescribing, or administering PI3K-mTORC1-S6K1 signaling pathway inhibitor therapy if the c-MYC-dependent cancer is determined to be likely to be responsive to PI3K-mTORC1-S6K1 signaling pathway inhibitor therapy. In another embodiment, the method further comprises recommending, prescribing, or administering anti-cancer therapy other than PI3K-mTORC1-S6K1 signaling pathway inhibitor therapy if the c-MYC-dependent cancer is determined be less likely to be responsive to PI3K-mTORC1-S6K1 signaling pathway inhibitor therapy. In still another embodiment, the anti-cancer therapy is selected iron, the group consisting of targeted therapy, chemotherapy, radiation therapy, and/or hormonal therapy. In yet another embodiment, the control sample is determined from a cancerous or non-cancerous sample from either the patient or a member of the same species to which the patient belongs. In another embodiment, the control sample comprises cells or does not comprise cells. In still another embodiment, the control sample comprises cancer cells known to be responsive or non-responsive to the PI3K-mTORC1-S6K1 signaling pathway inhibitor therapy.

In still another aspect, a method of assessing the efficacy of an agent for treating a c-MYC-dependent cancer in a subject that is unlikely to be responsive to PI3K-mTORC1S6K1 signaling pathway inhibitor therapy, comprising: a) detecting in a first subject sample and maintained in the presence of the agent the presence, absence, amount, or activity of at least one biomarker listed in Table 1; b) detecting the presence, absence, amount, or activity of the at least one biomarker listed in Table 1 in a second subject sample and maintained in the absence of the test compound; and c) comparing the presence, absence, amount, or activity of the at least one biomarker listed in Table 1 from steps a) and b), wherein an absence or a significantly decreased amount or activity of the at least one biomarker listed in Table 1 in the first subject sample relative to at least one subsequent subject sample, indicates that the agent treats the c-MYC-dependent cancer in the subject is provided.

In yet another aspect, a method of assessing the efficacy of an agent for treating a c-MYC-dependent cancer in a subject that is unlikely to be responsive to PI3K-mTORC1-S6K1 signaling pathway inhibitor therapy, comprising: a) detecting in a subject sample at a first point in time the presence, absence, amount, or activity of at least one biomarker listed in Table 1; b) repeating step a) during at least one subsequent point in time after administration of the agent; and c) comparing the presence, absence, amount, or activity detected in steps a) and b), wherein an absence or a significantly decreased amount or activity of the at least one biomarker listed in Table 1 in the first subject sample relative to at least one subsequent subject sample, indicates that the agent treats the c-MYC-dependent cancer in the subject is provided. In one embodiment, the subject has undergone treatment, completed treatment, and/or is in remission for the cancer between the first point in time and the subsequent point in time. In another embodiment, the first and/or at least one subsequent sample is selected from the group consisting of ex vivo and in vivo samples. In still another embodiment, the first and/or at least one subsequent sample is obtained from an animal model of the cancer. In yet another embodiment, the first and/or at least one subsequent sample is a portion of a single sample or pooled samples obtained from the subject.

In another aspect, a cell-based assay for screening for cytotoxic or cytostatic agents comprising contacting a c-MYC-dependent cancer cell with a test agent, and determining the ability of the test agent to increase the amount or activity of at least one biomarker listed in Table 1 is provided. In one embodiment, the step of contacting occurs in vivo, ex vivo, or in vitro.

In still another aspect, a cell-based assay for screening for agents that have a cytotoxic or cytostatic effect on a c-MYC-dependent cancer cell that is unresponsive to PI3K-mTORC1-S6K1 signaling pathway inhibitor therapy comprising, contacting the c-MYC-dependent cancer cell with a test agent, and determining the ability of the test agent to increase the amount or activity of at least one biomarker listed in Table 1 is provided. In one embodiment, the step of contacting occurs in vivo, ex vivo, or in vitro.

In any aspect of the present invention, certain embodiments are contemplated. For example, in one embodiment of a method or assay described herein, the at least one biomarker listed in Table 1 comprises a c-MYC 5' untranslated region (5' UTR) or a portion thereof. In another embodiment, the at least one biomarker listed in Table 1 comprises an mRNA or cDNA of the c-MYC 5' UTR. In still another embodiment, the subject sample is selected from the group consisting of whole blood, serum, plasma, urine, cells, cell lines, and biopsies. In yet another embodiment, the presence or amount of the at least one biomarker listed in Table 1 is detected using a reagent which specifically binds with the protein (e.g., a reagent selected from the group consisting of an antibody, an antibody derivative, and an antibody fragment). In another embodiment, the presence or amount of the at least one biomarker listed in Table 1 is assessed by detecting the presence in the sample of a transcribed polynucleotide or portion thereof (e.g., an mRNA or a cDNA). In still another embodiment, the step of detecting further comprises amplifying the transcribed polynucleotide. In yet another embodiment, the transcribed polynucleotide is detected by identifying a nucleic acid that anneals with the biomarker nucleic acid, or a portion thereof, under stringent hybridization conditions.

In still another aspect, a method of identifying the likelihood of a c-MYC-dependent cancer in a subject to be responsive to anti-cancer therapy, the method comprising: a) obtaining or providing a sample from a patient having a c-MYC-dependent cancer; b) measuring the amount or activity of at least one biomarker listed in Table 2 in the subject sample; and c) comparing said amount or activity of the at least one biomarker listed in Table 2 in a control sample, wherein a significantly increased amount or activity of the at least one biomarker listed in Table 2 in the subject sample relative to the control sample identifies the c-MYC-dependent cancer as being less likely to be responsive to anti-cancer therapy, and wherein a significantly decreased amount or activity of the at least one biomarker listed in Table 2 in the subject sample relative to the control sample identifies the c-MYC-dependent cancer as being more likely to be responsive to anti-cancer therapy is provided.

In yet another aspect, a method of identifying the likelihood of a cellular c-MYC-dependent cancer in a subject to be responsive to anti-cancer therapy, the method comprising: a) obtaining or providing a sample from a patient having a c-MYC-dependent cancer, wherein the sample comprises nucleic acid molecules from the subject; b) determining the copy number of at least one biomarker listed in Table 2 in the sample; and c) comparing said copy number to that of a control sample, wherein an increased copy number of the biomarker in the sample relative to the control sample identifies the c-MYC-dependent cancer as being less likely to be responsive to the anti-cancer therapy and wherein a decreased copy number of the biomarker in the sample relative to the control sample identifies the c-MYC-dependent cancer as being more likely to be responsive to the anti-cancer therapy is provided.

In one embodiment of any aspect of the present invention, the method further comprises recommending, prescribing, or administering PI3K-mTORC1-S6K1 signaling pathway inhibitor therapy if the c-MYC-dependent cancer is determined to be likely to be responsive to anti cancer therapy. In another embodiment, the method further comprises recommending, prescribing, or administering anti-cancer therapy other than PI3K-mTORC1S6K1 signaling pathway inhibitor therapy if the c-MYC-dependent cancer is determined be less likely to be responsive to anti-career therapy. In still another embodiment, the anti-cancer therapy is selected from the group consisting of targeted therapy, chemotherapy, radiation therapy, and/or hormonal therapy. In yet another embodiment, the control sample is determined from a cancerous or non-cancerous sample from either the patient or a member of the same species to which the patient belongs. In another embodiment, the control sample comprises cells or does not comprise cells. In still another embodiment, the control sample comprises cancer cells known to be responsive or non-responsive to the PI3K-mTORC1-S6K1 signaling pathway inhibitor therapy.

In another aspect, a method of assessing the efficacy of an agent for treating a c-MYC-dependent cancer in a subject, comprising: a) detecting in a first subject sample and maintained in the presence of the agent the amount or activity of at least one biomarker listed in Table 2; b) detecting the amount or activity of the at least one biomarker listed in Table 2 in a second subject sample and maintained in the absence of the test compound; and c) comparing the amount or activity of the at least one biomarker listed in Table 2 from steps a) and b), wherein a significantly increased amount or activity of the at least one biomarker listed in Table 2 in the first subject sample relative to at least one subsequent subject sample, indicates that the agent treats the c-MYC-dependent cancer in the subject is provided.

In still another aspect, a method of assessing the efficacy of an agent for treating a c-MYC-dependent cancer in a subject, comprising: a) detecting in a subject sample at a first point in time the amount or activity of at least one biomarker listed m Table 2; b) repeating step a) during at least one subsequent point in time after administration of the agent and c comparing the amount or activity detected in steps a) and b), wherein a significantly increased amount or activity of the at least one biomarker listed in Table 2 in the first subject sample relative to at least one subsequent subject sample, indicates that the agent treats the c-MYC-dependent cancer in the subject is provided. In one embodiment, the subject has undergone treatment, completed treatment, and/or is in remission for the cancer between the first point in time and the subsequent point in time. In another embodiment, the first and/or at least one subsequent sample is selected from the group consisting of ex vivo and in vivo samples. In still another embodiment, the first and/or at least one subsequent sample is obtained from an animal model of the cancer. In yet another embodiment, the first and/or at least one subsequent sample is a portion of a single sample or pooled samples obtained from the subject.

In yet another aspect, a cell-based assay for screening for cytotoxic of cytostatic agents comprising contacting a c-MYC-dependent cancer cell with a test agent, and determining the ability of the test agent to increase the amount or activity of at least one biomarker listed in Table 2. In one embodiment, the step of contacting occurs in vivo, ex vivo of in vitro.

In another aspect, a cell-based assay for screening for agents that have a cytotoxic or cytostatic effect on a c-MYC-dependent cancer cell comprising, contacting the c-MYC-dependent cancer cell with a test agent, and determining the ability of the test agent to decrease the amount or activity of at least one biomarker listed in Table 2. In one embodiment, the step of contacting occurs in vivo, ex vivo, or in vitro.

In any aspect of the present invention, certain embodiments are contemplated. For example, in one embodiment of any method or assay, wherein the at least one biomarker listed in Table 2 is a human eukaryotic initiation factor-4A (eIF4A) or an ortholog thereof. In another embodiment, the at least one biomarker listed in Table 2 is a human eukaryotic initiation factor-4B (eIF4B) or an ortholog thereof. In still another embodiment, the subject sample is selected from the group consisting of whole blood, serum, plasma, urine, cells, cell lines, and biopsies. In yet another embodiment, the presence or amount of the at least one biomarker listed in Table 2 is detected using a reagent which specifically binds with the protein (e.g., a reagent selected from the group consisting of an antibody, an antibody derivative, and an antibody fragment). In another embodiment, the presence or amount of the at least one biomarker listed in Table 2 is assessed by detecting the presence in the sample of a transcribed polynucleotide or portion thereof (e.g., an mRNA or a cDNA). In still another embodiment, the step of detecting further comprises amplifying the transcribed polynucleotide. In yet another embodiment, the transcribed polynucleotide is detected by identifying a nucleic acid that anneals with the biomarker nucleic acid, or a portion thereof, under stringent hybridization conditions.

In still another aspect, a method of treating a subject afflicted with a c-Myc-dependent cancer comprising administering to the subject an agent that inhibits at least one biomarker listed in Table 2, thereby treating the subject afflicted with the c-Myc-dependent cancer is provided. In one embodiment, the agent is administered in a pharmaceutically acceptable formulation. In another embodiment, the agent directly binds the at least one biomarker listed in Table 2. In still another embodiment, the at least one biomarker listed in Table 2 is selected from the group consisting of human eukaryotic initiation factor-4A (eIF4A) or an ortholog thereof, and human eukaryotic initiation factor-4B (eIF4B) or an ortholog thereof. In yet another embodiment, the method further comprises administering one or more additional anti-cancer agents.

In any aspect of the present invention described above, certain embodiments are contemplated. For example, in one embodiment of any method or assay, the agent or PI3K-mTORC1-S6K1 signaling pathway inhibitor therapy is selected from the group consisting of inhibitors of PI3K, PDK1, mTORC1, S6K1, protein kinase B (PKB also known as AKT), eIF4A, eIF4B, and combinations thereof. In another embodiment, the agent or PI3K-mTORC1-S6K1 signaling pathway inhibitor therapy is selected from the group consisting of an antibody or at fragment thereof, small molecule, nucleic acid, polypeptide, antisense nucleic acid molecules, RNA interference molecules, and combinations thereof. In still another embodiment, responsiveness to anti-cancer therapy or PI3K-mTORC1-S6K1 signaling pathway inhibitor therapy is measured by at least one criteria selected from the group consisting of clinical benefit rate survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria. In yet another embodiment, the c-Myc-dependent cancer is any cancer in which c-Myc is amplified or overexpressed compared to the normal cell type from which the cancer. In another embodiment, the c-Myc-dependent cancer is a solid tumor or a hematological cancer. In still another embodiment, the cancer is selected from the group consisting of T-cell lymphoma, T-cell leukemia, B-cell lymphoma, B-cell leukemia, multiple myeloma, Burkitt lymphoma, myeloid leukemia, breast cancer, and tumors overexpressing c-MYC translated from a cMYC mRNA having a highly structured 5' UTR. In yet another embodiment, the subject is a mammal, such as an animal model of cancer (e.g., Lck$^{Cre+}$/Pten$^{flox/flox}$ animals), or a human.

Figure 1:
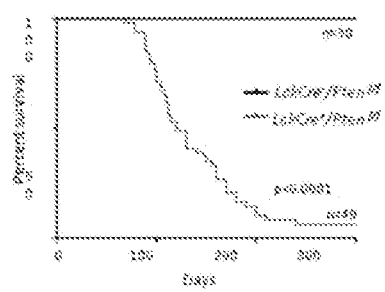
FIG. 1 includes 4 panels, identified as panels (A), (B), (C), and (D), which show that LckCre+/Pten$^{f/f}$ mice develop T-ALL. Panel A shows a Kaplan-Meier survival curve for LckCre$^+$/Pten$^{f/f}$ mice (n=49, median survival 120 days), and LckCre$^-$/Pten$^{f/f}$ control mice (n=30; 100% survival). Panel B shows the tissue weights of thymus, spleen, liver and lymph nodes of LckCre$^+$/Pten$^{f/f}$ moribund mice (right) is significantly higher than that of age matched LckCre$^-$/Pten$^{f/f}$ control nice (left). Panel C shows representative H&E-stained primary thymus, lymph nodes, and spleen sections and representative Wright-giemsa stained primary bone marrow cytospin sections and peripheral blood smear sections from LckCre$^+$/Pten$^{f/f}$ moribund mice and age matched LckCre$^-$/Pten$^{f/f}$ control mice. Panel D shows white blood cell counts of peripheral blood from LckCre$^+$/Pten$^{f/f}$ moribund mice (right) is significantly higher than that of age matched LckCre$^-$/Pten$^{f/f}$ control mice (left).
Figure 1:
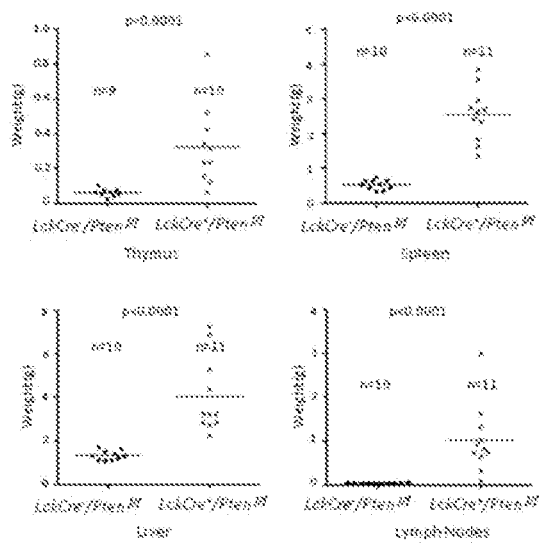
Figure 1:
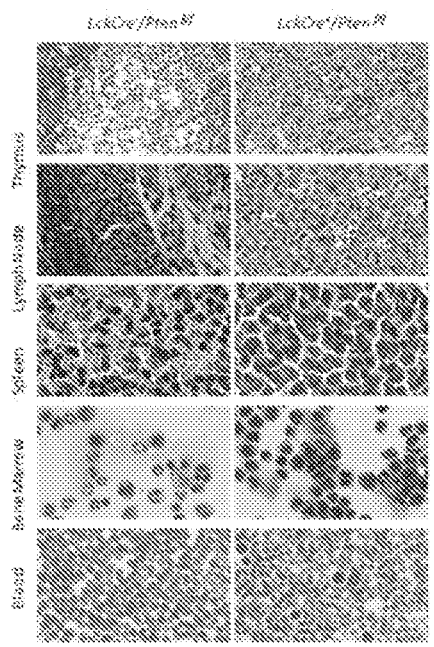
Figure 1:
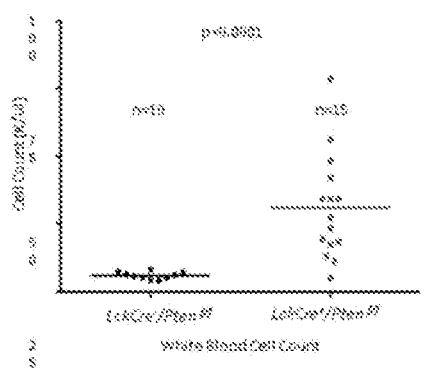

Note that for every figure containing a histogram, the bars from left to right for each discreet measurement correspond to the figure boxes from top to bottom in the figure legend as indicated.

DETAILED DESCRIPTION OF THE INVENTION

The co-occurrence of c-MYC overexpression and PTEN-deficiency is common in c-MYC-dependent cancers, such as T cell acute lymphoblastic leukemia (T-ALL) (Gutierrez et al. (2009) *Blood* 114:647-650). However, the link between the two events remains unclear. Using a genetically engineered murine model of c-MYC-dependent cancer (i.e., T-ALL driven by Pten-loss with spontaneous overexpression of c-Myc) (Guo et al. (2008) *Nature* 453:529-533) and a panel of PTEN-deficient MYC-high human T-ALL cell lines, it was found that the abundance of c-MYC protein in these cells is critically dependent on hyper-activation of PI3K-mTORC1-S6K1 signaling. It was further determined that this signaling pathway robustly regulates the 5'UTR-dependent translation of MYC, which requires eIF4A, a eukaryotic translation initiation factor with an RNA helicase activity. eIF4A inhibition either by RNA interference, or via the pharmacological inhibitor, hippuristanol, was determined to efficiently suppress MYC translation as well as tumor cell proliferation via a mechanism specifically dependent on the 5'UTR of c-MYC. Thus, the presence, absence, amount (e.g., copy number or level of expression), and/or activity of the c-MYC 5' UTR or portion thereof is a biomarker for predicting the response of c-MYC-dependent cancers to inhibitors of the PI3K-mTORC1-86K1 signaling pathway. In addition, eIF4A and eiF4B, as well as inhibitors thereof, are useful in the diagnosis, prognosis, and treatment of c-MYC-dependent cancers.

I. Definitions

The articles "a" and "an" are used herein to refer to one or to more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased, or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternatively, the amount of the biomarker in the subject can be considered "significantly" higher or lower than the normal amount if the amount is at least about two, and preferably at least about three, four, or five times, higher or lower, respectively, than the normal amount of the biomarker.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples.

The term "altered activity" of a biomarker refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody, portion"). The term "antigen binding portion", as used herein, refers to one or more fragments of an antibody that retain the ability to specifically bind to an antigen (e.g., a biomarker polypeptide or fragment thereof). It has been shown that the antigen-binding function of an antibody cart be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al., (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized", which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the predictive score."

The term "biomarker" refers to a measurable entity of the present invention that has been determined to be predictive of anti-cancer therapy (e.g., PI3K-mTORC1-S6K1 signaling pathway inhibitor therapy) effects on a cancer. Biomarkers can include, without limitation, nucleic acids (e.g., genomic nucleic acids and/or transcribed nucleic acids) and proteins, particularly those involved shown in Tables 1 and 2.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluid that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, and vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. In some embodiments, such cells exhibit such characteristics in part or in full due to the expression and activity of oncogenes, such as c-MYC. Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma medullary carcinoma, bronchogenic carcinoma, renal cell carcinoma, hepatoma, bile duct carcinoma, liver cancer, choriocarcinoma seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

The term "c-MYC-dependent cancer" refers to cancer that is functionally dependent on c-MYC. For instance, even if the expression level of c-MYC (e.g., c-MYC mRNA, c-MYC protein, newly synthesized c-MYC protein, etc.) in a tumor tissue is comparable to its expression level in normal tissue, a cancer is c-MYC-dependent if inhibition of the c-MYC mRNA and/or protein, directly or indirectly such as by using RNAi or any other means, or deletion of the c-MYC gene (e.g., by knock-out or clustered regularly interspaced short palindromic repeats (CRISPR) technology) leads to inhibition of oncogenesis, tumor cell proliferation, tumor metastasis or induces tumor cell differentiation. The term "c-MYC-dependent cancer" also refers to a cancer in which c-MYC is expressed (e.g., c-MYC mRNA, c-MYC protein, newly synthesized c-MYC protein, etc.) at a significantly higher level than the normal amount of c-MYC expressed in a non-cancerous cell of the same cell type as the c-MYC-dependent cancer. A significantly higher amount of c. MYC relative to the normal amount of c-MYC is an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or more than the normal amount. Alternately, the amount of the biomarker in the subject can be considered "significantly" higher or lower than the normal amount if the amount is at least about two, and preferably at least about three, four, or five times, higher or lower, respectively, than the normal amount of c-MYC.

The term "coding region" refers to regions of a nucleotide sequence comprising codons which are translated into amino acid residues, whereas the tem "non-coding region" refers to regions of a nucleotide sequence that are not translated into amino acids (e.g., 5' and 3' untranslated regions).

The term "complementary" refers to the broad concept of sequence complementarily between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing, with a residue of a second nucleic acid strand which is antiparallel to the first strand if the residue is guanine. A first region of a nucleic acid is complementary to a second region of the same or a different nucleic acid if when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving, as certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to as percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

The "copy number" of a biomarker nucleic acid refers to the number of DNA sequences in a cell germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, to said one or more genomic loci are not accounted for by the number of copies in germline DNA of a control (e.g., copy number in germline DNA for the same subject as that from which the somatic DNA and corresponding Copy number were determined).

The "normal" copy number (e.g., germline and/or somatic) of a biomarker nucleic acid or "normal" level of expression of a biomarker nucleic acid, or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human not afflicted with cancer, or from a corresponding non-cancerous tissue in the same subject who has cancer.

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is determining whether to provide targeted therapy against a cancer to provide anti-cancer therapy (e.g., PI3K-mTORC1-S6K1 signaling pathway inhibitor therapy). Another example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "expression signature" or "signature" refers to a group of two or more coordinately expressed biomarkers. For example, the genes, proteins, and the like making up this signature may be expressed in a specific cell lineage, stage of differentiation, or during a particular biological response. The biomarkers can reflect biological aspects of the tumors m which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "highly structured 5' untranslated region (5' UTR)" refers to the region of an mRNA directly upstream from the initiation codon, which 1) begins at the transcription start site and and ends one nucleotide (nt) before the initiation codon (usually AUG) of the coding region and 2) contains a hairpin loop or other secondary structures. Such secondary structures are usually predicted by modeling but there are experimental means to define them more quantitatively, such as by measuring the resistance of the structure to nucleases which do not attack double stranded regions or performing physical techniques, such as measuring the optical density at 260 nm as a function of temperature. In one embodiment, the highly structured 5' UTR renders the mRNA a relatively poor substrate for translation. mRNAs encoding proteins necessary for cell growth and survival typically contain a complex, highly structured 5' UTR in order to limit the availability of the protein. Structured 5' UTRs prevent CAP-dependent initiation of translation. Regulation of translation by structured 5' UTRs typically occurs due to long 5' UTRs and stable secondary structures and sequence segments which comprise a high proportion of guanine and cytosine bases since, when present in the 5' UTR of an mRNA, very efficiently inhibit the CAP-dependent initiation of protein biosynthesis according to the ribosome scanning model. In vitro investigations have shown that a hairpin structure in the 5' UTR of an mRNA having a free energy of 30-70 kcal/mol or less is able to inhibit translation effectively. Thus, it has been possible to show that mRNAs coding for a particular protein and having a 5' UTR exhibiting such a structure are translated only very weakly, whereas mRNAs coding for the same protein and having a shorter 5' high with a weaker structure are translated considerably more efficiently. Non-limiting, representative examples of RNAs with a highly structed 5' UTR include c-MYC, X-linked inhibitor of apoptosis protein (XIAP), and ornithine decarboxylase (ODC1).

The term "homologous" refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "inhibit" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a probe or small molecule, for specifically detecting and/or affecting the expression of a marker of the invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic, acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allows patients with large breast cancer to undergo breast-conserving surgery.

The "normal" level of expression of a biomarker is the level of expression of the biomarker in cells of a subject, e.g., a human patient, trot afflicted with a cancer. An "overexpression" or "significantly higher level of expression" of a biomarker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples. Such "significance" levels can also be applied to any other measured parameter described herein, such as for expression, inhibition, cytotoxicity, cell growth, and the like.

The term "PI3K-mTORC1-S6K1 signaling pathway" refers to one of the intracellular signaling pathways activated by the binding of growth factors to receptor tyrosine kinases. On activation, PI3K phosphorylates phosphatidylinositol-4,5-bisphosphate (PIP2) to phosphatidylinositol-3,4,5-triphosphate (PIP3), a process that is reversed by PTEN. PIP3 signals activate the kinase PDK1, which in turn activates the kinase AKT. The AKT protein family, which members are also called protein kinases B (PKB) plays an important role in mammalian cellular signaling. Akt kinase is a serine/threonine kinase which is a downstream effector molecule of phosphoinositide 3-kinase and is involved in protecting a cell from apoptosis. Akt kinase is thought to be involved in the progression of cancer because it stimulates cell proliferation and suppresses apoptosis. Akt1 is involved in cellular survival pathways, by inhibiting apoptotic processes. Akt1 is also able to induce protein synthesis pathways, and is therefore a key signaling protein in the cellular pathways that lead to skeletal muscle hypertrophy, and general tissue growth. Since it can block apoptosis, and thereby promote cell survival, Akt1 has been implicated as a major factor in many types of cancer. Akt is known to play a role in the cell cycle. Under various circumstances, activation of Akt was shown to overcome cell cycle arrest in G1 and G2 phases. Moreover, activated Akt may enable proliferation and survival of cells that have sustained a potentially mutagenic impact and, therefore, may contribute to acquisition of mutations in other genes. AKT (activation amplification) and PTEN (mutation, deletion, epigenetic inactivation) are deregulated in many human cancers (Altomare et al., 2003, J. Cell Biochem. 88:470-476; Ruggeri et al., 1998, Mol. Carcinog. 21:81-86; Cheng et al., 1996, Proc. Natl. Acad. Sci. USA 93:3636-3641; Staal et al., 1987, Proc. Natl. Acad. Sci. USA 84:5034-5037; Li et al., 2005, World J. Gastroenterol. 11:285-288; Li et al., 1997, Science 275:

1943-1947; Goel et al., 2004, 64:3014-3021). PI3K pathway activation can be assessed by immunohistochemical analysis of PTEN or phosphorylated AKT levels in clinical samples (Slipicevic et al., 2005, Am. J. Clin. Pathol. 124:528-536). Molecular targets of such inhibitors include, but are not limited to, PI3K, AKT, S6K1, mTORC1, PDK1, MYC, cMET, FGFR2, growth factors (EGF, b-FGF, IGF1, Insulin, or Heregulin) and the like. For example, mTOR exists in at least 2 distinct multiprotein complexes described as raptor-mTOR complex (mTORC1) and rictor-mTOR complex (mTORC2) in mammalian cells (sometimes referred to as just TORC1 and TORC2). mTORC1 is composed of mTOR, GβL and raptor proteins and it binds to FKBP12-rapamycin, mTORC1 is a rapamycin-sensitive complex as its kinase activity is inhibited by FKB12-rapamycin in vitro and the mTORC1 complex positively regulates cell growth. The raptor branch of the mTOR pathway modulates number of processes, including mRNA translation, ribosome biogenesis, nutrient metabolism and autophagy. The two mammalian proteins, S6 Kinase 1 (S6K1) and 4E-BP1, which are linked to protein synthesis, are downstream targets of mTORC1. mTORC1 has been shown to phosphorylates S6K1 at T389 and is inhibited by FKBP12-rapamycin in vitro and by rapamycin in vivo. mTORC1 can also phosphorylate 4E-BP1 at T37/46 in vitro and in vivo. Other molecular targets are well known in the art and are described, for example, in US 2011-0015869. In some embodiments, the PI3K-mTORC1-S6K1 signaling pathway is limited to subsets of biomolecules within the pathway, such as PI3K, mTORC1, and S6K1, or individual biomolecules within the pathway, such as PI3K.

Exemplary agents useful for inhibiting, PI3K-mTORC1-S6K1 signaling pathway, or other biomarkers described herein, include antibodies, small molecules, peptides, peptidomimetics, natural ligands, and derivatives of natural ligands, that can either bind and/or inactivate or inhibit target proteins, or fragments thereof; as well as RNA interference, antisense, nucleic acid aptamers, etc. that can downregulate the expression and/or activity of target nucleic acids, or fragments thereof. Exemplary inhibitors of the PI3K-mTORC1-S6K1 signaling pathway are also well known in the art and include, but are not limited to: PI3K inhibitors, such as wortmannin (Wymann et al., 1996, Mol. Cell. Biol. 16:1722-1733), LY294002 (Vlahos et al., 1994, J. Biol. Chem. 269:5241-5248; Wetzker and Rommel, 2004, Curr. Pharm. Des. 10:1915-1922) IC87114 (Finan and Thomas, 2004 Biochem. Soc. Trans. 32:378-382; WO0181346); WO01372557; U.S. Pat. No. 6,403,588; WO0143266), BKM120, GDC0941, BEZ235, and many more; mTOR inhibitors, such as RAD001 (also known as Everolimus; Novartis), CCI-779 (also known as Temsirolimus; Pfizer), AP23573 (Ariad Pharmaceuticals), and KU-0059475 (Kudus Pharmaceuticals; Mita, M. M. et al. (2003) Cancer Biology & Therapy 2:4:Suppl.1, S169-S177); S6K1 inhibitors, such as PF-4708671 (Pearce et al., 2010, Biochem. J. 431:245-255) and DG2 (3-bromo-4-)4-)2-methoxyphenyl)piperazine-1-yl)-1H-pyrazolo[3,4-d]-pyrimidine (Axon Medchem); AKT antibodies (Shin et al., 2005, Cancer Res. 65:2815-2824) (see also Cheng et al., Oncogene, 2005, 24:7482-7492 for review on inhibitors of AKT pathway); PDK1 inhibitors, such as AR-12, BX-795, staurosporine, OSU-03012, celecoxib, and others described in U.S. Pat. Nos. 6,124,272; 7,344,870; and 7,041,687); and IGF1R inhibitors (such as monoclonal antibody MK-0646 U.S. Pat. No. 7,241,444).

The term "predictive" includes the use of a biomarker nucleic acid and/or protein status, e.g., over- or under-activity, emergence, expression, growth, remission, recurrence or resistance of tumors before, during or after therapy, for determining the likelihood of response of a cancer to anti-cancer therapy, such as PI3K-mTORC1-S6K1 signaling pathway inhibitor treatment (e.g., PI3K inhibitors). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC) and/or biomarker target, or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g., a human, afflicted with cancer; (3) its absolute or relatively modulated presence or absence in clinical subset of patients with cancer (e.g., those responding to a particular anti-cancer therapy (e.g., PI3K-mTORC1-S6K1 signaling pathway inhibitor therapy) or those developing resistance thereto).

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., solid tumors, such as lung cancer, melanoma, and renal cell carcinoma), development of one or more clinical factors, development of intestinal cancer, or recovery from the disease.

The term "response to anti-cancer therapy (e.g., PI3K-mTORC1-S6K1 signaling pathway inhibitor therapy)" relates to any response of the hyperproliferative disorder (e.g., cancer) to an anti-cancer therapy (e.g., PI3K-mTORC1-S6K1 signaling pathway inhibitor therapy), such as anti-PI3K inhibitor therapy), preferably to a change in tumor mass and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related), "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., $p<0.05$) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the invention, or a fragment thereof, short interfering RNA (siRNA), and small molecules which interfere with or inhibit expression of a target biomarker nucleic acid by RNA interference (RNAi).

"RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., anti-immune checkpoint inhibitor, chemotherapeutic, and/or radiation therapy). In some embodiments, normal cells are not affected to an extent that causes the normal cells to be unduly injured by the anti-cancer therapy (e.g., PI3K-mTORC1-S6K1 signaling pathway inhibitor therapy). An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "synergistic effect" refers to the combined effect of two or more anti-immune checkpoint inhibitor agents can be greater than the sum of the separate effects of the anticancer agents alone.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "subject" refers to any healthy animal, mammal or human, or any animal, mammal or human afflicted with a cancer, e.g., lung, ovarian, pancreatic liver, breast, prostate, and colon carcinomas, as well as melanoma and multiple myeloma. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT: |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Gln, E) | GAA, GAG |
| Glutamine (Gln, Q) | CAA, CAG |
| Glycine (Gly, G) | GGA GGC GGG, GGT |
| Histidine (His, H) | CAC, CAT |
| Isoleucine (He, 1) | ATA, ATC, ATT |
| Leucine (Len, L) | CTA, CTC, CTG, CTT, TTA, TTG |
| Lysine (Lys, K) | AAA, AAG |
| Methionine (Met, M) | ATG |
| Phenylalanine (Phe, F) | TTC, ITT |
| Proline (Pro, P) | CCA, CCC, CCG, CCT |
| Serine (Ser, S) | AGG, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention and related biomarkers (e.g., biomarkers listed in Tables 1 and 2) are well known in the art and readily available on publicly available databases, such as the National Center for Biotechnology Information (NCBI). For example, exemplary nucleic acid and amino acid sequences derived from publicly available sequence databases are provided below.

As used herein, "c-MYC 5' UTR" refers to the 5' untranslated region of a c-MYC RNA molecule, or portion thereof, that is regulated by the PI3K-mTORC1-S6K1 signaling pathway (e.g., via eIF4A and/or eIF4B). The 5' UTR of human c-MYC nucleic acid is publicly available on the GenBank database maintained by the U.S. National Center for Biotechnology Information as nucleotides 1-525 of NM_0024067.4. Nucleic acid and polypeptide sequences of eIF4B orthologs in species other than humans are also well known and include, for example, nucleotides 1-627 of the mouse c-MYC nucleic acid sequence (NM_001177352.1), nucleotides 1-537 of the rat c-MYC nucleic acid sequence (NM_012603.2), and nucleotides 1-592 of the pig c-MYC nucleic acid sequence (NM_1005154.1).

Representative sequences of c-MYC orthologs, as well as their 5' UTRs, are presented below in Table 1. It is to be noted that the term can further be used to refer to any combination of features described herein regarding c-MYC 5' UTR molecules. For example, any combination of sequence composition, percentage identify, sequence length, domain structure, functional activity, etc. can be used to describe a c-MYC 5' UTR molecule of the present invention.

TABLE 1

```
SEQ ID NO: 1 Human cMYC 5'UTR cDNA Sequence (Nucleotides 1-525 of
NM_002467.4)
    1  gaccccgag  ctgtgctgct  cgcggccgcc  accgccgggc  cccggccgtc  cctggctccc
   61  ctcctgcctc  gagaagggca  gggcttctca  gaggcttggc  gggaaaaaga  acggagggag
  121  ggatcgcgct  gagtataaaa  gccgttttc   ggggctttat  ctaactcgcc  gtagtaattc
  181  cagcgagagg  cagagggagc  gagcgggcgg  ccggctaggg  tggaagagcc  gggcgagcag
  241  agctgcgctg  cgggcgtcct  gggaaggag   atccggagcg  aacaggggc   ttcgcctctg
  301  gcccagccct  cccgctgatc  ccccagccag  cggtccgcaa  cccttgccgc  atccacgaaa
  361  ctttgcccat  agcagcgggc  gggcactttg  cactggaact  tacaacaccc  gagcaaggac
  421  gcgactctcc  cgacgcgggg  aggctattct  gcccatttgg  ggacacttcc  ccgccgctgc
  481  caggacccgc  ttctctgaaa  ggctctcctt  gcagctgctt  agacg SEQ ID NO: 2 Mouse c-MYC 5'UTR cDNA Sequence (Nucleotides 1-627 of
NM_001177352.1)
    1  cccgcccacc  cgcccttat   attccggggg  tctgcgcggc  cgaggacccc  tgggctgcgc
   61  tgctctcagc  tgccgggtcc  gacccgcctc  actcagctcc  cctcctgcct  cctgaagggc
  121  agggcttcgc  cgacgcttgg  cgggaaaaag  aagggagggg  agggatcctg  agtcgcagta
  181  taaaagaagc  ttttcgggcg  ttttttttctg  actcgctgta  gtaattccag  cgagagacag
  241  agggagtgag  cggacggttg  gaagagccgc  gtgtgcagag  ccgcgctccg  gggcgaccta
  301  agaaggcagc  tctggagtga  gaggggcttt  gcctccgagc  ctgccgccca  ctctccccaa
  361  ccctgcgact  gacccaacat  cagcggccgc  aaccctcgcc  gccgctggga  aactttgccc
  421  attgcagcgg  gcagacactt  ctcactggaa  cttacaatct  gcgagccagg  acaggactcc
  481  ccaggctccg  gggagggaat  ttttgtctat  ttggggacag  tgttctctgc  ctctgcccgc
  541  gatcagctct  cctgaaaaga  gctcctcgag  ctgtttgaag  gctggatttc  ctttgggcgt
  601  cggaaacccc  gcagacagcc  acgacg SEQ ID NO: 3 Rat c-MYC 5'UTR cDNA Seouencc (Nucleotides 1-537 of
NM_012603.2)
    1  acccccgggc  tgcgctgctc  tccgctgccg  cctccgccgc  gcccaccccg  ctcgcctcct
   61  gcctccaaaa  gggcagggct  tcgccgaggc  ttggcgggaa  aaagaagcga  ggggagggat
  121  ccggagtcgc  agtataaaag  aagccccttcg  ggcgttttttt  ttctgactcg  ctgtagtaat
  181  tccagcgaga  gacagaggga  gtgagcgggc  gggttggaag  cgcccagtgt  gcagagcccc
  241  actccgggct  tcctaggaag  gcagctctgg  agtgagaagg  gctttgcctc  caggcttgct
  301  gcctcctcga  cccaatcctc  ccgctgaccc  aacatcagcg  gtcgcaaccc  tgccgcctc
  361  tgggaaactt  tgcccattgc  aacgggcaga  cacttctcac  tggaacttac  aatctgcgag
  421  ccaggacagg  actccccagg  cgcagggag   ggaattttg   tctatttggg  gacagtgttc
  481  cctgccctg   cccgcgaccg  gctccctga   aaagagctcc  tcgcgttatt  tgaagc SEQ ID NO: 4 Pig c-MYC 5'UTR cDNA Sequence (Nucleotides 1-592 of
NM_001005154.0
    1  tataggcgag  ggtctgcgcg  gctggggacc  ctccggctgc  gcatctctcg  gctgccgccg
   61  ccttttgccgc  acccccggcca  ccgctaggct  ccccactgcc  tctggaaggg  cagggctata
  121  cagaggcttg  gcgggaaaaa  gagcacggag  gggaggggtg  ttcctagcag  cataaaagcc
  181  ggttttctgg  gctttctctg  actcgctgta  gtaattccag  cgagaggcag  agggagcgag
  241  cgggcgggcc  ctccagggtg  gaagagcaga  gccggccgag  caatctgagt  cgcgctctgg
```

TABLE 1-continued

```
301 gcgcccgggg gaagggagat ccggagtgaa agagggtctt cgcctccgtc ccggccgccc
361 ccacccacc  ctgcccgccg accctgcca  gcggtccgcc accgcgccg  catccacgaa
421 actttgccca ctgcagcggg cgggtacttt ccactggaac ttacaacacc cgagcgacaa
481 cgcgactctc cggacgcgga gaggctattc tgcctatttg gggagacact tttccctgtc
541 gctgcccacg actcgctcct ctgaaaggcg ccctcgccg  cttttggac  gc
```

*Included in Table 1 are RNA nucleic acid molecules (e.g., thymines replaced with uredines), as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein, such as regulating the translation of c-MYC by the PI3K-mTORC1-S6K1 signaling pathway (e.g., via eIF4A and/or eIF4B). For example, reported point mutations of the c-MYC 5'UTR in human cancer cell lines have been suggested to be critical for its translation efficiency. In one embodiment, Ramos, a Burkitt lymphoma cell line, has been reported to have an A to T transversion located 33 necleotides from the 3'end of exon 1 (Wilman et al., 1984), which has been shown to be critical for its translation efficiency. Many other Burkitt lymphoma cells also have been identified to have deletion or point mutations in their c-MYC 5'UTR, including BL29, BL67, ST406, JD38. Manca, CA46 which have the deletion of exon 1 in their c-MYC 5'UTR. BL64 has a C to G point mutation located 30 necleotides from the 3'end of exon 1; P3HR1, BL60, AG876 have monoallelic mutation in the 3' PvuII site in exon 1 and the Daudi cell has multiple mutations in its 5'UTR (Stephen R. Hann ct al., 1987).

As used herein, "eIF4a" refers to the eukaryotic translation initiation factor 4A member of the eukaryotic translation initiation factor family and is alternatively known as "eIF4A1," "BM-010," and "DDC2A." At least two splice variants encoding two distinct human eIF4a isoforms exist and sequences are publicly available on the GenBank database maintained by the U.S. National Center for Biotechnology Information. For example, human eIF4A transcript variant 1 (NM_001416.3) encodes the long human eIF4A isoform 1 (NP_001407.1). Human eIF4a transcript variant 2 (NM_001204510.1) uses an alternate splice site that causes a frameshift in the 3' coding region compared to variant 1, resulting in an isoform (NP_001191439.1) with a distinct and shorter C-terminus compared to isoform 1. Nucleic acid and polypeptide sequences of eIF4B orthologs in species other than humans are also well known and include, for example, mouse eIF4A (NM_144958.4, NP_659207.1, NM_001159375.1, and NP_001152847.1), chimpanzee eIF4A (NM_001098575.1 and NP_001092045.1), monkey eIF4A (XM_001085678.2, XP_001085678.1, XM_001085318.2, and XP_001085318.1), dog eIF4A, (NM_001251942.1 and NP_001238871.1), cow eIF4A (NM_001034228.1 and NP_001029400.1), and rat eIF4A (NM_199372.2 and NP_955404.1). Representative sequences of eIF4A orthologs are presented below in Table 2. Anti-eIF4A agents, including antibodies, nucleic acids, and the like are well-known in the art and include, for example, antibodies such as, STJ32135 and STJ27247 (St. John's Laboratory), LS-C100819 and LS-C148474 (Lifespan Biosciences), OAAB04214 (Aviv Systems Biology), PA5-23273 (Thermo Fisher Scientific, Inc.), and nucleic acids, such as TR313247 (OriGene). In addition, other inhibitors of eIF4A (e.g., small molecules) are known and include, for example, hippuristanol and others. It is to be noted that the term can further be used to refer to any combination of features described herein regarding eIF4A molecules. For example, any combination of sequence composition, percentage identify, sequence length, domain structure, functional activity, etc. can be used to describe eIF4A molecule of the present invention.

As used herein, "eIF4B" refers to the eukaryotic translation initiation factor 4B member of the eukaryotic translation initiation factor family and is alternatively known as "EIF-4B" and "PRO1843." Human eIF4B nucleic acid (NM_001417.4) and amino acid (NP_001408.2) sequences are publicly available on the GenBank database maintained by the U.S. National Center for Biotechnology Information. Nucleic acid and polypeptide sequences of eIF4B orthologs in species other than humans are also well known and include, for example, mouse eIF4B (NM_145625.3 and NP_663600.2), chimpanzee eIF4B (XM_003313676.1, XP_003313724.1, XM_001142097.3, and XP_001142097.3), monkey eIF4B (NM_001195808.1 and NP_1182737.1), dog eIF4B (XM_853888.2, XP_858981.2, XM_853812.2, and XP_858905.2), cow eIF4B (NM_001035028.2 and NP_001030200.1), rat eIF4B (NM_001008324.1 and NP_001008325.1), and chicken eIF4B (XM_003643408.2 and XP_003643456.2). Representative sequences of eIF4B orthologs are presented below in Table 2. Anti-eIF4B agents, including antibodies, nucleic acids, and the like are well-known in the art and include, for example, antibodies such as, STJ31908 and STJ47560 (St. John's Laboratory), OAAB01285 and OAAB15068 (Aviva Systems Biology), LS-B7216 and LS-B7776 (Lifespan Biosciences), PA5-23261 (Thermo Fisher Scientific, Inc.), and nucleic acids, such as sc-77253 (Santa Cruz Biotechnology) and shAAV-258227 (Vector Biolabs). In addition, other inhibitors of eIF4B (e.g., small molecules) are known. It is to be noted that the term can further be used to refer to any combination of features described herein regarding, eIF4B molecules. For example, any combination of sequence composition, percentage identify, sequence length, domain structure, functional activity, etc. can be used to describe an eIF4B molecule of the present invention.

TABLE 2

```
SEQ ID NO: 5 Human eIF4A (variant 1) cDNA Sequence (NM_001416.3)
    1 atgtctgcga gccaggattc ccgatccaga gacaatggcc ccgatgggat ggagcccgaa
   61 ggcgtcatcg agagtaactg gaatgagact gttgacagct ttgatgacat gaacctctcg
  121 gagtccctt  tccgtggcat ctacgcgtat ggttttgaga agccctctgc catccagcag
  181 cgagccattc taccctgtat caagggttac gatgtgattg ctcaagccca atctgggact
  241 gggaaaacgg ccacatttgc catatcgatt ctgcagcaga ttgaattaga tctaaaagcc
  301 acccaggcct tggtcctagc acccactcga gaattggctc agcagataca gaaggtggtc
  361 atggcactag gagactacat gggcgcctcc tgtcacgcct gtatcggggg caccaacgtg
  421 cgtgctgagg tgcagaaact gcagatggaa gctccccaca tcatcgtggg taccctggc
```

TABLE 2-continued

```
 481  cgtgtgtccg atatgcttaa ccggagatac ctgtccccca aatacatcaa gatgtttgta
 541  ctggatgaag ctgacgaaat gttaagccgt ggattcaagg accagatcca tgacatatcc
 601  caaaagctca acagcaacac ccaggtagtt ttgctgtcag ccacaatgcc ttctgacgtg
 661  cttgaggcga ccaagaagtt catgagggac ccattcgga ctcttgtcaa gaaggaagag
 721  ttgaccctgg agggtatccg ccagttctac atcaacgtgg aacgagagga gtggaagctg
 781  gacacactat gtgacttgta tgaaaccctg accatcaccc aggcagccat cttcatcaac
 841  acccggagga aggtggactg gctcaccgag aagatgcatg ctcgagattt cactgtatcc
 901  gccatgcatg gagatatgga ccaaaaggaa cgagacgtga ttacgaggga gtttcgttct
 961  ggctctagca gagtttttgat taccactgac ctgctggcca gaggcattga tgtgcagcag
1021  gtttcttag tcatcaacta tgaccttccc accaacaggg aaaactatat ccacagaacc
1081  ggtcgaggtg gacgtttgg ccgtaaaggt gtggctatta acatggtgac agaagaagac
1141  aagaggactc ttcgagacat tgagaccttc tacaacacct ccattgagga aacgcccctc
1201  aatgttgctg acctcatctg a SEQ ID NO: 6 Human eIF4A (isoform 1) Amino Acid Sequence (NP_001407.1)
   1  msasqdsrsr dngpdgmepe gviesnwnei vdsfddmnis eslrgiyay gfekpsaiqq
  61  railpcikgy dviaqaqsgt gktatfaisi lqqieldlka tqalvlaptr elaqqiqkvv
 121  malgdymgas chaciggtnv raevqklqme aphiivgtpg rvfdminrry lspkyikmfv
 161  ldeademlsr gfkdqiydif qklnsntqvv llsatmpsdv levtkkfmrd pirilvkkee
 241  ltlegirqfy invereewkl dtlcdlyetl titqavifin trrkvdwlte kmhardfevs
 301  amhgdmdqke rdvimrsfrs gssrvlittd llargidvqq vslvinydlp tnrenyihri
 361  grggrfgrkg vainmvteed krtltdietf yntsieempl nvadli SEQ ID NO: 7 Human eIF4A (variant 2) cDNA Sequence (NM_001204510.1)
   1  atgtctgcga gccaggattc ccgatccaga gacaatggcc ccgatgggat ggagccggaa
  61  ggcgtcatcg agagtaactg gaatgagatt gttgacagct ttgatgacat gaacctctcg
 121  gagtcccttc tccgtggcat ctacgcgtat ggttttgaga agccctctgc catccagcag
 181  cgagccattc taccttgtat caagggttat gatgtgattg ctcaagccca atctgggact
 241  gggaaaacgg ccacatttgc catatcgatt ctgcagcaga ttgaattaga tctaaaagcc
 301  acccaggcct tggtcctagc acccactcga gaattggctc agcagataca gaaggtggtc
 361  atggcactag agactacatg ggcgcctcc tgtcacgcct gtatcgggg caccaacgtg
 421  cgtgctgagg tgcagaaacc gcagatggaa gctccccaca ccatcgtggg tacccctggc
 481  cgtgtgtttg atatgcttaa ccggagatac ctgtccccca aatacatcaa gatgtttgta
 541  ctggatgaag ctgacgaaat gttaagccgt ggattcaagg accagatcta tgacatattc
 601  caaaagctca acagcaacac ccaggtagtt ttgctgtcag ccacaatgcc ttctgatgtg
 661  cttgaggtga ccaagaagtt catgagggac ccattcgga ttccttgtcaa gaaggaagag
 721  ctgaccctgg agggcatccg ccagttctac atcaacgtgg aacgagagga gtggaagctg
 781  gacacactat gtgacttgta tgaaaccctg accatcaccc aggcagtcat cttcatcaac
 841  acccggagga aggtggactg gctcaccgag aagatgcatg ctcgagactt cactgtatcc
 901  gccatgcatg gagatatgga ccaaaaggaa cgagacgtga ttatgaggga gcttcgttct
 961  ggctctagca gagttttgat taccactgac ctgctgggaa aactatatcc acagaatcgg
1021  tcgaggtgga cggcttggcc gtaa SEQ ID NO: 8 Human eIF4A (variant 2) Amino Acid Sequence (NP_001191439.1)
   1  msasqdsrsr dngpdgmepe gviesnwnei vdsfddmnls eslrgiyay gfekpsaiqq
  61  railpcikgy dviaqaqsgt gktatfaisi lqqieldlka tqalvlaptr elaqqiqkvv
 121  malgdymgas chaciggtnv raevqklqme aphiivgtpg rvfdminrry lspkyikmfv
 181  ldeademlsr gfkdqiydif qklnsntqvv llsatmpsdv levtkkfmrd pirilvkkee
 241  ltlegirqfy invereewkl dtlcdlyetl titqavifin trrkvdwlte kmhardftvs
 301  amhgdmdqke rdvimrefrs gssrvlittd llgklypqnr srwtvwp SEQ ID NO: 9 Mouse eIF4A cDNA Sequence (NM_144958.4)
   1  atgtctgcga gtcaggattc tcgatccaga gacaatggcc ccgacgggat ggagccggaa
  61  ggcgccatcg agagtaactg gaacgagatt gtggatagct ttgatgacat gaatctctca
 121  gagtcccctcc tccgtggtat ttatgcctat ggttttgaga agccctctgc catccagcag
 181  cgagctattc ttccttgtat caagggttat gatgtgattg ctcaagccca gtctgggact
 241  gggaaaacag ctacatttgc cacatcaatt ctgcagcaga ttgaattaga tctaaaggcc
 301  actcaggctt tggttctggc acccacacgt gaattggctc agcagataca aaaggtggtt
 361  atggcactag agactacat gggtgcctct cgtcatgcct gcattggggg caccaatgtg
 421  cgtgctgagg tgcagaagct gcagatggaa gctccccata tcatcgtggg tacccctggc
 481  cgggtgtttg acatgcttaa ccggagatac ctgtcccccaa aatacatcaa gatgttcgta
 541  ctggatgaag cagatgaaat gttaagccga gggttcaagg atcagatcta tgacatattc
 601  cagaagctca acagcaacac acagtagtt ttgttgtctg ctacaatgcc ttctgatgtc
 661  cttgaggtga ccaagaaatt tatgagagac cctattcgga ttccttgtcaa gaaggaagaa
 721  ttgaccctgg agggtatccg ccaattctac accaatgtgg aacgagagga gtggaagctt
 781  gacacattgt gtgacttgta tgagacgctg accatcaccc aggcagtcat ctttatcaac
 841  accagaagga aggtggactg gctcaccgag aagatgcatg cccgagattt cactgtttct
 901  gccatgcacg gagatatgga ccaaaaggaa cgagatgtga tcatgaggga gttccggtct
 961  ggctctagca gagtattaat taccactgac ctgttggcca gaggcattga tgtgcagcag
1021  gtctcttag ccatcaacta tgaccttccc accaacaggg aaaactacat ccacagaatc
1081  ggtcgaggtg gtcggtttgg tcgtaagggt gtggctatta acatggtgac cgaagaagac
1141  aagaggactc ttcgagacat tgagactttc tacaacacct ccattgagga tgcccctc
1201  aacgttgctg acctcatttg a SEQ ID NO: 10 Mouse eIF4A Amino Acid Sequence (NP_659207,1)
   1  msasqdsrsr dngpdgmepe gvieanwnei vdsfddmnls eslrgiyay gfekpsaiqq
  61  railpcikgy dviaqaqsgt gktatfaisi lqqieldlka tqalvlaptr elaqqiqkvv
 121  malgdymgas chaciggtnv raevqklqme aphiivgtpg rvfdmlnrry lspkyikmfv
 181  ldeademlsr gfkdqiydif qklnsntqvv llsatmpsdv levtkkfmrd pirilvkkee
 241  ltlegirqfy invereewkl dticdlyetl titqavifin trrkvdwlte kmhardfevs
```

TABLE 2-continued

```
301    amhgdmdqke rdvimrefrs gssrvlittd llargidvqq vslvinydlp tnrenyihri
361    grggrfgrkg vainmvteed krtlrdietf yntsieempl nvadli SEQ ID NO: 11 Chimpanzee eIF4A cDNA Sequence (NM_001098575.1)
   1    atgtctgcga gccaggattc ccgatccaga gacaatggcc ccgatgggat ggagcccgaa
  61    ggcgtcatcg agagtaactg gaatgagatt gttgacagct tgatgacat gaacctctcg
 121    gagtcccttc tccgtggtat ctacgcctat ggttttgaga agccctctgc catccagcag
 181    cgagccattc taccttgtat caagggttat gatgtgattg ctcaagccca atctgggact
 241    gggaaaacgg ccacatttgc catatcgatt ctgcagcaga ttgaattaga tctaaaagcc
 301    acccaggcct tggtcctagc acccactcga gaattggctc agcagataca gaaggtggtc
 361    atggcattag agactacatg ggcgcctcc tgtcacgcct gtatcggggg caccaacgtg
 421    cgtgctgagg tgcagaaact gcagatggaa gctccccaca tcatcgtggg tacccctggc
 481    cgtgtgttcg atatgcttaa ccggagatac ctgtccccca agtacatcaa gatgtttgta
 541    ctggatgaag ctgacgaaat gttaagccgt ggattcaagg accagatcta tgacatatcc
 601    caaaagctca acagcaacac ccaggtagtt ttgctgtcag ccacaatgcc ttctgatgtg
 661    cttgaggtga ccaagaagtt catgagggac ccattcgga ttctcgtcaa gaaggaagag
 721    ttgacccctg agggtatccg ccagttctac atcaacgtgg aacgagagga gtggaagctg
 781    gacacactat gtgacttgta tgaaaccctg accatcaccc aggcagtcat cttcatcaac
 841    acccgggagga aggtggactg gctcaccgag aagatgcatg ctcgagattt cactgtatcc
 901    gccatgcatg gagatatgga ccaaaaggaa cgagacgtga tcatgaggga gtttcgttct
 961    ggctccagca gagttttgat taccactgac ctgctggcca gaggcattga tgtgcagcag
1021    gtttctttag tcatcaacta tgaccttccc accaacaggg aaaactatat ccacagaatc
1081    ggtcgaggtg gacggttcgg ccgtaaaggc gtgactatta acatggtgac agaagaagac
1141    aagaggactc ttcgagacat tgagaccttt tacaacacct ccattgagaa aatgccctc
1201    aatgttgctg acctcatctg a SEQ ID NO: 12 Chimpanzee eIF4A Amino Acid Sequence (NP_001092045.1)
   1    msasqdsrsr dngpdgmepe gviesnwnei vdsfddmnls esllrgiyay gfekpsaiqq
  61    railpcikgy dvlaqaqagt gktatfaisi lqqieldlka tqalvlaptr elaqqlqkvv
 121    malgdymgas chaciggtnv raevqklqme aphiivgtpg rvfdmlnrry lapkyikmfv
 181    ldeademlsr gfkdqiydif qklnsntqvv llsatmpsdv levtkkfmrd pirilvkkee
 241    ltlegirqfy invereewkl dtlcdlyeti titqavifin trrkvdwlte kmhardftvs
 301    amhgdmdqke rdvimrefrs gssrvlittd llargidvqq vslvinydlp tnrenyihri
 361    grggrfgrkg vtinmvteed krtlrdietf yntsieempl nvadli SEQ ID NO: 13 Monkey eIF4A cDNA Sequence (XM_001085678.2)
   1    atgtctgcga gccaggattc ccgatccaga gacaatggcc ccgatggaat ggagcccgaa
  61    ggcgtcatcg agagtaaccg gaatgagatt gttgacagct tgatgacat gaacctctca
 121    gagtctcttc tccgtggcat ctacgcctat ggttttgaga agccgtctgc catccagcag
 181    cgagccattc taccttgtat caagggttac gatgtgatcg ctcaagccca atctgggact
 241    gggaaaacgg ccacatttgc catatcaatt ctgcagcaga tcgaattaga tctaaaagcc
 301    acccaggcct tggtcctggc acccactcga gaattggctc agcagataca gaaggtggtc
 361    atggcactag agactacatg ggcgcctcc tgtcatgcct gtattgggg caccaacgtg
 421    cgtgctgagg tgcagaaact gcagatggaa gccccccaca taatcatggg gaccccctggc
 481    cgagtgtttg atatgcttaa ccggagatac ctgtctccca atacaccaa gatgtttgta
 541    ctggacgaag ctgatgaaat gttaagccgt ggattcaagg accagatcta cgacatattc
 601    caaaagctca acagcaacac ccaggtagtt ttgctgccag ctacaatgcc ttctgatgtg
 661    cttgaggtga ccaagaagtt catgagggac ccattcgga ttcttgtcaa gaaggaagag
 721    ctgaccctgg agggtatctg ccaattctac atcaacgtgg aacgagagga gtggaagctg
 781    gacacactat gtgacttgta tgaaacgctg accatcaccc aggcagtcat cttcatcaac
 841    acccgaggga aggtggactg gctcaccgag aagatgcatg ctcgagattt cactgtctct
 901    gccatgcatg gagatatgga ccaaaaggaa cgagacgtga tcatgaggga gtttcgttct
 961    ggctctagca gagttttgat taccactgac ctgctggcca gaggcattga tgtgcagcag
1021    gtttctttag tcatcaacta tgaccttccc accaacaggg aaaactatat ccacagaatc
1081    ggtcgaggtg gacggcttgg ccgtaaaggt gtggctatta acatggtgac agaagaagac
1141    aagaggactc ttcgagacat cgagaccttt tataacacct ccattgagaa aatgccctc
1201    aatgttgccg acctcatctg a SEQ ID NO: 14 Monkey eIF4A Amino Acid Sequence (XP_001085678.1)
   1    msasqdsrsr dngpdgmepe gviesnwnei vdsfddmnls esllrgiyay gfekpsaiqq
  61    railpcikgy dviaqaqsgt gktatfaisi lqqieldlka tqalvlaptr elaqqiqkvv
 121    malgdymgas chaciggtnv caevqklqme aphiimgtpg rvfdmlnrry lspkyikmfv
 181    ldeademlsr gfkdqiydif qklnsntqvv llsatmpsdv levtkkfmrd pirilvkkee
 241    ltlegicqfy invereewkl dtlcdlyetl titqavifin tqrkvdwlte kmhardftvs
 301    amhgdmdqke rdvimrefrs gssrvlittd llargidvqq vslvinydlp tnrenyihri
 361    grggrfgckg vainmvteed krtlrdietf yntsieempl nvadli SEQ ID NO: 15 Dog eIF4A cDNA Sequence (NM_001251942.1)
   1    atgtctgcga gtcaggattc ccgatccaga gacaatggcc ccgatgggat ggagcccgaa
  61    ggcgtcatcg agagtaactg gaatgagatt gttgacagct tgatgacat gaacctctcc
 121    gagtcccttc tccgtggcat ctatgcttat ggtttcgaga agccttctgc catccagcag
 181    cgagccattc ttccttgtat caagggttat gatgtgatcg ctcaagccca atctgggact
 241    gggaaaacag ccacctttgc catatcgatt ctgcaacaaa ttgaattgga tctaaaggct
 301    acacaggcct tggtcctggc acccactagg gagttggctc agcagataca gaaggtagtc
 361    atggcattag agattacatg ggtgcttcc tgccatgccc gcattggggg gaccaatgta
 421    cgtgctgagg tgcagaagct tcagatggag gctcctcata tcatcgtggg cacccccggt
 481    cgtgtgtttg acatgctgaa ccggagatac ctatccccca aatatatcaa gatgtttgta
 541    ctggacgaag ctgatgagat gttaagccgt ggattcaagg accagatcta cgacatattc
 601    caaaagctca acagcaacac ccaggcggct ttgctgtctg ccacgatgcc ttctgacgtg
 661    cttgaggtga ccaagaagtt catgagggac ccattcgga ttctggtcaa gaaagaagag
```

TABLE 2-continued

```
 721    ttgaccctcg agggcatccg ccagttctac accaacgtgg agcgagagga gtggaagctg
 781    gacacgctgc gtgacctgca cgagactctg accatcacac aggcagtcat tctcatcaac
 341    acccgaagga aggtggattg gctcaccgag aagatgcacg cccgagactt caccgtgtct
 901    gccatgcacg gagacatgga ccagaaggag cgagatgtca tcatgagga gttccgctcg
 961    ggctctagca gagtactgat taccactgac ttgctggcca gaggcatcga tgtgcagcag
1021    gtgtctctag tcatcaacta tgaccttcct accaacaggg aaaactatac ccacagaatc
1081    ggccgtggtg gacgatttgg ccggaagggt gtggctatta acatggtgac agaagaagac
1141    aagaggactc ctcgagacat cgagactttc tacaacacct ccattgagga aatgcccctc
1201    aatgttgctg acctcatctg a
```

SEQ ID NO: 16 Dog eIF4A Amino Acid Sequence (NP_001238871.1)
```
  1    msasqdsrsr dnqpdgmepe qviesnwnei vdsfddmnls esllrgiyay gfekpsaiqq
 61    railpcikgy dviaqaqsgt gktatfaisi lqqieldlka tqalvlaptr elaqqlqkvv
121    malgdymgas chaciggtnv raevqklqme aphiivgtpg rvfdmlnrry lspkyikmfv
181    ldeademlsr gfkdqiydif qklnsntqvv llsatmpsdv levtkkfmrd pirilvkkee
241    ltlegirqfy invereewkl dtlcdlyetl titqavifin trrkvdwlte kmhardftvs
301    amhgdmdqke rdvimrefrs gssrvlittd llargidvqq vslvinydlp tnrenyihri
361    grggrfgrkg vainmvteed krtlrdietf yntsieempl nvadli
```

SEQ ID NO: 17 Cow eIF4A cDNA Scoucncc (NM_001034228.1)
```
  1    atgtctgcga gtcaggattc ccgatctaga gacaatggcc ccgatgggat ggaacccgaa
 61    ggcgtcatcg agagtaactg gaatgagatt gtcgacagct tgatgacat gaacctctca
121    gagtcactcc tccgtggcat atatgcctat ggttttgaga agccctctgc cattcagcag
181    cgagccattc tccttgtat caagggttat gatgtgattg ctcaagccca atctgggact
241    gggaaaacgg ccacttttgc catatcaatt ctgcaacaga ttgaattaga tctaaaggcc
301    acccaggcct tggtcctggc acccactaga gagttggccc agcagataca gaaggtagta
361    atggccttag agattacat gggtgcctcg tgccatgcct gcattggggg taccaatgta
421    cgtgctgagg tgcagaagct gcagatggaa gcccccata tcatcgtggg taccccaggc
481    cgtgtgttcg acatgcttaa ccggagatac ttgtctccca aatacatcaa gatgttgtca
541    ctggatgaag ctgacgaaat gttaagccgt ggatccaagg accagatcta tgacatattc
601    cagaagctca acagcaacac ccaggtggtt ttgctgtcag ctacaatgcc ttctgatgtg
661    cttgaggtga ccaagaagtt catgagggac ccaattagaa ttcttgtcaa gaggaagag
721    tgacgctgg agggtatccg tcagttctac atcaatgtgg aacgagagga gtggaagctg
781    gacacactgt gcgacttgta tgaaacctg accattcaca aggcagtcat cttcatcaac
341    acccgaagga aggtggattg gctcaccgag aagatgcatg cccgagactt caccgtctct
901    gccatgcacg gagacatgga ccaaaaagaa cgagacgtta tcacgaggga gttccgctct
961    ggctctagca gagtattgat taccactgac ctactggcca gaggtattga tgtacagcaa
1021    gttctcttag tcatcaacta tgactccccc accaataggg aaaactatac ccacagaatt
1081    ggtcgtggcg gacgtttcgg ccgtaagggt gtggctatta acatggtgac agaagaggac
1141    aagaggactc ttcgagacat cgaaaccttc tacaacacct ccattgagga aatgcccctc
1201    aatgttgctg acctcatctg a
```

SEQ ID NO: 18 Cow eIF4A Amino Acid Sequence (NP_001029400.1)
```
  1    msagqdsrsr dngpdgmepe gvlesnwnei vdsfddmnla esllrgiyay gfekpsaiqq
 61    railpcikgy dviaqaqsgt gktatfalsi lqqleldlka tqalvlaptr elaqqiqkvv
121    malgdymgas chaciggtnv raevqklqme aphiivgtpg rvfdmlnrry lspkyikmfv
181    ldeademlsr gfkdqiydlf qklnsntqvv llsatnpsdv levtkkfmrd pirilvkkee
241    ltlegirqfy invereewkl dtlcdlyetl titqavifin trrkvdwlte kmhardftvs
301    amhgdmdqke rdvimrefrs gsarvlittd llargldvqq vslvinydlp tnrenyihri
361    grggrfgrtkg vainmvteed krtlrdietf yntsieempl nvadli
```

SEQ ID NO: 19 Rat eIF4A cDNA Sequence (NM_199372.2)
```
  1    atgtctgcga gtcaggattc tcgatccaga gacaatgggc ccgatgggat ggagccggaa
 61    ggcgtcatcg agagtaactg gaatgagatt gtggatagct tcgatgacat gaatctctca
121    gaatccctcc tccgtggtat ttatgcctat ggttttgaga agccctctgc catccagcag
181    cgagctattc ttccttgtat caagggttat gatgtgattg ctcaagccca gtctgggact
241    gggaaaacag ctacatttgc catatccatt ctgcagcaga ttgaattaga tctaaaggcc
301    actcaggctt tggttctggc acccaccgt gaattggctc agcagattca aaaggtggtt
361    atggcactgg gagactacat gggtgcctct tgtcatgcct gtattggggg taccaacgtg
421    cgtgctgagg tgcagaagct gcaaatggaa gctccccata tcatcgtggg caccctggc
481    cgggtgttcg atatgcttaa ccggagatac ctgtcaccca atacatcaa gatgttcgtc
541    ctggatgaag cagatgaaat gctaagccgt gggttcaagg atcagatcta tgatacattc
601    caaaagctca acagcaacac acagcagtt tgccgccga ccacaatgcc ttctgatgtc
661    cttgaggcga ctaagaagtt catgagagac cctactcgga ttcttgtcaa gaggaagag
721    ttgaccctgg agggtatccg ccaattctac atcaatgtgg aacgagagga gtggaagctc
781    gacacattgt gtgacttgta tgaaacactg accatcaccc aggcagtaat ctttattaat
841    accagaagga aggtggactg gctcactgag aagatgcatg cccgggattc cacgtttct
901    gccatgcatg gagatatgga ccaaaaggaa cgagacgtga tcatgaggga gttccggtct
961    ggctctagca gagtattaat taccactgac ctgttggcca gaggcattga tgtgcagcag
1021    gtctccctag tcatcaatta tgaccttccc accaacaggg aaaactacat ccacagaatt
1081    ggtcgaggtg gtcggtttgg ccggaaaggt gtggctatta acatggtgac agaagaagac
1141    aagaggactc ttcgagacat tgagactttc tacaacacct ccattgagga tgcccctc
1201    aacgttgctg acctcatttg a
```

SEQ ID NO: 20 Rat eIF4A Amino Acid Sequence (NP_955404.1)
```
  1    msasqdsrar dngpdgmepe gvieanwnei vdsfddmnls esllrgiyay gfekpaaiqq
 61    railpcikgy dviaqaqsgt gktatfaisi lqqieldlka tqalvlaptr elaqqtqkvv
121    malgdymgas chaciggtnv raevqklqme aphiivgtpg rvfdmlnrry lapkyiknfv
181    ldeademlsr gfkdqiydif qklnsntqvv llsatmpsdv levtkkfmrd pirilvkkee
241    ltlegirqfy invereawkl dtlcdlyetl titqavifin trrkvdwlte kmhardftvs
```

TABLE 2-continued

```
301    amhqdmdqke rdvimrefrs qaarvlittd llargidvqq vslvinydlp tnrenyihri
361    grggrfgrkg vainmvteed krtlrdietf yntsieempl nvadli SEQ ID NO: 21 Human eIF4B cDNA Sequence (NM_001417.4)
   1    atggcggcct cagcaaaaaa gaagaataag aaggggaaga ctatctccct aacagacttt
  61    ccggctgagg atgggggtac cggtgaggga agcacctatg tttccaaacc agtcagctgg
 121    gctgatgaaa cggatgacct ggaaggagat gtttcgacca cttggcacag taacgatgac
 181    gacgtgtata gggcgcctcc aattgaccgt tccatccttc ccactgctcc acgggctgct
 241    cgggaaccca atatcgaccg gagccgtctt cccaaatcgc caccctacac tgcttttcta
 301    ggaaacctac cctatgatgt tacagaagag tcaattaagg aattcttccg aggattaaat
 361    atcagtgcag tgcgtttacc acgtgaaccc agcaatccag agaggttgaa aggttttggt
 421    tatgctgaat ttgaggacct ggattcctg ctcagtgccc tgagtctcaa tgaagagtct
 461    ctaggtaaca ggagaactcg agtggacgtt gctgatcaag cacaggataa agacaggat
 541    gatcgttctt ttggccgtga tagaaatcgg gattctgaca aaacagatac agactggagg
 601    gctcgtcctg ctacagacag ctttgatgac tacccaccta agagggtga tgatagcttt
 661    ggagacaagt atcgagatcg ttatgattca gaccggtatc gggatgggta tcgggatggg
 721    tatcgggatg gcccacgccg ggatatggat cgatatggtg gccgggatcg ctatgatgac
 781    cgaggcagca gagactatga tagaggctat gattcccgga taggcagtgg cagaagagca
 841    tttggcagtg ggtatcgcag ggatgatgac tacagaggag cgggggaccg ctatgaagac
 901    cgatatgaca gacgggatga tcggtcgcgg agctccagag atgattactc tcgggatgat
 961    tataggcgtg atgatagagg tccccccaa agacccaaac tgaatctaaa gcctcggagt
1021    actcctaagg aagatgattc ctctgctagt acctcccagt ccactcgagc tgcttctatc
1081    cttggagggg caaagcctgt tgacacagct gctagagaaa gagaagtaga gaacggcta
1141    cagaaggaac aagagaagtC gcagcgtcag ctggatgagc aaaactaga acgacggcct
1201    cgggagagac acccaagctg gcgaagtgaa gaaactcagg aacgggaacg gtcgaggaca
1261    ggaagtgagt catcacaaac tgggacctcc accacatcta gcagaaatgc acgaaggaga
1321    gagagtgaga agtctctaga aaatgaaaca ctcaataagg aggaagattg ccactctcca
1381    acctctaaac ctcccaaacc tgatcagccc ctaaaggtaa tgccagcccc tccaccaaag
1441    gagaatgctt gggtgaagcg aagttctaac cctcctgctc gatctcagag ctcagacaca
1501    gagcagcagt cccctacaag tggcggggga aaagtagctc cagctcaacc atctgaggaa
1561    ggaccaggaa ggaaagatga aaataaagta gatgggatga atgcccaaa aggccaaact
1621    gggaactcta gccgtggtcc aggagacgga gggaacagag accactggaa ggagtcagat
1681    aggaaagatg gcaaaaagga tcaagactcc agatctgcac ctgagccaaa gaaacctgag
1741    gaaaatccag cttccaagtt cagttctgca agcaagtatg ctgctctctc tgttgatggt
1801    gaagatgaaa atcagggaga agattatgcc gaatag SEQ ID NO: 22 Human eIF4B Amino Acid Sequence (NP_001408.2)
   1    maasakkknk kgktisltdf laedgdtggg styvakpvsw adetddlegd vsttwhsndd
  61    dvyrappidr silptapraa repnidrsrl pksppytafl gnlpydvtee sikeffrgln
 121    lsavrlprep snperlkgfg yaefedldsl lsalslnees lgnrrirvdv adqaqdkdrd
 181    drsfgrdrnr dsdktdtdwr arpatdsfdd ypprrgddsf gdkyrdryds dryrdgyrdg
 241    yrdgprrdmd ryggrdryyd rgsrdydrgy dsrigsgrra fgsgyrrddd yrgggdryed
 301    rydrrddrsw ssrddysrdd yrrddrgppq rpklnlkprs tpkeddssas tsqstraasi
 361    fggakpvdta arereveerl qkeqeklqrq ldepklerrp rerhpswrse etqerersrt
 421    gsessqtgts ttsarnarrr eseksllenet lnkeedchsp tskppkpdqp lkvmpapppk
 481    enawvkrssn pparsqssdt eggsptsggg kvapaqpsee gpgrkdenkv dgmnapkgqt
 541    gnsargpgdg gnrdhwkead rkdgkkdqds rsapepkkpe enpaskfaaa skyaalavdg
 601    edenegedya e SEQ ID NO: 23 Mouse eIF4B cDNA Sequence (NM_145625.3)
   1    atggcggcct cagcaaaaaa gaagaataag aaggggaaga ccatctccct aacggacttt
  61    ctagctgagg atggaggaac tggtgaggga agcacctatg tccccaaacc agtcagctgg
 121    gctgatgaaa cagacgatct ggaaggagat gtgtcaacaa cttggcatag taacgatgat
 181    gacgcgtaca gggcgcctcc aattgaccgt tccatccttc ccactgctcc acgggctgct
 241    cgggaaccca atattgaccg gagccgtctt cccaagtcgc accctacac tgcttttcta
 301    gggaatctgc cctatgatgt gacagaagac tccattaagg atttctttag aggattaaat
 361    atcagcgctg tacgcttacc acgggaaccc acaatccagc acaggttgaa aggtttcggt
 421    tacgcagaat tcgaggacct ggactctctg ctcagtgctc tgagtctcaa tgaagagtct
 481    ctaggtaaca ggagaattcg tgtggatgtt gctgatcaag cacaggataa agacagggat
 541    gaccgttctt ttggtcgaga tagaaatcgg gattctgaca aaacagacac agactggagg
 601    gcccgtccca ccacagacag ttttgatgac tacccaccta agagggcga tgatagcttt
 661    ggagacaagt atcgagatcg ttacgattca gaccggtatc gggatgggta tagggacgga
 721    tatcgggacg gcccacgcag agacatggac cgctatgggg gccgggatcg ctatgatgac
 781    cgaggcagca gagactatga ccgaggctat gactccagga taggcagtgg cagaagggca
 841    tttggaagtg ggCaccggag agatgacgac tacagaggag tgggggaccg ccatgaagac
 901    cgctatgaca gacgggatga tcggtcgtgg agctccaggg atgactactc tcgggatgat
 961    tataggcgtg atgacagagg tccccccag agacccgaac cgaacctcaa gcctcgaagc
1021    gctcctaagg aggatgacgc ctccgccagc acctcccagt ccagccgggc agcctccatc
1061    tttggagggg cgaagcccgt tgacacagct gccagggaaa gagaagtaga ggagcggcta
1141    cagaaggagc aggagaagct gcagcgtcag ctggatgagc aaaactaga ccgccggcct
1201    cgggagagac acccaagctg gcgaagtgaa gaaactcagg aaagagaacg gtcaaggaca
1261    ggaagtgagt catcgcagac tggggcctca gccacatctg gcagaaatac acgaaggaga
1321    gagagtgaga agtctctaga aaatgaaacc ctcaataaga aggaagactg tcactctcca
1381    accctaagc tcctaaaacc tgaccagcct ctaaaggtaa tgccagcccc tccaccaaag
1441    gagaatgcgt gggtgaagcg aagctctaac cctcctgccc gatctcagag ctcagacaca
1501    gagcagccgt cccctacaag tggtggaggg aaagtagctg cagtccagcc cctgaggaa
1561    ggaccatcaa gaaaagatgg aaataaagtg gatgtggtgg gtgccacaca aggccaagct
1621    ggaagctgca gccgtggtcc cggggatgga gggagcagag accactggaa ggacttggat
```

TABLE 2-continued

```
1681    aggaaggatg gcaaaaaaga tcaagactcc agatctgcgc ctgagccaaa gaaacctgag
1741    gagaacccag cctctaagtt cagctctgca agcaagtacg ctgctctgtc tgtggatggc
1801    gaggatgagg atgagggcga cgactgcact gagtag SEQ ID NO: 24 Mouse eIF4B Amino Acid Sequence (NP_663600.2)
  1    maasakkknk kgktisltdf laedggtggg styvpkpvsw adetddlegd vsttwhsndd
 61    dvyrappidr silptapraa repnidrsrl pksppytafl gnlpydvted sikdffrgln
121    isavrlprep snpdrlkgfg yaefedldsl lsalslnees lgnrriivdv adqaqdkdrd
181    drsfgrdrnr dsdktdtdwt arpttdsfdd ypprrgddsf gdkyrdryds dryrdgyrdg
241    yrdgprrdmd ryggrdrydd rgsrdydrgy dsrigsgtra fgsgyrrddd yrgggdryed
301    rydrrddrsw ssrddysrdd yrrddrgppq rprlnlkprs apkeddasaa tsqssraasi
361    fggakpvdta arereveerl qkeqeklqrq ldepkldrtp rerhpswrse etqerersrt
421    gsessqtgas atsgrntrrr eseksrlenet lnkeedchsp tskppkpdqp lkvmpapppk
481    enawvkrssn pparsqssdt eqpsptsggg kvaavqppee gpsrkdgnkv dvvgatqgqa
541    gscsrgpgdg gsrdhwkdld rkdgkkdqds rsapepkkpe enpaskfssa skyaalsvdg
601    edadegddct e SEQ ID NO: 25 Monkey eIF4B cDNA Sequence (NM_001195808.1)
  1    ctctcccaac atggcggcct cagcaaaaaa gaagaataag aaggggaaga ctatctccct
 61    aacagactt ctggctgagg atgggggtac tggtggagga agcacctatg tttccaaacc
121    agtcagctgg gccgatgaaa cggatgacct ggaaggacga gtttcacaaa cgtggcacag
181    taatgacgac gatgtgtaca gggcgcctcc aattgaccgt tccatcctc ccactgctcc
241    acgggctgct cgggaaccca atatcgaccg gagccgtctt cccaaatcgc cacctacac
301    tgcttttcta gggaacctac cctatgatgt gacagaagaa tcaattaagg aattctttag
361    aggattaaat atcagtgcag tgcgtttacc acgtgaaccc agcaatccag agaggttgaa
421    aggttttggt tatgctgaat ttgaggacct ggattccctg ctcagtgccc tgagtctcaa
481    tgaagagtct ctaggtaaca ggagaattcg agCggacgtt gctgatcaag cacaggataa
541    agacaggat gatcgttctt ttggccgtga tagaaatcgg gattctgaca aaacagatac
601    agactggagg gctcgtcctg ctacagacag ctttgatgac taccacccta gaaggaggta
661    tgatagcttt ggagacaagt atcgagatcg ttatgattca gaccggtatc gggatggta
721    Ccgggatggc ccacgccggg atatggatcg atatggtggc cgggatcgct atgatgaccg
781    aggcagcaga gactatgata gaggctatga ttcccggata ggcagtggca agagcacc
841    tggcagtggg tatcgcaggg atgatgacta cagaggaggc ggggaccgat atgaagaccg
901    atacgacaga cgggatgatc ggtcgtggag tccagagat gattactctc gggatgatta
961    taggcgcgat gacagaggtc cccctcaaag accccaactg aatctaaagc cccggagtac
1021   tcctaaggaa gatgattcct ctgctagtac ctcccagtcc agtcgagccg cctctatctt
1081   tggaggggca aagcctgttg acacagctgc tagagaaaga gaagtagaaa aacggctaca
1141   gaaggaacaa gagaagtcgc agcgtcagcc ggatgagcca aaactagacg gacggcctcg
1201   ggagagacac ccaagctggc gaagtgaaga aactcaggac cgggaacggt cgaggacagg
1261   aagtgagtca tcacagaccg ggacctccgc cacacctggc agaaatgcac gaaggagaga
1321   gagtgagaag tctctagaaa atgaaacact caataaggag gaagattgtc actctccaac
1381   ctctaaacct cccaaacctg atcagcccct aaaggtaatg ccagccctc caccaaagga
1441   gaatgcttgg gtgaagcgaa gttctaaccc tccagctcga tctcagagct cagacacaga
1501   gcagcaatcc cctacaagtg gtgggggaaa agtagctcca gctcaaccat ctgaggaagg
1561   accagcaagg aaagatgaaa ataaagtaga tgggatgaat gtcccaaaag ccaaactgg
1621   gacctctagc cgtggaccag gagacggagg gaacaaagac cactggaagg agtcagatag
1681   gaaagatggc aaaaaggatc aagactccag atctgcacct gagccaaaga aacctgagga
1741   aaatccagct tcgaagttca gttctgcaag caagtatgct gctctctctg ttgatggtga
1801   agatgaaaac gagggagaag attatgccga atagacctct acatcctgtg ctttctccta
1661   gtttctctcc accctggaac attcgagagc aaatcaaaac ctctacccag acaagacaaa
1921   ataaaactca ccatctcccg aagaccttc ttacctcttt ttaaaaacaa aaaatgaaac
1981   tatttttgca gctgctgcag cctttaaagt attaaagtaa ctggagaatc gccaatatag
2041   ccagagagaa agggactaca gcttttttaga ggaagagttg tggtgtgtta SEQ ID NO: 26 Monkey eIF4B Amino Acid Sequence (NP_001182737.1)
  1    maasakkknk kgktisltdf laedggtggg styvakpvsw adetddlegd vsttwhsndd
 61    dvyrappidr silptapraa repnidrsrl pksppytafl gnlpydvtee sikeffrgln
121    isavrlprep snperlkgfg yaefedldsl lsalalnees lgnrrirvdv adqaqdkdrd
181    drsfgrdrnr dsdktdtdwr arpatdsfdd ypprrgddsf gdkyrdryds dryrdgyrdg
241    prrdmdrygg rdryddrgsr dydrgydsri gsgrrafgsg yrrdddyrgg gdryedrydr
301    rddrswssrd dysrddyrrd drgppqrpkl nlkprstpke ddssastsqs sraasifgga
361    kpvdtaarer eveerlqkeq eklqrqldep klerrprerh pswrseetqe rersrtgses
421    sqtgtsatsg rnarrresek slenetlnke edchsptskp pkpdqplkvm papppkenaw
481    vkrssnppar sqssdteqqs ptsgggkvap aqpseegpar kdenkvdgmn vpkgqtgtss
541    rgpgdggnkd hwkesdrkdg kkdqdsrsap epkkpeenpa skfssaskya alsvdgeden
601    egedyae SEQ ID NO: 27 Cow eIF4B cDNA Sequence (NM_001035028.2)
  1    atggcggcct cagcgaaaaa gaagaataag aaggggaaga ctatctccct aacagacttt
 61    ctggctgagg atgggggac tggtggaggc agcacctatg tccccaaacc agtcagctgg
121    gctgatgaaa cagacgatct ggaaggggat gtctcaacca cttggcatag taatgatgat
181    gatgtgtatc gggcaccccc aattgaccgt tccatcctgc ccactgcccc acgggctgct
241    cgggaaccca atatcgaccg gagccgtctt cccaaatctc cacctacac tgcttttcta
301    gggaacctgc cctatgatgt gacagaagac tccattaagg aattctttag aggattaaat
361    atcagtgcag tgcgtttacc gcgtgaaccc agcaatccg agaggttaaa aggttttggt
421    tatgcagagt ttgaggacct ggattccttg ctcagtgcct tgagcctcaa cgaagagct
461    ctaggtaaca ggagaattcc agtggacgtt gctgatcaag cacaggataa agacaggat
541    gatcgctctt ttggccgaga tagaaatcgt gattctgaca aaacagatac agactggagg
601    gcccgtcctg ctgcagacag ctttgatgac taccgccca gaaggggtga tgatagcttt
661    ggagacaagt atcgagatcg ttacgattca gacagatatc gtgatgggta tcgggacagt
```

TABLE 2-continued

```
 721    taccgtgatg gcccacgccg ggacatggat cgatacgggg gccgagatcg ccatgatgac
 781    cgaggtggca gagactatga cagaggctac gattccagga taggcagtgg cagaagagca
 341    ttcggtagcg ggtaccggag ggatgatgac tacagaggag gcggggaccg ctatgaagac
 901    agatacgaca gacgagatga ccggtcctgg agttccagag atgattactc tcgggatgat
 961    cacaggcggg atgatagagg tcccccctcaa agacccaaac tgaacctaaa gcctcggagt
1021    actcctaagg aagatgattc ctccgctagc acctcccagt ccagtcgtgc agcctctatc
1081    tttggagggg caaagcctgt tgacacagct gctagagaac gagaagtaga agagcggcta
1141    cagaaggaac aggagaaact gcagcgtcag ctggatgagc caaaactaga acgacggcct
1201    cgggagagac acccaagctg gcgaagtgaa gaaactcgaa acgggaacg atcgaggaca
1261    ggaagtgagt catcacagac tgggacctca gccacacctg gcagaaatgc aagaagaaga
1321    gagagtgaga agtctttaga aaatgaaacc cccaataaag aggaagactg tcagtctcca
1381    acttctaagc cccccaaacc tgaacagcct ctaaaggtaa tgccagcccc tccaccaaag
1441    gagaatgctt gggtgaagaa aagttctaac cctcctgctc gatctcagga tcagacaca
1501    gagcagcagt cccctacaag tggtggaggg aaagtagttc cagctcaact atctgaggaa
1561    ggatcagcaa ggaaagatga aaataaagta gatggggtga gtgcccaaa aggccaaagt
1621    gggagctcca gccgtggtcc gggagatggg gggaacaaag accactggaa ggaggcagac
1681    aggaaagatg gcaaaaagga tcacgactcc agatctgcac ctgagccaaa gaaagctgaa
1741    gaaaatccag cctcgaagtt cagatctgca agcaagtacg ctactctcgc cattgacggt
1801    gaagatgaaa atgagggaga ttacaccgaa tag
```

SEQ ID NO: 28 Cow eIF4B Amino Acid Sequence (NP_001030200.1)
```
  1    maasakkknk kgktisltdf laedggtggg styvpkpvsw adetddlegd vsttwhsndd
 61    dvyrappidr silptapraa repnidrsrl pksppytafl gnlpydvted sikeffrgln
121    isavrlprep snperlkgfg yaefedldsl lsalslnees lgnrrirvdv adqaqdkdrd
181    drsfgrdrnr dsdktdtdwr arpaadsfdd ypprrgddsf gdkyrdryda dryrdgyrds
241    yrdgprrdmd ryggrdrydd rggrdydrgy dsrigsgrra fgssgyrrddd yrgggdryod
301    rydrrddrsw ssrddysrdd yrrddrgppq rpklnlkprs tpkeddaaaa tsqssraasi
361    fggakpvdta arereveerl qkeqeklqrq ldepklerrp rerhpswrse etqerersrt
421    gsessqtgts atsgrnarrr eseksleenet pnkeedcqsp tskpppkpeqp lkvmpapppk
481    enawvkrssn pparsqssdt eqqsptsggg kvvpaqlaee gsarkdenkv dgvsapkgqs
541    gsssrgpgdg gnkdhwkead rkdgkkdhds rsapepkkae enpaskfrsa skyatlaidg
601    edenegdyte
```

SEQ ID NO: 29 Rat eIF4B cDNA Sequence (NM_001008324.1)
```
  1    atggcggcct cagcaaaaaa gaagaataag aaggggaaga ccatctccct aacagacttt
 61    ctagctgagg atggggggaac tggtggagga agcacctatg tccccaaacc agtcagctgg
121    gctgacgaaa cagacgatct ggaaggagat gtgtcaacaa cttggcatag taacgatgac
181    gatgtgtaca gggcaccccc tattgaccgt tccatccttc ccactgctcc acgggctgct
241    cgggaaccca atattgatcg gagccgtctt cccaagtcac cacccctacac tgctttccta
301    gggaatctgc cctatgatgt gacagaagac tctattaagg atttctttag aggattaaat
361    atcagcgctg tacgcttgcc gcgtgagccc agcaatccag acaggttgaa aggttttggc
421    tatgccgaat ttgaggatct ggattcctctg tcagtgctc tgagtctcaa tgaagagtct
481    ctaggtaaca ggagaattcg ggtggatgtt gctgatcaag cacaggataa agacagggat
541    gaccgttcct ttggtcgaga tagaaatcgg gattctgaca gacagacac agactggagg
601    gcccgtcctg ccacagacag ctttgatgac tacccaccta gacgaggtga tgacagcttc
661    ggagacaagt atcgagatta ttacgagtca gaccggttac gggatggta tagggacgga
721    tatcgggacg gcccacgcag agacatggac cgctatgggg gccgggatcg ctatgatgac
781    cgaggcagca gagactatga ccgaggctat gactccagga taggcagtgg cagaagagca
841    tttggaagtg ggtaccggag ggatgacgac tacagaggag gtggggaccg ctatgaagat
901    cgctatgaca gacgggaca tcggtcatgg agctcaggta acgattactc tcgggacgat
961    tacaggcgtg atgacagagg tcccccccaa agacccaaac tgaatctaaa gcctcggagt
1021   actcctaaag aagatgattc ctctgctagc acctccagt ccagccgagc ggcttctatc
1081   tttggagggg cgaagcccgc tgacacagct gctagagaaa gagaagtaga ggagcggcta
1141   cagaaggagc aggagaaagct gcagcgtcag ctggatgagc caaaactaga ccgcggccc
1201   cgggagagac acccaagttg gcgaagtgaa gaaactcgaa aaagagaacg gtcgaggaca
1261   ggaagtgagt catcgcagac tgggacctca gccacatctg gcagaaaatac gaaggaga
1321   gagagtgaga agtctctaga aaatgaaacc ctcaataaag aagaagactg tcactctcca
1381   acctctaagc ctcctaaacc tgaccagcct ctaaaggtaa tgccagcccc tccaccaaag
1441   gagaatgcgt gggtgaagaa aagctctaac cctcctgctc gatctcagga tcagacaca
1501   gagcagccgt cccctacaag tggtggaggg aaagctgctc cagctcagcc ctctgaggaa
1561   ggaccatcaa ggaaagatga aactaaagtg gatggggtga gcaccaccaa aggccagact
1621   ggacactcca gccgtggtcc tggggatgga gggagcagag accactggaa ggagttggat
1681   aggaaggacg gcaaaaaaga tcaagactcc agatgcac ctgagccaaa gaaatctgag
1741   gagaaccgag cctcaagtt cagttctgca agcaagtacg ctgctctgtc tgtggacggt
1801   gaggatgagg atgagggaga cgactgcact gagtag
```

SEQ ID NO: 30 Rat eIF4B Amino Acid Sequence (NP_001008325.1)
```
  1    maasakkknk kgktisltdf laedggtggg styvpkpvsw adetddlegd vsttwhsndd
 61    dvyrappldr silptapraa repnidrsrl pksppycafl gnlpydvted sikdffrgln
121    isavrlprep snpdrlkgfg yaefedldsl lsalslnees lgnrrirvdv adqaqdkdrd
181    drsfgrdrnr dsdktdtdwr arpatdsfdd ypprrgddsf gdkyrdryes dryrdgyrdg
241    yrdgprrdmd ryggrdrydd rgsrdydrgy dsrigsgrra fgssgyrrddd yrgggdryed
301    rydrrddrsw ssrddysrdd yrrddrgppq rpklnlkprs tpkeddssas tsqssraasi
361    fggakpvdta arereveerl qkeqeklqrq ldepkldrrp rerhpswrse etqeretsrt
421    gsessqtgts atsgrntrrr eseksleenet lnkeedchsp tskppkpdqp lkvmpapppk
481    enawvkrssn pparsqssdt eqpsptsggg kvapaqpsee gpsckdetkv dgvsttkgqt
541    ghssrgpgdg gsrdhwkeld rkdgkkdqds rsapepkkse enraskfssa skyaalsvdg
601    ededegddct e
```

Included in Table 2 are nucleic acid molecules comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with a nucleic acid sequence of any SEQ ID NO listed in Table 2. Such nucleic acid molecules can encode a polypeptide having a function of the full-length polypeptide as described further herein.

Included in Table 2 are polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 2. Such polypeptides can have a function of the full-length polypeptide as described further herein.

II. Subjects

In one embodiment, the subject for whom predicted likelihood of efficacy of an anti-cancer therapy (e.g., PI3K-mTORC1-S6K1 signaling pathway inhibitor therapy) is determined, is a mammal (e.g., mouse, rat, primate, non-human mammal, domestic animal such as dog, cat, cow, horse), and is preferably a human.

In another embodiment of the methods of the invention, the subject has not undergone treatment, such as chemotherapy, radiation therapy, targeted therapy, and/or anti-cancer therapy (e.g., PI3K-mTORC1-S6K1 signaling pathway inhibitor therapy). In still another embodiment, the subject has undergone treatment, such as chemotherapy, radiation therapy, targeted therapy, and/or anti-cancer therapy (e.g., PI3K-mTORC1-S6K1 signaling pathway inhibitor therapy).

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the invention can be used to determine the responsiveness to anti-cancer therapy (e.g., PI3K-mTORC1-S6K1 signaling pathway inhibitor therapy) of many different c-MYC-dependent cancers in subjects such as those described above. In one embodiment, the caucus are hematologic cancers, such as leukemia. In another embodiment, the cancers are solid tumors, such as lung, cancer, melanoma, and/or renal cell carcinoma. In another embodiment, the cancer is an epithelial cancer such as, but not limited to, brain cancer (e.g., glioblastomas) bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer.

III. Sample Collection, Preparation and Separation

In some embodiments, biomarker presence, absence, amount, and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples such as the normal copy number, amount, or activity of at biomarker in the cell or tissue type of a member of the same species as from which the test sample was obtained or a non-diseased cell or tissue from the subject from which the test samples was obtained. As described herein, a "pre-determined" biomarker amount and/or activity measurement(s) may be a biomarker amount and/or activity measurement(s) used to, by way of example only, evaluate a subject that may be selected for treatment, evaluate a response to an anti-cancer therapy (e.g., PI3K-mTORC1-S6K1 signaling pathway inhibitor therapy), and/or evaluate a response to a combination anti-cancer therapy (e.g., PI3K-mTORC1-S6K1 signaling pathway inhibitor therapy plus immunoinhibitory inhibitor therapy). A pre-determined biomarker amount and/or activity measurement(s) may be determined in populations of patients with or without cancer. The pre-determined biomarker amount and/or activity measurements) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., biomarker expression normalized to the expression of a housekeeping gene, or gene expression at various time-points).

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.5 fold, about 1.0 fold, about 1.5 fold, about 2.0 fold, about 2.5 fold, about 3.0 fold, about 3.5 fold, about 4.0 fold, about 4.5 fold, or about 5.0 fold or greater. In some embodiments, the fold change is less than about 1, less than about 5, less than about 10, less than about 20, less than about 30, less than about 40, or less than about 50. In other embodiments, the fold change in biomarker amount and/or activity measurement(s) compared to a predetermined level is more than about 1 more than about 5, more than about 10, more than about 20, more than about 30, more than about 40, or more than about 50.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject, and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermeable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermable membrane based on size and charge, it renders electrodialysis useful for concentration, removal, or separation of electrolytes.

Separation and purification in the present invention may include any procedure known in the art, such as capillary electrophoresis (e.g., capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

IV. Biomarker Nucleic Acids and Polypeptides

One aspect of the present invention pertains to the use of isolated nucleic acid molecules that correspond to biomarker nucleic acids that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual,* 2nd ed., Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

Moreover, a nucleic acid molecule of the invention can comprise only a portion of a nucleic acid sequence, wherein the full length nucleic acid sequence comprises a marker of the invention or which encodes a polypeptide corresponding to a marker of the invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of the invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or pardons thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having, one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than 1/100 or 1/1000 members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site, SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals.

Any and all such nucleotide variations and resulting amino acid polymorphisms or variations that are the result of natural allelic variation and that do not alter the functional activity are intended to be within the scope of the invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the invention or to a nucleic acid molecule encoding a protein corresponding to a marker of the invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from the naturally-occurring proteins which correspond to the markers of the invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine methionine, tryptophan), beta-branched side chains (e.g., threonine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments the present invention further contemplates the use of anti-biomarker antisense nucleic acid molecules, i.e., molecules which are complementary to a sense nucleic acid of the invention, e.g., complementary to the coding strand of a double-stranded cDNA molecule corresponding to a marker of the invention or complementary to an mRNA sequence corresponding to a marker of the invention. Accordingly, an antisense nucleic acid molecule of the invention can hydrogen bond to (i.e. anneal with) a sense nucleic acid of the invention. The antisense nucleic acid can be complementary to an entire coding strand, or to only a portion thereof, e.g., all or part of the proem coding region (or open reading frame). An antisense nucleic acid molecule can also be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a polypeptide corresponding to a selected marker or the invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res* 15:6625-6641). The antisense nucleic acid molecule can also comprise a 2'-o-methylribonucleotide (Inoue et al., 1987, *Nucleic Acids Res*, 15:6131-6148) or a chimeric RNA-DNA analogue (Inoue et al., 1987, *FEBS Lett.* 215:327-330).

The present invention also encompasses ribozymes. Ribozymes are catalytic RNA molecules with ribonuclease activity which are capable of cleaving a single-stranded nucleic acid, such as, an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the invention can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the invention can be used to select a catalytic RNA having a specific ribonuclease activity from a pool of RNA molecules (see, e.g., Bartel and Szostak, 1993, *Science* 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, *Bioorganic & Medicinal Chemistry* 4(1); 5-23). As used herein, the terms "peptide nucleic acids" or "PNAs" refer to nucleic acid mimic, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect of the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the invention are produced by recombinant DNA techniques. Alternative to recombinant expression, a polypeptide corresponding, to a marker of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 88%, 90%, 91%, 92%, 94%, 95%, 96%, 97%, 98%, or 99%) to one of these sequences and retain the functional activity or the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequence's is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes. Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See the National Center for Biotechnology Information (NCBI) website at ncbi.nlm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins corresponding to a biomarker protein. As used herein, a "chimeric protein" or "fusion protein" comprises all or part (preferably a biologically active part) of a polypeptide corresponding to a marker of the invention operably linked to a heterologous polypeptide (i.e., a polypeptide other than the polypeptide corresponding to the marker). Within the fusion protein, the term "operably linked" is intended to indicate that the polypeptide of the invention and the heterologous polypeptide are fused in-frame to each other. The heterologous polypeptide can be fused to the amino-terminus or the carboxyl-terminus of the polypeptide of the invention.

One useful fusion protein is a GST fusion protein in which a polypeptide corresponding to a marker of the invention is fused to the carboxyl terminus of GST sequences. Such fusion proteins can facilitate the purification of a recombinant polypeptide of the invention.

In another embodiment, the fusion protein contains a heterologous signal sequence, immunoglobulin fusion protein, toxin, or other useful protein sequence. Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing, sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see e.g., Narang, 1983, *Tetrahedron* 39:3; Itakura et al., 1984, *Annu. Rev. Biochem.* 53:323; Itakura et al., 1984, *Science* 198: 1056; Ike et al., 1983 *Nucleic Acid Res.* 11:477).

In addition, libraries of fragments of the coding sequence of a polypeptide corresponding to a marker of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, *Proc. Natl. Acad. Sci. USA* 89:7811-7815; Delgrave et al., 1993, *Protein Engineering* 6(3):327-331).

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Express ion Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors fir use in the invention can be designed for expression of a polypeptide corresponding to a marker of the invention in prokaryotic (e.g., *E. coli*) eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia. Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., 60-89, In *Gene Expression Technology: Methods in Enzymology* vol. 185, Academic Press, San Diego, Calif., 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the present invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1(1)).

Another aspect of the present invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

V. Analyzing Biomarker Nucleic Acids and Polypeptides

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number and/or Genomic Nucleic Acid Mutations

Methods of evaluating the copy number and/or genomic nucleic acid status (e.g., mutations) of a biomarker nucleic acid are well known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. The absence of at least one biomarker listed in Table 1 is predictive of poorer outcome of PI3K-mTORC1-S6K1 signaling pathway inhibitor therapy. A copy number of at least 3, 4, 5, 6, 7, 8, 9, or 10 of at least one biomarker listed in Table 1 is predictive of likely responsive to PI3K-mTORC1-S6K1 signaling pathway inhibitor therapy. A copy number of at least 3, 4, 5, 6, 7, 8, 9, or 10 of at least one biomarker listed in Table 2 is predictive of poorer outcome of anti-cancer therapy (e.g., PI3K-mTORC1-S6K1 signaling pathway inhibitor therapy).

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well known in the art (see, e.g., U.S. Pat. Nos. 6,335,167; 6,197,501; 5,830,645; and 5,665,549 and Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR)). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Biomarker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) *Science* 278: 1481; Emmert-Buck et al. (1996) *Science* 274:998; Fend et al. (1999) *Am. J. Path.* 154: 61 and Murakami et al. (2000) *Kidney Int.* 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) *Curr. Top. Dev. Biol.* 36, 245 and Jena et al. (1996) *J. Immunol. Methods* 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, N.Y.).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) *PNAS* 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well known in the art (see, e.g., U.S. Pat. Nos. 6,618,6796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}$P and $^{35}$S. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to an anti-cancer therapy (e.g., PI3K-mTORC1-S6K1 signaling pathway inhibitor therapy). Any method known in the art for detecting polypeptides can be used. Such methods include, but are not limited to, immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired biomarker protein standard is labeled (with a radioisotope such as $^{125}$I or $^{35}$S, or an assayable enzyme, such as horseradish peroxidase or alkaline phosphatase), and, together with the unlabelled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker protein antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as to not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et al., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I, $^{121}$I), carbon ($^{14}$C), sulphur ($^{35}$S), tritium ($^{3}$H), indium ($^{112}$In), and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the subject, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$ M, $10^{-7}$ M, $10^{-8}$ M, $10^{-9}$ M, $10^{-10}$ M, $10^{-11}$ M, or $10^{-12}$ M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify c-MYC 5' UTR sequences that regulate c-MYC translation.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) *Proc. Natl. Acad. Sci. USA* 74:560 or Sanger (1977) *Proc. Natl. Acad Sci. USA* 74:5463. It is also contemplated that any of a variety of automated sequencing procedures can be utilized when performing the diagnostic assays (Naeve (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a biomarker gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc Natl. Acad. Sci USA* 86:2766; see also Cotton (1993) *Mutat. Res.* 285:125-144 and Hayashi (1992) *Genet. Anal. Tech. Appl.* 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

3. Anti-Cancer Therapies

The efficacy of anti-cancer therapy (e.g., PI3K-mTORC1-S6K1 signaling pathway inhibitor therapy) is predicted according to biomarker presence, absence, amount and/or activity associated with a cancer (e.g., c-MYC-dependent cancer) in a subject according to the methods described herein. In one embodiment, such anti-cancer therapy (e.g., PI3K-mTORC1-S6K1 signaling pathway inhibitor therapy) or combinations of therapies (e.g., anti-PD-1 and anti-immunoinhibitory therapies) can be administered once a subject is indicated as being a likely responder to anti-cancer therapy (e.g., PI3K-mTORC1-S6K1 signaling pathway inhibitor therapy). In another embodiment, such anti-cancer therapy (e.g., PI3K-mTORC1-S6K1 signaling pathway inhibitor therapy) can be avoided once a subject is indicated as not being a likely responder to the anti-cancer therapy (e.g., PI3K-mTORC1-S6K1 signaling pathway inhibitor therapy) and an alternative treatment regimen, such as targeted and/or untargeted anti-cancer therapies can be administered. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with or without anti-cancer therapy (e.g., PI3K-mTORC1-S6K1 signaling pathway inhibitor therapy).

The PI3K-mTORC1-S6K1 signaling pathway and exemplary agents useful for inhibiting the PI3K-mTORC1-S6K1 signaling pathway, or other biomarkers described herein, have been described above.

The term "targeted therapy" refers to administration of agents that selectively interact with a chosen biomolecule to thereby treat cancer. For example, targeted therapy regarding the inhibition of immune checkpoint inhibitor is useful in combination with the methods of the present invention. The term "immune checkpoint inhibitor" means a group of molecules on the cell surface of CD4+ and/or CD8+ T cells that fine-tune immune responses by down-modulating or inhibiting an anti-tumor immune response. Immune checkpoint proteins are well known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR (see, for example, WO 2012/177624). Inhibition of one or more immune checkpoint inhibitors can block or otherwise neutralize inhibitory signaling to thereby upregulate an immune response in order to more efficaciously treat cancer.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). For example, anti-VEGF and mTOR inhibitors are known to be effective in treating renal cell carcinoma. Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with anti-cancer therapy (e.g., PI3K-mTORC1-S6K1 signaling pathway inhibitor therapy) may vary according to the particular anti-immune checkpoint inhibitor agent or combination thereof. An appropriate treatment time for a particular cancer therapeutic agent will be appreciated by the skilled artisan. The invention contemplates the continued assessment of optimal treatment schedules for each cancer therapeutic agent, where the phenotype of the cancer of the subject as determined by the methods of the invention is a factor in determining optimal treatment doses and schedules.

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Feigner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Feigner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth;

Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

4. Clinical Efficacy

Clinical efficacy can be measured by any method known in the art. For example, the response to an anti-cancer therapy (e.g., PI3K-mTORC1-S6K1 signaling pathway inhibitor therapy), relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol.* (2007) 25:4414-4422) or Miller-Payne score (Ogston et al., (2003) *Breast* (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular anti-immune checkpoint inhibitor therapeutic regimen is at least 25%, 30%, 35%, 40%, 45%, 50%, 55%, 60%, 65%, 70%, 75%, 80%, 85%, or more.

Additional criteria for evaluating the response to anti-cancer therapy (e.g., PI3K-mTORC1-S6K1 signaling pathway inhibitor therapy) are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-immune checkpoint inhibitor therapeutic regimen can be administered to a population of subjects and the outcome can be correlated to biomarker measurements that were determined prior to administration of any anti-cancer therapy (e.g., PI3K-mTORC1-S6K1 signaling pathway inhibitor therapy). The outcome measurement may be pathologic response to therapy given in the neoadjuvant setting. Alternatively, outcome measures, such as overall survival and disease-free survival can be monitored over a period of time for subjects following anti-cancer therapy (e.g., PI3K-mTORC1-S6K1 signaling pathway inhibitor therapy) for whom biomarker measurement values are known. In certain embodiments, the same doses of anti-immune checkpoint inhibitor agents are administered to each subject. In related embodiments, the doses administered are standard doses known in the art for anti-immune checkpoint inhibitor agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an anti-cancer therapy (e.g., PI3K-mTORC1-S6K1 signaling pathway inhibitor therapy) can be determined using methods such as those described in the Examples section.

5. Further Uses and Methods of the Present Invention

The compositions described herein can be used in a variety of diagnostic, prognostic, and therapeutic applications regarding biomarkers described herein, such as those listed in Table 1 or 2.

a. Screening Methods

One aspect of the present invention relates to screening assays, including non-cell based assays. In one embodiment, the assays provide a method for identifying whether a cancer is likely to respond to anti-cancer therapy (e.g., PI3K-mTORC1-S6K1 signaling pathway inhibitor therapy) and/or whether an agent can inhibit the growth of or kill a cancer cell that is unlikely to respond to anti-cancer therapy (e.g., PI3K-mTORC1-S6K1 signaling pathway inhibitor therapy).

In one embodiment, the invention relates to assays for screening test agents which bind to, or modulate the biological activity of, at least one biomarker listed in Table 1 or 2. In one embodiment, a method for identifying such an agent entails determining the ability of the agent to modulate, e.g. inhibit, the at least one biomarker listed in Table 1 or 2.

In one embodiment, an assay is a cell-free or cell-based assay, comprising contacting at least one biomarker listed in Table 1 or 2, with a test agent, and determining the ability of the test agent to modulate (e.g. inhibit) the enzymatic activity of the biomarker, such as by measuring direct binding of substrates or by measuring indirect parameters as described below.

In another embodiment, an assay is a cell-free or cell-based assay, comprising contacting at least one biomarker listed in Table 1 or 2, with a test agent, and determining the ability of the test agent to modulate the ability of the biomarker to regulate translation of c-MYC, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}I$, $^{35}S$, $^{14}C$, or $^{3}H$, either directly or indirectly, and the radioisotope detected by direct counting of radioemmission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies of the present invention can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and its natural binding partner can be accomplished by determining the ability of the test agent to modulate the activity of a polypeptide or other product that functions downstream or upstream of its position within the PI3K-mTORC1-S6K1 signaling pathway.

The present invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the presence, absence, amount, and/or activity level of a biomarker described herein, such as those listed in Table 1 or 2, in the context of a biological sample (e.g., blood, serum, cells, or tissue) to thereby determine whether an individual afflicted with a cancer is likely to respond to anti-cancer therapy (e.g., PI3K-mTORC1-S6K1 signaling pathway inhibitor therapy), whether in an original or recurrent cancer. Such assays can be used for prognostic or predictive purpose to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers described herein, such as those listed in Table 1 or 2.

Another aspect of the present invention pertains to monitoring the influence of agents (e.g., drugs, compounds, and small nucleic acid-based molecules) on the expression or activity of a biomarker listed in Table 1 or 2. These and other agents are described in further detail in the following sections.

The skilled artisan will also appreciate that, in certain embodiments, the methods of the present invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with a cancer that is likely to respond to anti-cancer therapy (e.g., PI3K-mTORC1-S6K1 signaling pathway inhibitor therapy). In some embodiments, the present invention is useful for classifying a sample (e.g., from a subject) as associated with or at risk for responding to or not responding to anti-cancer therapy (e.g., PI3K-mTORC1-S6K1 signaling pathway inhibitor therapy) using a statistical algorithm and/or empirical data (e.g., the amount or activity of a biomarker listed in Table 1 or 2).

An exemplary method for detecting the amount or activity of a biomarker listed in Table 1 or 2, and thus useful for classifying whether a sample is likely or unlikely to respond to anti-cancer therapy (e.g., PI3K-mTORC1-S6K1 signaling pathway inhibitor therapy) involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely anti-cancer therapy (e.g., PI3K-mTORC1-S6K1 signaling pathway inhibitor therapy) responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptions such as multi-layer perceptions, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to anti-cancer therapy (e.g., PI3K-mTORC1-S6K1 signaling pathway inhibitor therapy), a biological sample from the subject during remission, or a biological sample from the subject during treatment for developing a cancer progressing despite anti-cancer therapy (e.g., PI3K-mTORC1-S6K1 signaling pathway inhibitor therapy).

d. Prognostic Assays

The diagnostic methods described herein can furthermore be utilized to identify subjects having or at risk of developing a cancer that is likely or unlikely to be responsive to anti-cancer therapy (e.g., PI3K-mTORC1-S6K1 signaling pathway inhibitor therapy). The assays described herein, such as the preceding diagnostic assays or the following assays, can be utilized to identify a subject having or at risk of developing a disorder associated with a misregulation of the amount or activity of at least one biomarker described in Table 1, such as in cancer. Alternatively, the prognostic assays can be utilized to identify a subject having or at risk for developing a disorder associated with a misregulation of the at least one biomarker described in Table 1, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

Another aspect of the invention pertains to methods of modulating the expression or activity of one or more biomarkers described herein (e.g., those listed in Tables 1 or 2 and the Examples or fragments thereof) for therapeutic purposes. The biomarkers of the present invention have been demonstrated to correlate with c-MYC-dependent cancers. Accordingly, the activity and/or expression of the biomarker, as well as the interaction between one or more biomarkers or a fragment thereof and its natural binding partner(s) or a fragment(s) thereof, can be modulated in order to treat c-MYC-dependent cancers.

Modulatory methods of the invention involve contacting a cell with one or more biomarkers of the invention, including one or more biomarkers of the invention, including one or more biomarkers listed in Table 1 or 2 and the Examples or a fragment thereof or agent that modulates one or more of the activities of biomarker activity associated with the cell. An agent that modulates biomarker activity can be an agent as described herein, such as a nucleic acid or a polypeptide, a naturally-occurring binding partner of the biomarker, an antibody against the biomarker, a combination of antibodies against the biomarker and antibodies against other immune related targets, one or more biomarkers agonist or antagonist, a peptidomimetic of one or more biomarkers agonist or antagonist, one or more biomarkers peptidomimetic, other small molecule, or small RNA directed against or a mimic of one or more biomarkers nucleic acid gene expression product.

An agent that modulates the expression of one or more biomarkers of the present invention, including one or more biomarkers of the invention, including one or more biomarkers listed in Table 1 or 2 and the Examples or a fragment thereof is, e.g., an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule, triplex oligonucleotide, ribozyme, or recombinant vector for expression of one or more biomarkers polypeptide. For example, an oligonucleotide complementary to the area around one or more biomarkers polypeptide translation initiation site can be synthesized. One or more antisense oligonucleotides can be added to cell media, typically at 200 µg/ml, or administered to a patient to prevent the synthesis of one or more biomarkers polypeptide. The antisense oligonucleotide is taken up by cells and hybridizes to one or more biomarkers mRNA to prevent translation. Alternatively, an oligonucleotide which binds double-stranded DNA to form a triplex construct to prevent DNA unwinding and transcription can be used. As a result of either, synthesis of biomarker polypeptide is blocked. When biomarker expression is modulated, preferably, such modulation occurs by a means other than by knocking out the biomarker gene.

Agents which modulate expression, by virtue of the fact that they control the amount of biomarker in a cell, also modulate the total amount of biomarker activity in a cell.

In one embodiment, the agent stimulates one or more activities of one or more biomarkers of the invention, including one or more biomarkers listed in Table 1 or 2 and the Examples or a fragment thereof (e.g., enhancing the activity or structure of a c-MYC 5' UTR in order to enhance the regulation of c-MYC translation). Examples of such stimulatory agents include active biomarker polypeptide or a fragment thereof and a nucleic acid molecule encoding the biomarker or a fragment thereof that has been introduced into the cell (e.g., cDNA, mRNA, shRNAs, siRNAs, small RNAs, mature miRNA, pre-miRNA, pri-miRNA, miRNA*, anti-miRNA, or a miRNA binding site, or a variant thereof, or other functionally equivalent molecule known to a skilled artisan). In another embodiment, the agent inhibits one or more biomarker activities. In one embodiment, the agent inhibits or enhances the interaction of the biomarker with its natural binding partner(s). Examples of such inhibitory agents include antisense nucleic acid molecules, anti-biomarker antibodies, biomarker inhibitors, and compounds identified in the screening assays described herein.

These modulatory methods can be performed in vitro (e.g., by contacting the cell with the agent) or, alternatively, by contacting an agent with cells in vivo (e.g., by administering the agent to a subject). As such, the present invention provides methods of treating an individual afflicted with a condition or disorder that would benefit from up- or down-modulation of one or more biomarkers of the present invention listed in Table 1 or 2 and the Examples or a fragment thereof, e.g., a disorder characterized by unwanted, insufficient, or aberrant expression or activity of the biomarker or fragments thereof. In one embodiment, the method involves administering an agent (e.g., an agent identified by a screening assay described herein), or combination of agents that modulates (e.g., upregulates or downregulates) biomarker expression or activity. In another embodiment, the method involves administering one or more biomarkers polypeptide or nucleic acid molecule as therapy to compensate for reduced, aberrant, or unwanted biomarker expression or activity.

Stimulation of biomarker activity is desirable in situations in which the biomarker is abnormally downregulated and/or in which increased biomarker activity is likely to have a beneficial effect. Likewise, inhibition of biomarker activity is desirable in situations in which biomarker is abnormally upregulated and/or in which decreased biomarker activity is likely to have a beneficial effect.

In addition, these modulatory agents can also be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy (e.g., standard-of-care treatments for cancer well known to the skilled artisan), either consecutively with, pre- or post-conventional therapy. For example, these modulatory agents can be administered with a therapeutically effective dose of chemotherapeutic agent. In another embodiment, these modulatory agents are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular melanoma, being treated, the extent of the disease and other factors familiar to the physician of skill in the art and can be determined by the physician.

6. Pharmaceutical Compositions

In another aspect, the present invention provides pharmaceutically acceptable compositions which comprise a therapeutically-effective amount of an agent that modulates (e.g., decreases) biomarker expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression. These salts can likewise be prepared in situ during the final isolation and purification of the respiration uncoupling agents, or by separately reacting the purified respiration uncoupling agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a respiration uncoupling agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a respiration uncoupling agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more respiration uncoupling agents in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the respiration uncoupling agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

Other embodiments of the present invention are described in the following Examples. The present invention is further illustrated by the following examples which should not be construed as further limiting.

EXAMPLES

Example 1

Materials and Methods for Examples 2-7 a. Mice

LckCre (Hennet et al. (1995) *Proc. Natl. Acad. Sci. U.S.A.* 92:12070-12074) and Pten$^{f/f}$ (Lesche et al. (2002) *Genesis* 32:148-149) mice were crossed to generate experimental mice for this study. All animals were housed and treated in accordance with protocols approved by the Institutional Animal Care and Use Committees at Dana-Farber Cancer Institute and Harvard Medical School.

b. Cell Lines and Cell Culture

Hematological cancer cell lines were cultured in RPMI (Life Technologies) supplemented with 10% FBS (Life Technologies) and 1% Pen/Strep (Life Technologies). CAMA1 and T47D were cultured in DMEM (Life Technologies) supplemented with 10% FBS and 1% Pen/Strep. Primary cell lines were established from isolated thymocytes of moribund LckCre$^+$/Pten$^{f/f}$ mice and cultured in RPMI supplemented with 10% FBS and 1% Pen/Strep.

c. Chemicals

The following small molecule inhibitors were used in the studies described herein: BEZ235 (Maira et al. (2008) *Mol. Cancer Ther.* 7:1851-1863), BKM120 (Elfiky et al. (2011) *J. Transl. Med.* 9:133), MK2206 (Chandarlapaty et al. (2011) *Cancer Cell* 19:58-71), RAD001 (Schuler et al. (1997) *Transplantation* 64:36-42) and hippuristanol (Bordeleau et al. (2006) *Nat. Chem. Biol.* 2:213-220). The remaining chemical reagents were purchased from the indicated source: PF4708671 (Sigma), Lipofectamine 2000 (Sigma), MG132 (Sigma), Cycloheximide (Sigma), puromycin (Sigma), protease inhibitor tablets (Roche), and phosphates inhibitor tablets (Roche).

d. Western Blotting

Cells were washed with cold PBS and then lysed in 1% Nonidet P-40 lysis buffer supplemented with protease and phosphatase inhibitors. 15 μg of whole cell lysates were resolved by SDS-PAGE followed by transfer onto nitrocellulose membrane (Bio-Rad). Membranes were blocked and incubated with primary antibodies overnight. Immunofluorescently labeled anti-mouse IgG (Rockland Immunochemicals) and anti-rabbit IgG (Molecular Probes) were used to develop band intensities in the Odyssey system (Li-Cor). Quantification of band intensities was performed using Odyssey 3.0 software. The primary antibodies used for Western blotting in the studies described herein were purchased from Cell Signaling Technology, unless otherwise noted: c-Myc, Pten, p-AKT (S473), p-S6RP (S235/236), eIF4A, eIF4B, Actin (Milipore), and α-Tubulin (Sigma-Aldrich).

e. shRNA Constructs and Lenti-Viral Infection shRNAs constructs were purchased from the RNAi Consortium of the Broad Institute. Construct sequences are described in Table 2 below. To produce lenti-viruses, 293T cells were co-transfected with shRNA constructs, Vsv-g and ΔR89 using Lipofectamine 2000 at the ratio of 5:1:4. Viruses were collected on days 2 and 3 post transfection and one million cells were infected with 1 ml virus. Forty-eight hours post infection, cells were selected with puromycin at 2 μg/ml for two days and then maintained in puromycin at 2.5 μg/ml.

TABLE 3 shRNA constructs of human eIF4A and eIF4B

| Construct | TRC ID | Targeting Sequence |
|---|---|---|
| sh-eIF4A #1 | TRCN0000052193 | GCCGTGTGTTTGATATGCTTA |
| sh-eIF4A #2 | TRCN0000052194 | GCCGTAAAGGTGTGGCTATTA |
| sh-eIF4A #3 | TRCN0000052195 | CCTTGTATCAAGGGTTATGAT |
| sh-eIF4A #4 | TRCN0000052196 | CGAAATGTTAAGCCGTGGATT |
| sh-eIF4A #5 | TRCN0000052197 | GCAGCAGGTTTCTTTAGTCAT |
| sh-eIF4B #1 | TRCN0000062598 | GCGGAGAAACACCTTGATCTT |
| sh-eIF4B #2 | TRCN0000062599 | GCCGTGATAGAAATCGGGATT |
| sh-eIF4B #3 | TRCN0000062600 | CCAACTTCTAAACCTCCCAAA |
| sh-eIF4B #4 | TRCN0000062602 | CTACCCTATGATGTTACAGAA |
| sh-eIF4B #5 | TRCN0000062601 | CGGGATGATTATAGGCGTGAT | f. De Deno Synthesis Assay of c-MYC Protein

Cells were pre-treated with 25 μg/ml cycloheximide (CHX) for two hours to deplete c-MYC protein and then washed three times with phosphate-buffered saline (PBS) to allow new biosynthesis. MG132 was then added at 10 μM either alone or with 25 μg/ml CHX, or with inhibitors for one hour to two hours.

g. Retroviral Infections and FACS Sorting

The MigR1-MYC T58A construct available from the Abramson Family Cancer Research Institute was used. Human MYC 5'UTR sequence was obtained from NCBI and subcloned into the MigR1-MYC T58A construct. Primer sequences are as follows: forward, 5'-ACCCCCGAGCTGTGCTGCTCG-3' and reverse 5'-CGTCGCGGGAGGCTGCTGGTT-3'. pCMV-PTEN was purchased from Addgene and subcloned into the MigR1 vector. With Lipofectamine 2000 (Life Technologies), retroviruses were generated by co-transfecting 293T cells with MigR1-based plasmids, Vsv-g and Gag at the ratio of 5:1:4. Viruses were collected on days 2 and 3 post-transfection and applied to cells. Seventy-two hours post-infection, GFP-positive cells were sorted using BD FACSAria® IIu followed by inhibitor treatments or Western blotting analysis.

h. Histology, IHC, Wright-Giemsa Staining and White Blood Cell Count

For histology analysis, primary tissues were isolated, fixed with 10% buffered formalin, embedded in paraffin, sectioned, and stained with hematoxylin and eosin by the Dana Farber/Harvard Cancer Center Rodent Histopathology Core. For IHC, fixed sections were dewaxed and rehydrated, boiled in citrate buffer and then blocked. Antibodies were incubated overnight, and positive nuclei were detected by diaminobenzidine (Sigma). Sections were then counterstained with Mayer's hematoxylin. Antibodies used for IHC were Ki67 (Vector Laboratories), p-Akt (S473) (Cell Signaling) and p-S6RP (S235/S236) (Cell Signaling). For Wright-giemsa staining, cytospin slides (Thermo Scientific) with primary mouse bone marrow cells and peripheral blood smear slides were stained according to routine methods (Lillie (1944) *Am. J. Pathol.* 20:291-296) using Wright-giemsa stain (Electron Microscopy Sciences). Mouse peripheral white blood cell counts were measured using HEMAVET Multispecies Hematology Analyzer (Drew Scientific).

i. Quantitative PCR

Total RNA was extracted from cells using TRIzol® reagent (Life Technologies). cDNAs were reverse-transcribed using the SuperScript III first strand synthesis kit (Invitrogen) and subsequently utilized for quantitative PCR with SYBR Green Master Mix (Applied Biosystems). Analysis was performed on triplicate PCR data for each biological duplicate and normalized to GAPDH. Primer sequences are as follows: MYC forward, 5'-CTACCCTCT-CAACGACAGCA-3' and reverse 5'-AGAGCAGAGAATCCGAGGAC-3'; Myc forward, 5'-GTGCTGCATGAGGAGACACC-3' and reverse 5'-TTTGCCTCTTCTCCACAGACA-3'.

j. In Vivo Xenograft and Inhibitor Administration

Five to six week old female C57 Bl/6 recipient mice were purchased from Jackson Laboratory. A total of two million thymocytes isolated from moribund LckCre$^+$/Pten$^{f/f}$ mice were injected retro-orbitally into sub-lethally irradiated recipients. Five to six week old NOG mice were purchased from Jackson Laboratory. A total of two million primary human patient D115 or D135 cells or HPB-ALL human cell line cells were injected into the recipients via tail-vein injection. For in vivo BEZ235/BKM120 treatment, BEZ235/BKM120 was dissolved into one volume of NMP (Sigma) and nine volumes of PEG300 (Fluka Analytical) and then gavaged at 35 mg/kg mouse daily (Maira et al. (2008) *Mol. Cancer Ther.* 7:1851-1863), starting two weeks following transplantation. Studies were performed under the auspices of protocols approved by the Institutional Animal Care and Use Committees at Dana-Farber Cancer Institute and Harvard Medical School.

k. Polysome Profiles and RNA Extraction

Polysome profiles and RNA extractions were performed as described in Lee et al. (2013). Briefly, following drug treatment, cells were incubated with 100 µg/ml cyclohexamide at 37° C. for 15 minutes and then washed twice in cold PBS with 100 µg/ml cyclohexamide. Cells were lysed in 10 mM Tris pH 7.4, 10 mM NaCl, 5 mM $MgCl_2$, 100 µg/mL cyclohexamide, 0.5% (v/v) Triton-X, 1.0% (v/v) Tween-20, and 0.5% (v/v) sodium deoxycholate and passed 5× through a 21 gauge needle. Cytoplasmic extracts were clarified by centrifugation at 10,000×g for 10 minutes at 4° C. and loaded onto 10-50% (w/v) sucrose gradients (10 mM Tris pH 7.4, 0.3M NaCl, 15 mM $MgCl_2$, 100 µg/ml cyclohexamide). Lysates were centrifuged at 160,030×g for 2.5 hours at 4° C. in a Beckman Coulter SW41Ti rotor. Fractions were collected using a BioRad BioLogic LP, and absorbance was monitored at UV 254. RNA was isolated from fractions by acid phenol/chloroform extraction and ethanol precipitation, and treated with RQ1 DNAse (Promega) prior to a second extraction and precipitation. RNA was re-suspended in $H_2O$ and reverse transcribed using SuperScript® III reverse transcriptase (Life Technologies) for quantitative PCR analysis.

l. Cell Proliferation Assay

Hematological cancer cell lines were seeded onto 96-well plates at a density of 15,000 cells/well in 100 µl media. CAMA1 and T47D were seeded at 4,000 cells/well in 100 µl media and then drugs dissolved in DMSO or DMSO control was added. After seventy-two hours of incubation, cells were analyzed for cell viability by the addition of 20 µl/well MTS reagent (Promega). After three hours incubation at 37° C., the signal from the viable cells was determined by measuring the absorbance at 490 nM on a microplate spectrophotometer (Bio-Rad). IC50s were calculated using Prism6 (GraphPad).

m. Luciferase Assay pGL3-+5'UTR was constructed via inserting the human MYC 5'UTR sequence into the pGL3-Basic (−5'UTR) (Promega) firefly luciferase reporter vector. Cells were co-transfected with pGL3 or pGL3-+5'UTR together with the pRL renilla luciferase reporter vector (Promega) as internal control at the ratio of 10:1. Forty-eight hours post transfection, inhibitors were added to cells for four hours and luciferase activities were measured with Dual-Luciferase® Reporter Assay System (Promega) and detected using Lumat LB 9507 (EG&G Berthold).

n. Statistics

Kaplan-Meier survival curves were constructed using Prism6 (GraphPad), and log-rank analysis was used to analyze the results. An unpaired, 2-tail student t-test was used to compute P values.

Example 2

Pten-Null Driven T-ALL with Over-Expressed c-Myc is Sensitive to PI3K/AKT Inhibition To identify novel regulatory mechanisms governing expression of the c-Myc oncoprotein that could potentially be clinically relevant, a murine T cell tumor model that is initiated by loss of Pten (Hagenbeek and Spits (2008) *Leukemia* 22:608-619) was used. PTEN is a critical tumor suppressor functioning as the antagonist of PI3K signaling, and its inactivation results in hyperactivation of the serine/threonine kinase AKT, which in turn triggers multiple signaling pathways to regulate cell growth, survival, and metabolism (Engelman (2009) *Nat. Rev. Cancer* 9:550-562). Notably, several T cell tumor models initiated by Pten-loss have been reported to almost invariably feature c-Myc overexpression (Guo et al. (2008) *Nature* 453:529-533; Liu et al. (2010) *J. Clin. Invest.* 120:2497-2507; and Zhang et al. (2011) *Leukemia* 25:1857-1868). The resulting disease closely resembles its human counterparts that also frequently feature PTEN loss and c-MYC overexpression, suggesting an important yet currently unknown molecular mechanism that might connect these two oncogenic events.

Figure 2:
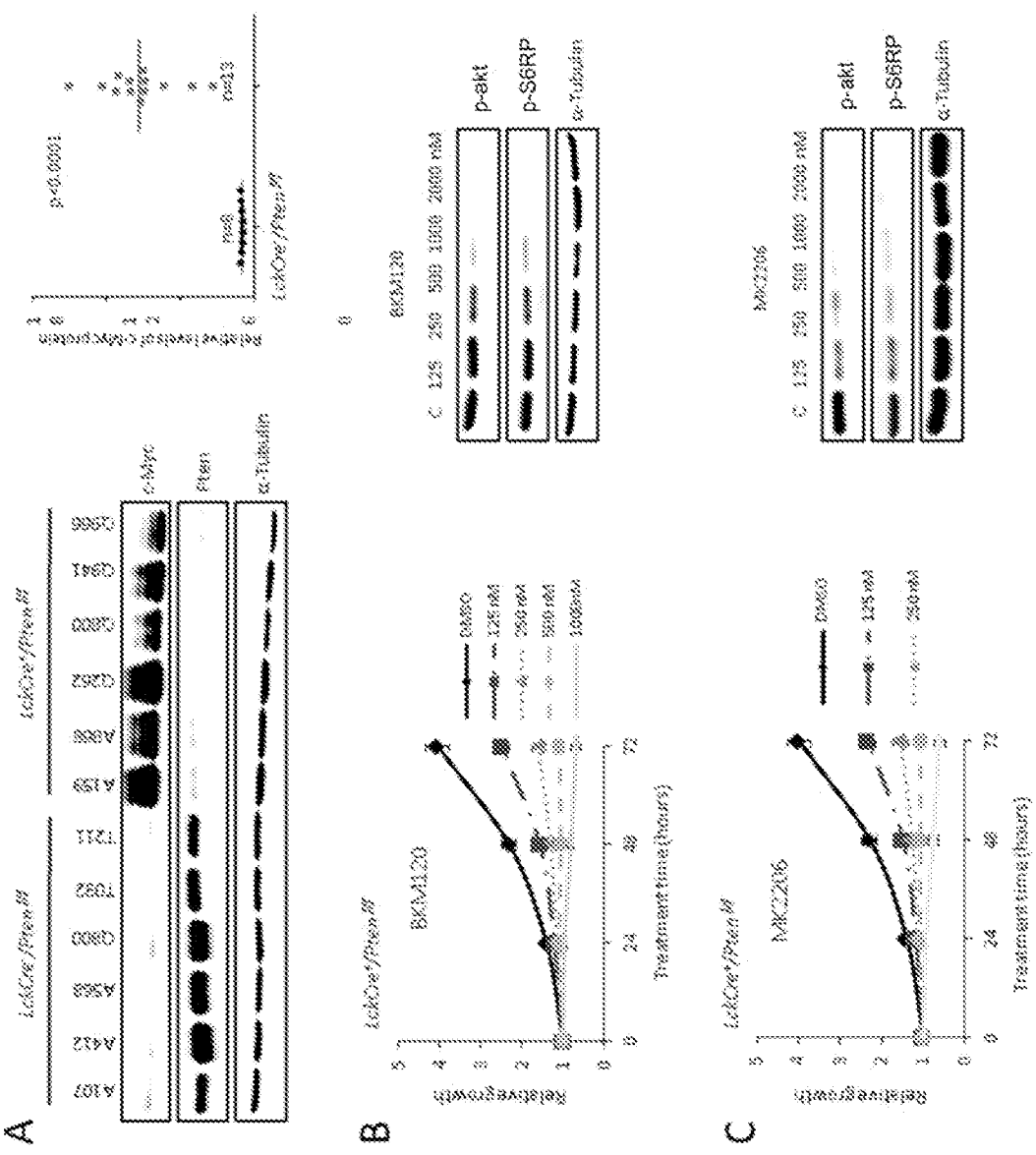
FIG. 2 includes 7 panels, identified as panels (A), (B), (C), (D), (E), (F), and (G), which show that inhibition of PI3K or AKT activity inhibits overexpressed c-MYC in PTEN-deficient T-ALL. Panel A shows that the abundance of c-Myc protein in the thymocytes of LckCre$^+$/Pten$^{f/f}$ moribund mice is significantly higher than that of age matched LckCre$^-$/Pten$^{f/f}$ healthy mice. Panels B and C show that PI3K or Akt inhibition by BKM120 or MK2206 treatment as indicated reduced both the growth and p-Akt in LckCre$^+$/Pten$^{f/f}$ primary tumor cells. For growth inhibition, indicated drugs were applied at indicated concentrations for indicated hours before measurement. For Western blotting, cells were treated with indicated drugs for one hour. DMSO was used as negative control. Panels D and E show that the abundance c-Myc protein in LckCre$^+$/Pten$^{f/f}$ primary tumor cells was reduced upon one hour treatment with BKM120 or MK2206 in a dose-dependent manner. Panel F shows that ectopic expression of Pten suppressed c-Myc protein level and PI3K signaling in LckCre$^+$/Pten$^{f/f}$ primary tumor cells. Panel G shows that the abundances of both c-MYC protein and PI3K signaling in human PTEN-deficient T-ALL cells are reduced upon one hour treatment with MK2206.
Figure 2:
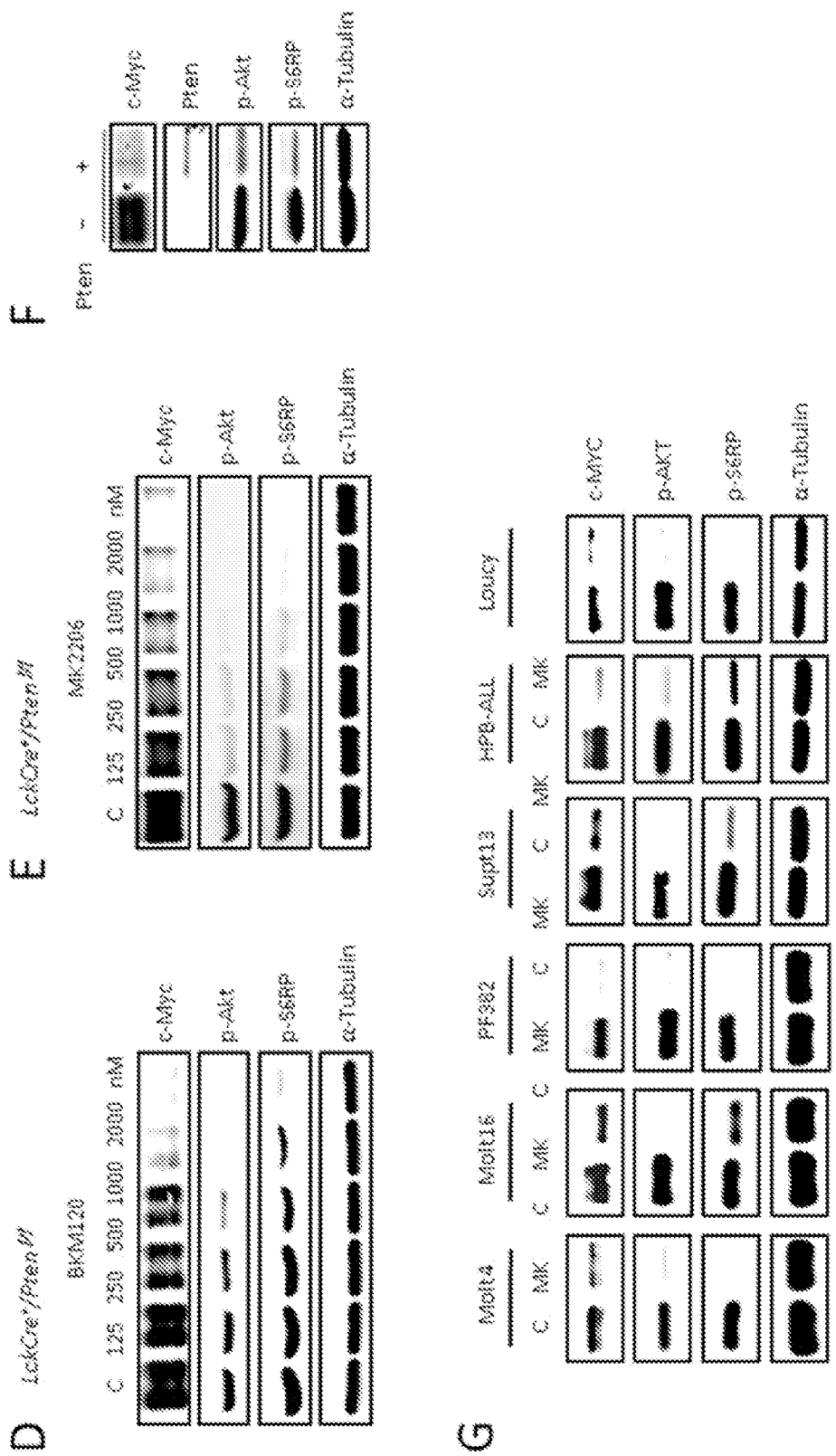

Specifically, in order to establish a T-ALL tumor model driven by Pten loss, floxed Pten mice (Lesche et al. (2002) *Genesis* 32:148-149) were crossed with transgenic mice in which Cre expression is driven by the proximal Lck promoter (LckCre) to effect genetic ablation of Pten specifically in T lymphocytes (Hennet et al. (1995) *Proc. Natl. Acad. Sci. U.S.A.* 92:12070-12074). Consistent with previous studies (Hagenbeek and Spits (2008) *Leukemia* 22:608-619), most LckCre$^+$/Pten$^{f/f}$ mice developed T cell malignancies (latency, 120 days; penetration, 93%) (FIG. 1A). These mice displayed significant size increases in the spleen, liver, thymus, and lymph nodes (FIG. 1B) largely due to invasion of lymphoblasts (FIG. 1C). White blood cell counts were also highly elevated in the peripheral blood of moribund LckCre$^+$/Pten$^{f/f}$ mice (FIG. 1D), indicating the development of leukemia. Similar to previously reported LckCre$^+$/Pten$^{f/f}$, Mx1Cre$^+$/Pten$^{f/f}$ and CD4Cre$^+$/Pten$^{f/f}$ mice (Guo et al. (2008) *Nature* 453:529-533; Liu et al. (2010) *J. Clin. Invest.* 120:2497-2507; and Zhang et al. (2011) *Leukemia* 25:1857-1868), c-Myc protein levels in the thymocytes of moribund LckCre$^+$/Pten$^{f/f}$ mice were dramatically elevated (FIG. 2A).

Work in breast cancer models has demonstrated that c-Myc overexpression causes resistance to PI3K inhibition (Ilic et al. (2011) *Proc. Natl. Acad. Sci. U.S.A.* 108:E699-E708 and Liu et al. (2011) *Nat. Med.* 17:1116-1120). To test whether leukemic cells with overexpressed c-Myc from LckCre$^+$/Pten$^{f/f}$ mice are also resistant to PI3K inhibition, primary tumor cells were treated with BKM120 (Elfiky et al. (2011) *J. Transl. Med.* 9:133), a pan-PI3K inhibitor currently under clinical evaluation. Surprisingly, these primary T-ALL cells with robust c-Myc overexpression were highly sensitive to PI3K inhibition (FIG. 2B). Similar results were observed in these cells when treated with MK2206, an AKT inhibitor currently in clinical trials (Chandarlapaty et al. (2011) *Cancer Cell* 19:58-71) (FIG. 2C). These data indicate that, despite its markedly overexpressed c-Myc, T-ALL driven by Pten-loss in this murine model is still dependent on the PI3K-Akt pathway.

Example 3

The PI3K/AKT Activity Controls the Amount of c-MYC Protein Expressed in PTEN-Deficient T-ALL In order to determine whether c-Myc levels in Pten-null driven T-ALL are altered in response to PI3K or Akt inhibition, primary tumor cells isolated from moribund LckCre$^+$/Pten$^{f/f}$ mice were treated with either BKM120 or MK2206, and then the protein abundance of c-Myc was measured. Notably, both PI3K and AKT inhibitors dramatically decreased the abundance of c-Myc protein in these cells in a dose-dependent manner (FIGS. 2E-2E). Furthermore, restoring the expression of Pten in these primary Pten-null T-ALL cells greatly reduced the abundance of c-Myc protein as well as the phosphorylation of both Akt and S6RP (FIG. 2F). These data indicate that the PI3K/Akt signaling pathway tightly controls the abundance of c-Myc protein in this T-ALL model driven by Pten-loss.

Figure 3:
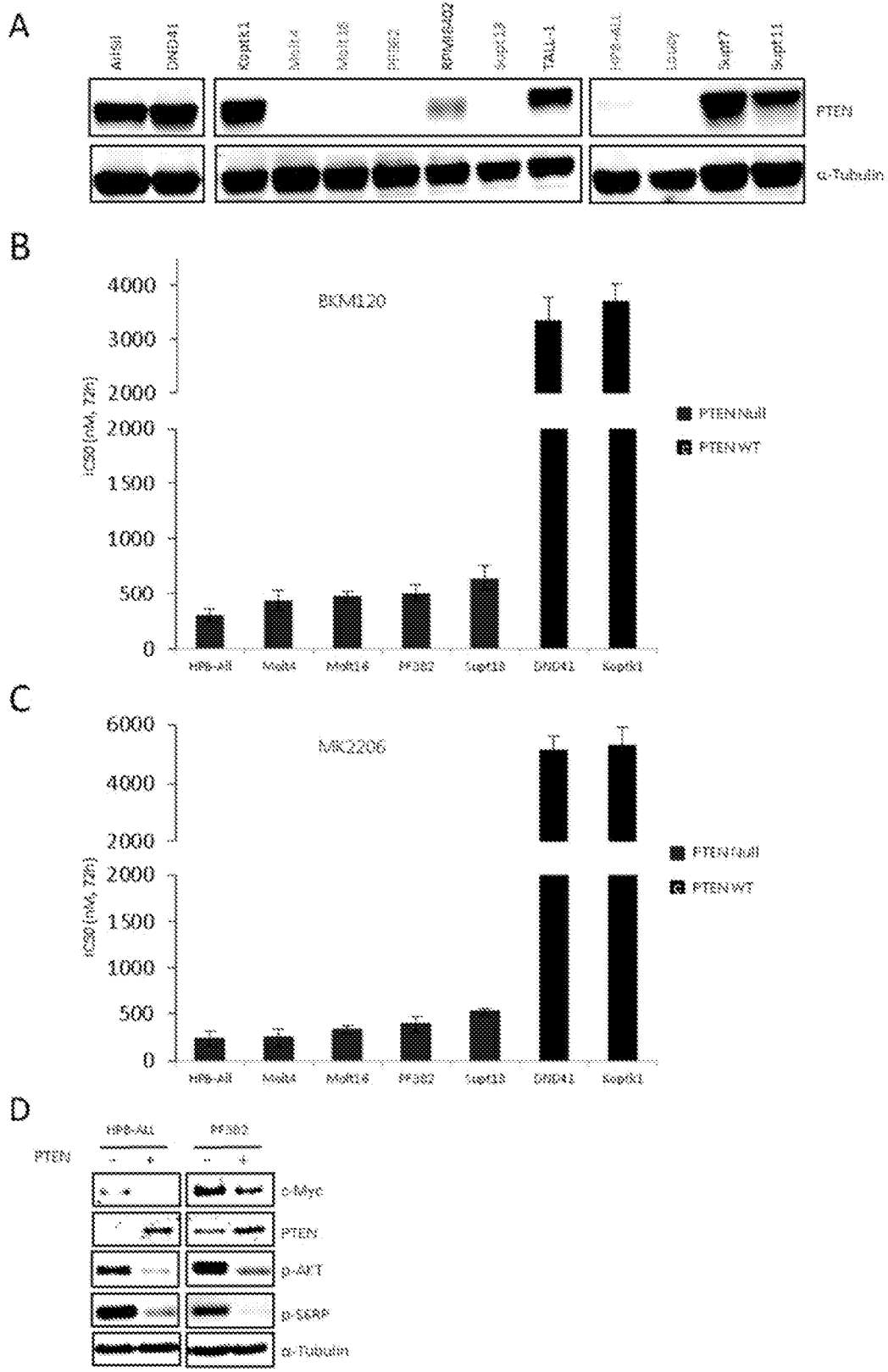
FIG. 3 includes 4 panels, identified as panels (A), (B), (C), and (D), which further show that inhibition of PI3K signaling reduces the amount of c-MYC protein in human PTEN-deficient T-ALL. Panel A shows that six out of thirteen T cell lymphoma/leukemia cell lines showed low or undetectable PTEN protein levels. Panels B and C show that BKM120 (Panel B) and MK2206 (Panel C) effectively inhibits cell proliferation of a panel or PTEN-deficient, c-MYC-high T-ALL cell lines with IC50 at nanomolar range as compared to PTEN-wild type T-ALL cells. Cells were seeded into 96-well plates and the inhibitors were applied at concentration gradients. Seventy-two hours after the drug treatment, cell proliferation was measured by MTS assay with IC50s calculated using Prism 6. Panel D shows that ectopic expression of PTEN suppressed c-MYC protein level and PI3K signaling in PTEN deficient T-ALL cell lines HPB-ALL and PF382.

These findings were extended to human T cell lymphoma/leukemia cell lines. A panel of T cell lymphoma or T-ALL cells was screened. Out of thirteen cell lines tested, six cell lines demonstrated either low or undetectable expression of PTEN (FIG. 3A). In all six cell lines, AKT inhibition by MK2206 decreased c-MYC protein levels (FIG. 2G). Both BKM120 and MK2206 were confirmed to inhibit the proliferation of PTEN null cells, but not PTEN wild type cells (FIGS. 3B-3C). Ectopic expression of PTEN also decreased c-MYC levels in human PTEN-deficient T-ALL cell lines (FIG. 3D). These results indicate that the link between PI3K/AKT pathway activation and c-MYC protein elevation observed in the murine model of Pten-null T-ALL is also evident in most PTEN-deficient human T-ALL cell lines.

Example 4

The mTORC1-S6K1 Axis Downstream of PI3K/Akt Regulates c-Myc Protein Synthesis

The nature of the regulation of c-Myc by the PI3K-Akt pathway activation was also determined. It was first determined that gene expression levels of Myc are increased in the LckCre$^+$/Pten$^{f/f}$ primary tumor cells (FIG. 4A), consistent with previously described Pten-null T-ALL models (Guo et al. (2008) *Nature* 453:529-533; Liu et al. (2010) *J. Clin. Invest.* 120:2497-2507; and Zhang et al. (2011) *Leukemia* 25:1857-1868). While PI3K/Akt inhibition caused a dramatic decrease of c-Myc protein abundance (FIG. 2), the level of Myc mRNA in these cancer cells was not altered upon treatment with the AKT inhibitor, MK2206 (FIG. 4B), indicating that the gene expression of Myc is not affected by PI3K/Akt activity.

It has been reported that GSK3β, a downstream effector of AKT, can regulate c-MYC protein stability through phosphorylation of c-MYC at the threonine-58 residue (T58) and subsequent proteasome-mediated degradation (Sears et al. (2000) *Genes Dev.* 14:2501-2514). To test whether this mechanism is also functioning in the T-ALL model, primary T-ALL cells were treated with the translation elongation inhibitor, cycloheximide (CHX), either alone or in combination with MK2206. Application of CHX suppresses biosynthesis and as a result, c-Myc protein levels quickly decreased due to the protein's short half-life. Addition of MK2206, however, failed to either expedite or postpone the degradation of c-MYC (FIG. 4C). These results indicate that PI3K/Akt signaling has little effect on the stability of c-Myc protein in these T-ALL cells.

It was next determined whether the PI3K pathway regulates de novo synthesis of the c-Myc protein. LckCre$^+$/Pten$^{f/f}$ primary tumor cells were pre-treated with CHX to deplete c-Myc protein, and CHX was subsequently washed away, quickly followed by the addition of MG132, a proteasome inhibitor, to preserve newly synthesized c-Myc. As expected, newly synthesized c-Myc was stabilized and accumulated in MG132 treated cells, but not in cells treated with MG132 plus CHX (FIG. 4D). Strikingly, little c-Myc protein was detected in cells treated with MG132 plus MK2206 (FIG. 4D), indicating that Akt inhibition profoundly blocked de novo synthesis of c-Myc.

The mechanism by which the PI3K/Akt pathway regulates c-Myc translation in LckCre$^+$/Pten$^{f/f}$ primary tumor cells was determined. The effect of the inhibition of mTORC1, an essential downstream effector of PI3K/Akt known to be critical for translational control, on the c-Myc protein abundance in these cells was tested. The LckCre$^+$/Pten$^{f/f}$ primary tumor cells were treated with an mTORC1 inhibitor, RAD001, or the PI3K/mTORC1 dual inhibitor, BEZ235 (Maira et al. (2008) *Mol. Cancer Ther.* 7:1851-1863 and Schuler et al. (1997) *Transplantation* 64:36-42), and it was found that both inhibitors indeed dramatically suppressed c-Myc protein levels and the downstream signaling of their targets (FIGS. 4E-4F). The growth of these primary tumor cells was also markedly reduced in a dose-dependent manner (FIG. 4E-4F). Similar to MK2206 described above, neither BEZ235 nor RAD001 affected Myc transcription or degradation in primary cells (FIGS. 5A-5B). To determine whether the phenotype observed in vitro could be replicated in vivo, the ability of the PI3K/mTORC1 dual inhibitor, BEZ235 (Maira et al. (2008) *Mol. Cancer Ther.* 7:1851-1863), to suppress tumor growth and c-Myc protein levels in vivo was measured (FIGS. 5E-5F). Results obtained in vivo were essentially identical to those observed in vitro.

While mTORC1 has been previously implicated in regulating c-MYC (West et al. (1998) *Oncogene* 17:769-780), the mechanism is unclear. It was previously found that the kinase substrate of mTORC1, S6K1, plays a critical role in assembling the translation pre-initiation complex (Holz et al. (2005) *Cell* 123:569-580). To investigate whether S6K1 plays a role in regulating c-Myc protein in the Pten-null T-ALL model, a small molecule inhibitor of S6K1, PF470861, was used. S6K1 inhibition effectively decreased c-Myc protein levels and inhibited tumor cell proliferation in a dose-dependent manner (FIG. 4G). Similar to the inhibition of its upstream activators, S6K1 inhibition did not affect gene transcription or protein stability of c-Myc (FIGS. 5H-5I). Consistent with the treatment of MK2206, application of either RAD001 or BEZ235 or PF470861 markedly prevented c-Myc protein de novo synthesis in LckCre$^+$/Pten$^{f/f}$ primary tumor cells (FIG. 4H). Together, these results indicate that the mTORC1-S6K1 axis downstream of PI3K/Akt plays a critical role in the regulation of c-Myc de novo synthesis.

Example 5

Figure 4:
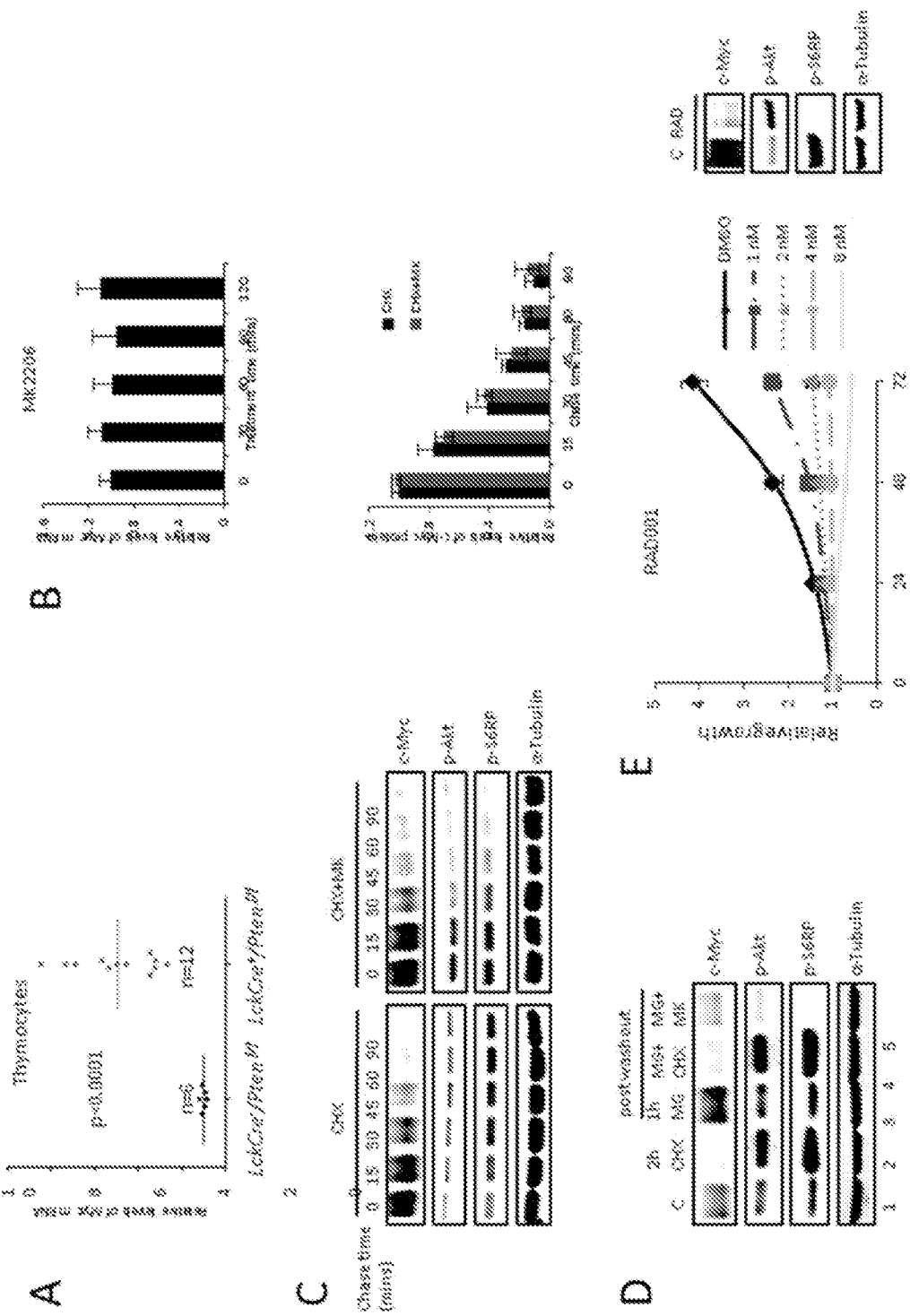
FIG. 4 includes 14 panels, identified as panels (A), (B), (C), (D), (E), (F), (G), (H), (I), (J), (K), (L), (M), and (N), which show that PI3K-mTORC1-S6K1 signaling regulates c-Myc de novo synthesis in murine Pten-null T-ALL. Panel A shows that the expression levels of c-Myc mRNA in the thymocytes LckCre$^{30}$/Pten$^{f/f}$ moribund mice are significantly higher than that of age matched LckCre$^-$/Pten$^{f/f}$ healthy mice. Panel B shows that the expression levels of c-Myc mRNA in primary T-ALL cells derived from LckCre$^{30}$/Pten$^{f/f}$ mice remain unchanged upon 1 μM MK2206 treatment at the indicated time points. c-Myc mRNA levels were measured by quantitative PCR. GAPDH was used as control. Panel C shows that the c-Myc protein stability in primary T-ALL cells derived from LckCre$^+$/Pten$^{f/f}$ mice remained unchanged upon MK2206 treatment for the indicated time points. Cells treated with 25 μg/ml cycloheximide (CHX) with or without 1 μM MK2206 are indicated. Panel D shows that AKT inhibition blocked the de novo synthesis of c-Myc protein. LckCre$^+$/Pten$^{f/f}$ primary tumor cells (lane 1) were pre-treated with 25 μg/ml CHX for two hours to deplete c-Myc protein (lane 2) and cells were washed three times with PBS to allow new biosynthesis. MG132 was then added at 10 μM either alone (lane 3) or with 25 μg/ml CHX (lane 4) or with 1 μM MK2206 (lane 5) for one hour. Panels E through G show that PI3K, mTORC1 or S6K1 inhibition by RAD001, BEZ235 or PF4708671 treatment as indicated reduced both the growth and c-Myc protein abundance in LckCre$^+$/Pten$^{f/f}$ primary tumor cells. For growth inhibition, the indicated drugs were applied at indicated concentrations for the indicated hours before measurement. For Western blotting, cells were treated with indicated drugs for two hours. DMSO was used as negative control. Panel H shows that the PI3K, mTORC1-S6K1 inhibition by RAD001, BEZ230 or PF4708671 treatment as indicated blocked the de novo synthesis of c-Myc protein. LckCre$^+$/Pten$^{f/f}$ primary tumor cells (lane 1) were pre-treated with 25 µg/ml CHX for two hours to deplete c-Myc protein (lane 2) and cells were washed three times with PBS to allow new biosynthesis. MG132 was then added at 10 µM either alone (lane 3), or with 25 µg/ml CHX (lane 4), or with 100 nM RAD001 (lane 5), or with 100 nM BEZ235 (lane 6), or with 10 µM PF4708671 (lane 7) for two hours. Panels I and J show that the abundances of c-MYC protein were reduced upon RAD001 or PF4708671 treatment in HPB-ALL, and PF382 cells. DMSO treatment was used as negative control. Panel K shows that the inhibition of AKT/mTORC1/S6K1 did not change the level of MYC transcription. HPB-ALL cells were treated with MK2206, RAD001 or PF4708671 for one to four hours as indicated. c-MYC mRNA levels were measured by quantitative PCR. GAPDH was used as control. Panel L shows that inhibition of AKT/mTOR/S6K1 did not affect c-MYC protein stability. HPB-ALL cells were treated with 25 µg/ml cycloheximide (CHX) with or without MK2206, RAD001 or PF4708671 for the indicated time points. Cell lysates were subjected to Western blotting, followed by quantification. Panels M and N show that c-MYC translation is inhibited by RAD001 or PF4708671 treatment. Polysome profiling assay was performed and fractions were collected. RT-PCR was performed to detect mRNA distribution. GAPDH mRNA was used as a control.
Figure 4:
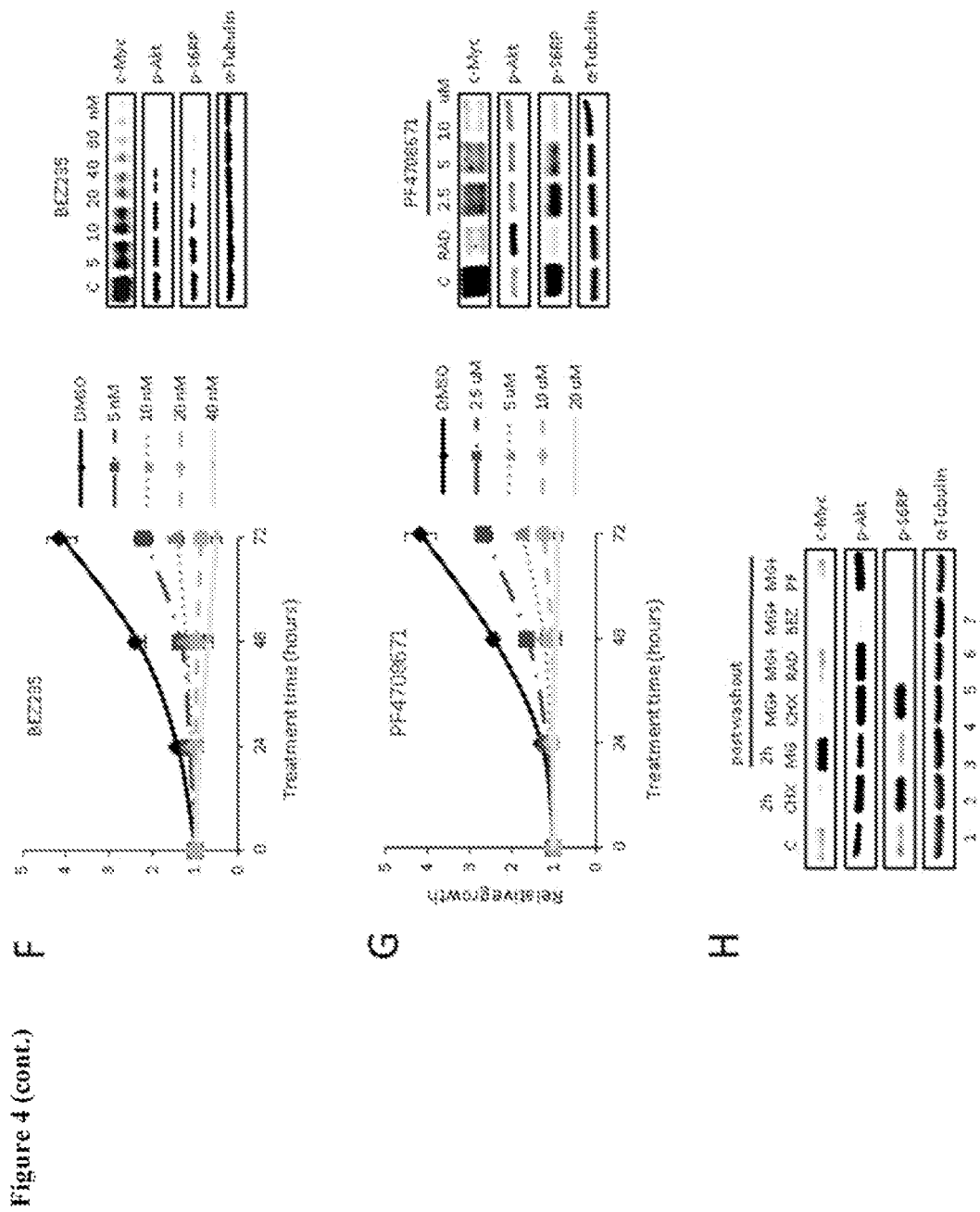
Figure 4:
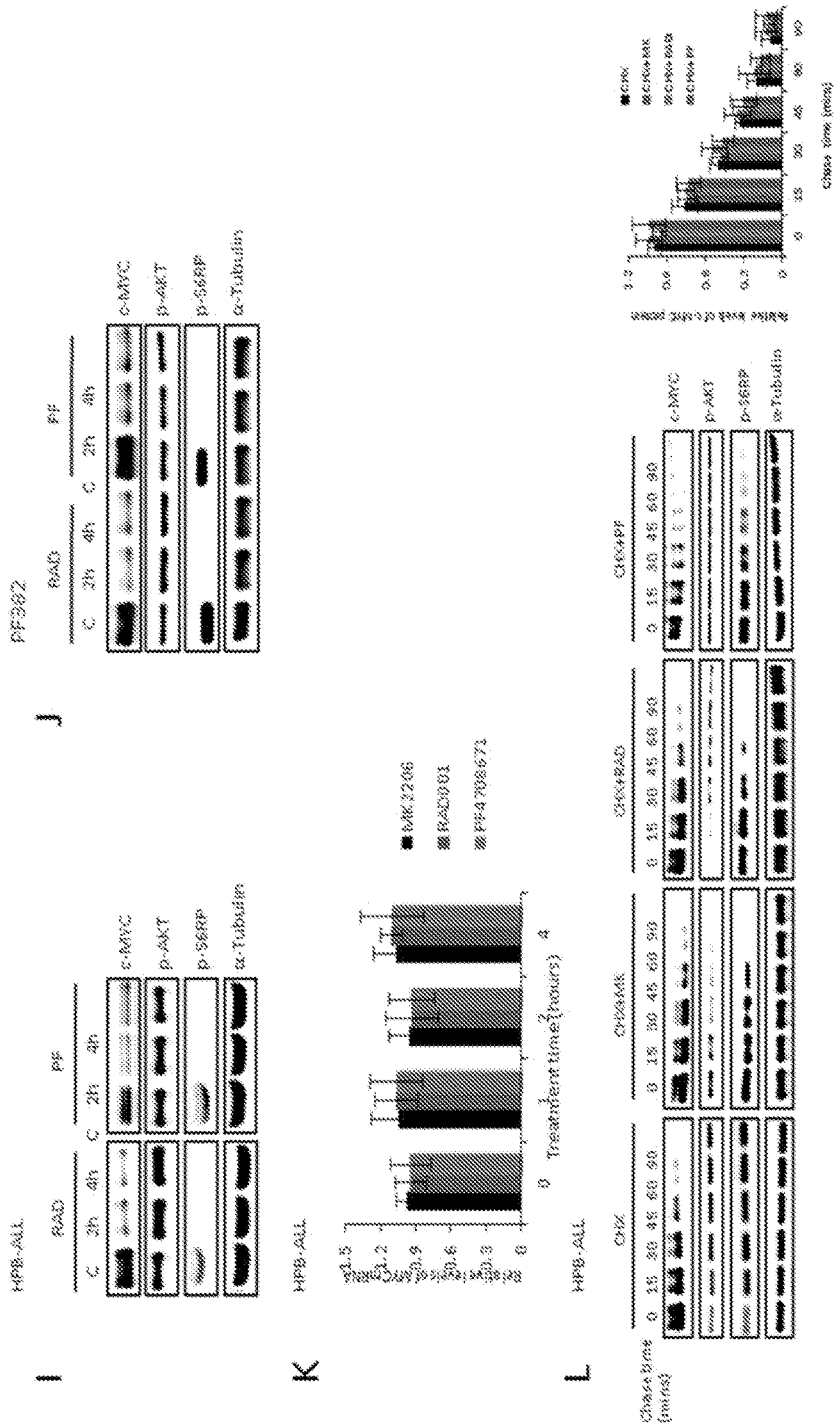
Figure 4:
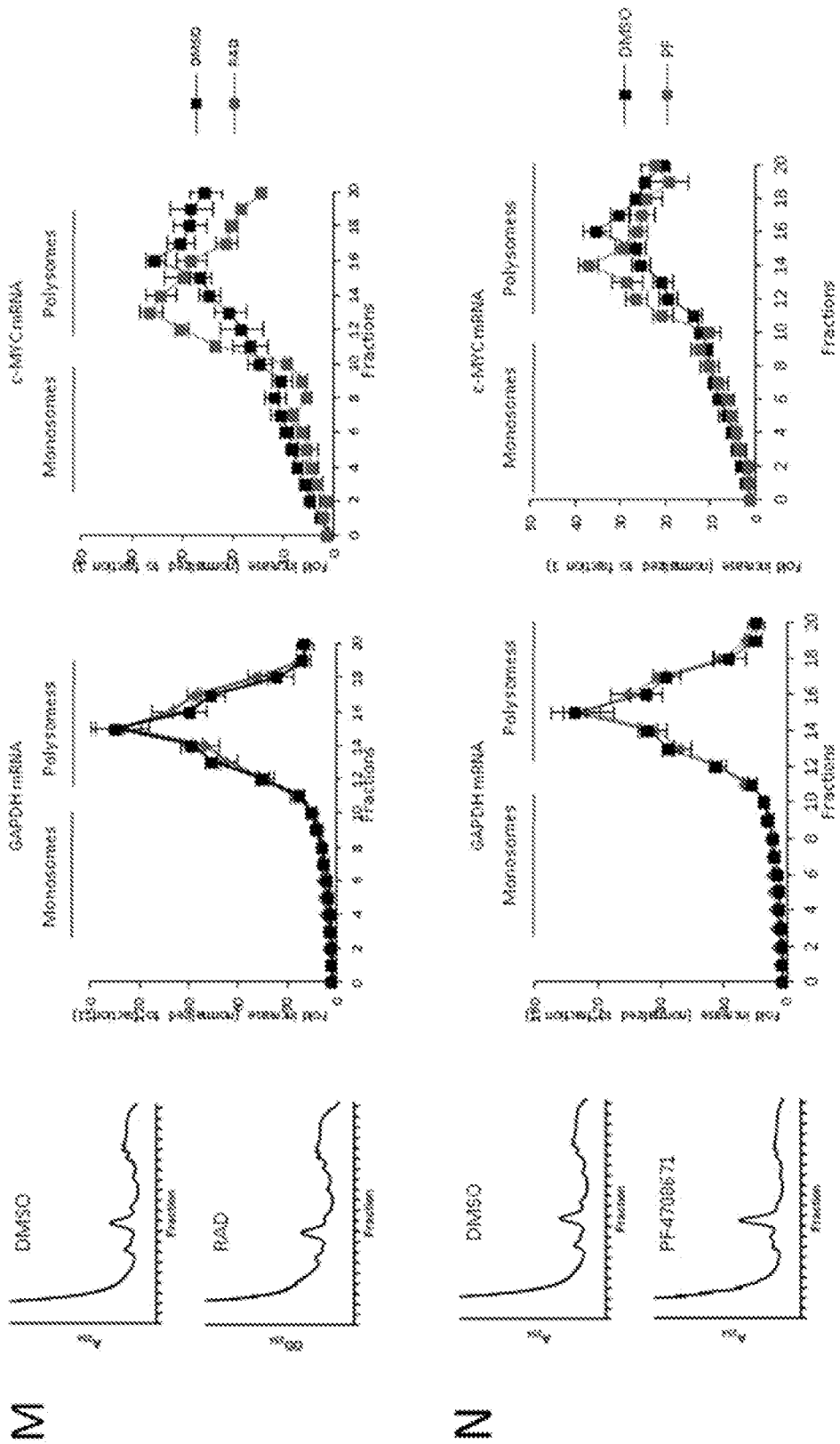
Figure 5:
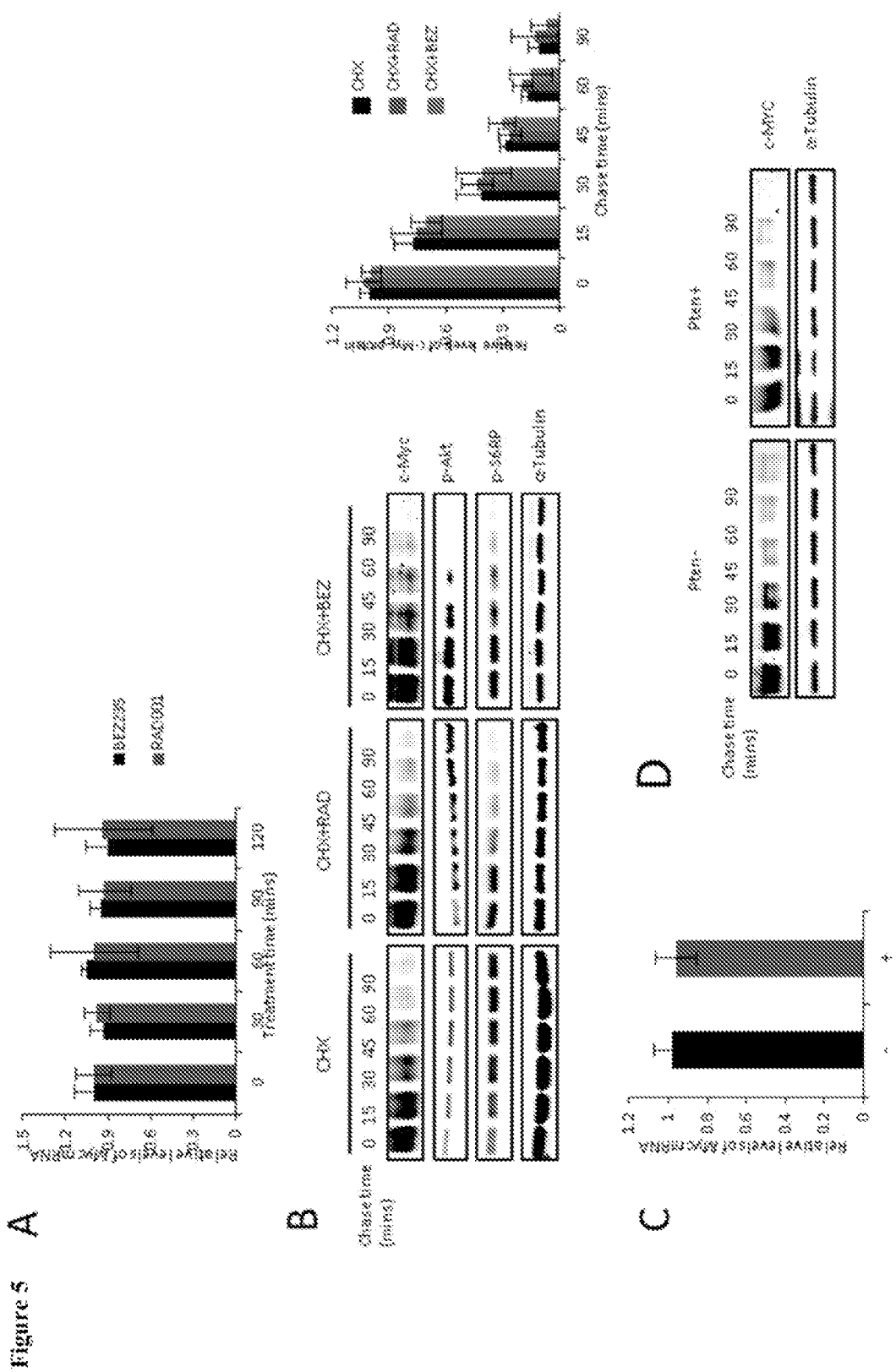
FIG. 5 includes 9 panels, identified as panels (A), (B), (C), (D), (E), (F), (G), (H), and (I), which further show that the mTORC1-S6K1 axis downstream of PI3K/Akt regulates c-Myc de novo synthesis. Panel A shows that the expression levels of c-Myc mRNA in primary T-ALL cells derived from LckCre$^+$/Pten$^{f/f}$ mice remain unchanged upon 100 nM BEZ235 or 100 nM RAD001 treatment at the indicated time points. c-Myc mRNA levels were measured by quantitative PCR. GAPDH was used as control. Panel B shows that the c-Myc protein stability in primary T-ALL cells derived from LckCre$^+$/Pten$^{f/f}$ mice remained unchanged upon RAD001 or BEZ235 treatment for the indicated time points. Cells treated with 25 µg/ml cycloheximide (CHX) alone or with 100 nM RAD001 or 100 nM BEZ235 are indicated. Panel C shows that ectopic expression of Pten doesn't change c-Myc mRNA levels. c-Myc mRNA levels were measured by quantitative PCR. GAPDH was used as a control. Panel D shows that c-Myc protein stability remained unchanged upon ectopic expression of Pten for the indicated time points. Cells treated with 25 µg/ml cycloheximide (CHX) are indicated. Panel E shows that recipient mice transplanted with two million LckCre$^+$/Pten$^{f/f}$ moribund mice thymocytes showed prolonged survival curve with daily BEZ235 treatment (35 mg/kg) compared to control treatment. Arrow indicates the starting date of treatment (day 14) post transplantation. Panels F and G show that recipient mice transplanted with two million LckCre$^+$/Pten$^{f/f}$ moribund mice thymocytes showed suppressed PI3K signaling as measured by p-Akt (S473), p-S6RP (S235/236) IHC staining (Panel F), deceased proliferation rate as measured by Ki67 IHC staining (Panel F) and decreased c-Myc protein levels as detected by Western blotting (Panel G) after three days of BEZ235 daily treatment (35 mg/kg), starting at 14 days post transplantation. PEG300 was used as control treatment for in vivo inhibitor administration. Panel H shows that the expression levels of c-Myc mRNA in primary T-ALL cells derived from LckCre$^+$/Pten$^{f/f}$ mice remain unchanged upon 10 µM PF4708671 treatment at the indicated time points. c-Myc mRNA levels were measured by quantitative PCR. GAPDH was used as a control. Panel I shows that the c-Myc protein stability in primary T-ALL cells derived from LckCre$^+$/Pten$^{f/f}$ mice remained unchanged upon treatment for the indicated time points. Cells treated with 25 µg/ml cycloheximide (CHX) with or without 10 µM PF4708671 are indicated.
Figure 5:
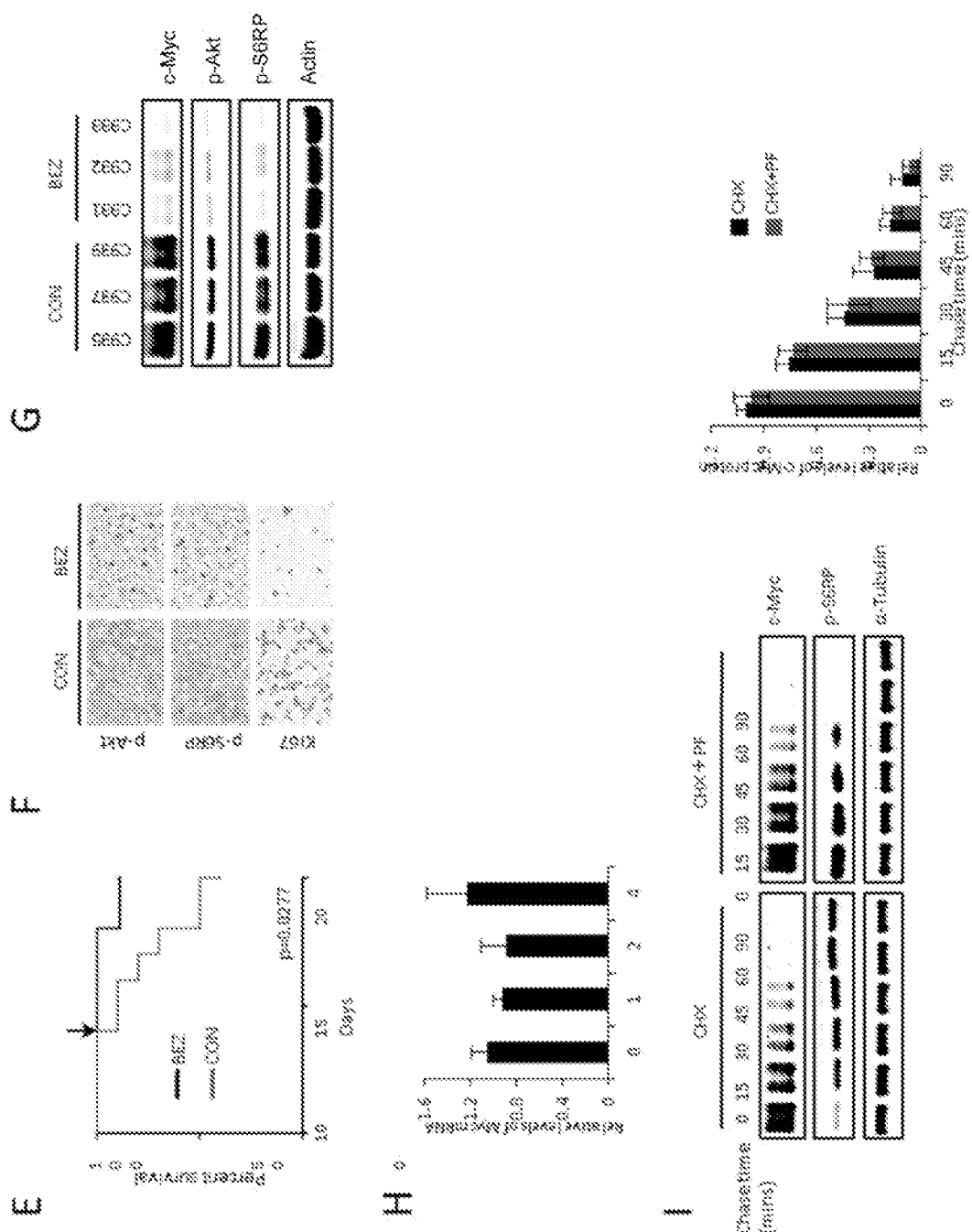
Figure 6:
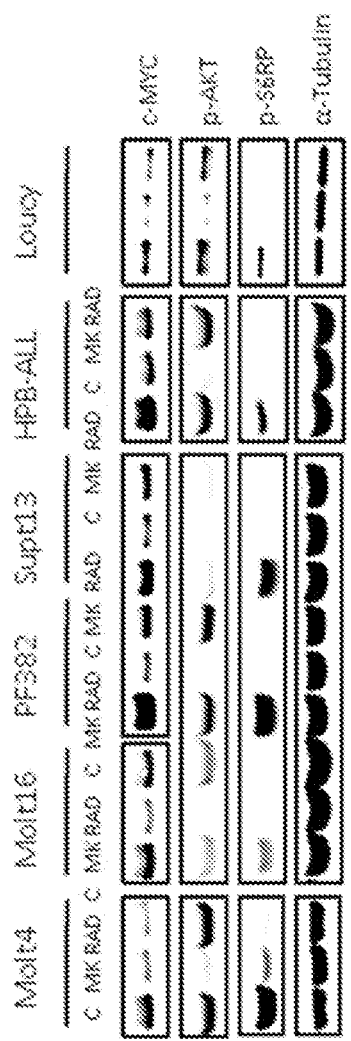
FIG. 6 includes 3 panels, identified as panels (A), (B), and (C), which show that the mTORC1-S6K1 axis regulates the de novo synthesis of c-MYC protein in human PTEN-deficient T-ALL cell line. Panel A shows that the abundances of both c-MYC protein and PI3K signaling in human PTEN-deficient T-ALL cells are reduced upon one hour treatment with MK2206 or RAD001. Panel B shows that the inhibition of AKT/mTORC1/S6K1 did not change the level of MYC transcription. PF382 cells were treated with MK2206, RAD001 or PF4708671 for one to four hours as indicated. c-MYC mRNA levels were measured by quantitative PCR. GAPDH was used as a control. Panel C shows that inhibition of AKT/mTOR/S6K1 did not affect c-MYC protein stability. PF382 cells were treated with 25 µg/ml cycloheximide (CHX) with or without MK2206, RAD001 or PF4708671 or the indicated time points. Cell lysates were subjected to Western blotting, followed by quantification.
Figure 6:
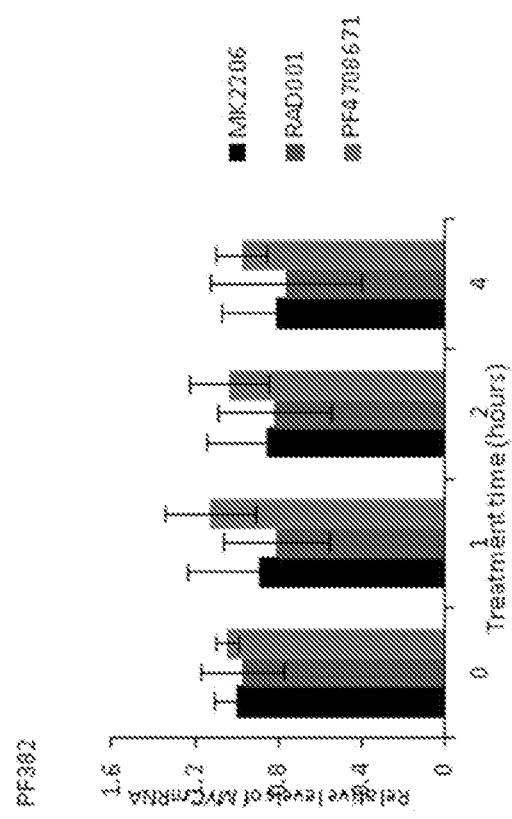
Figure 6:
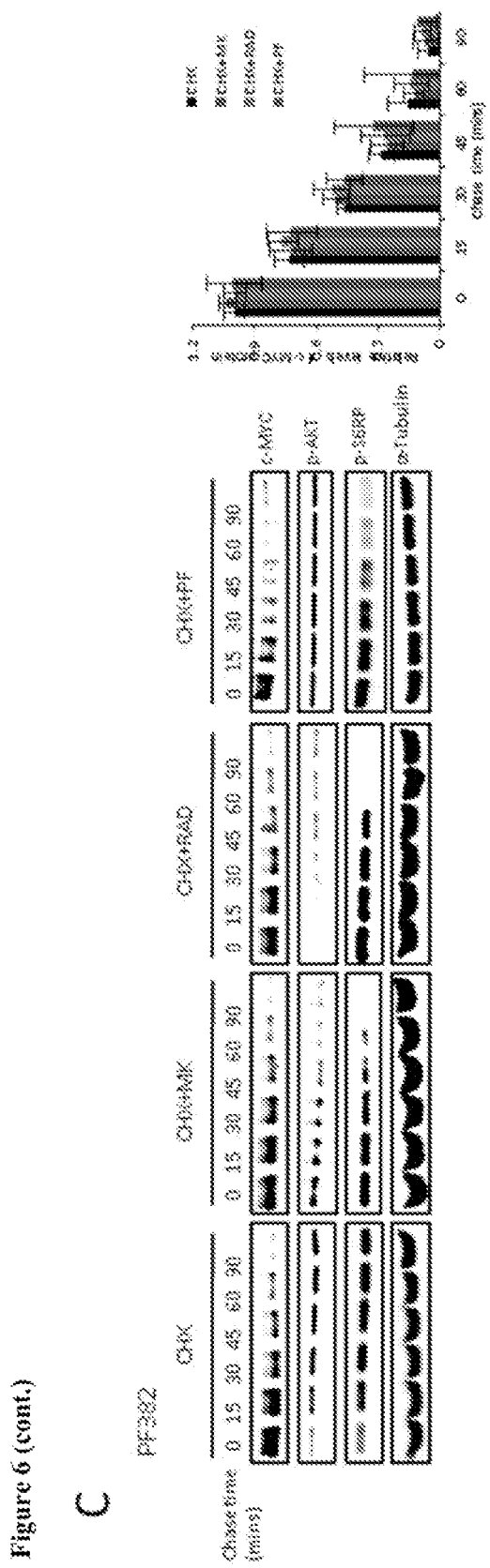

The mTORC1-S6K1 Axis Governs the De Novo Synthesis of c-MYC Protein in Human PTEN-Deficient T-ALL Cell Lines As described above, c-MYC protein levels were inhibited by application of the AKT inhibitor MK2206 in a panel of human PTEN-deficient T-ALL cell lines (FIG. 4). To determine whether mTORC1 can also regulate c-MYC in human PTEN-deficient T-ALLs, the six cell lines described above and in FIG. 4 were treated with RAD001. Similar to the inhibition of AKT, mTORC1 inhibition in all these cell lines decreased c-MYC protein abundance (FIG. 6A). Two of the PTEN-deficient, c-MYC high T-ALL cell lines, HPB-ALL and PF382, were chosen for subsequent studies. Similar to the inhibition of mTORC1, inhibition of S6K1 also greatly suppressed c-MYC protein levels in HPB-ALL and PF382 (FIGS. 4I-4J). Consistent with the findings in the primary cells, the application of MK2206, or RAD001, or PF470861 had little effect on neither gene expression of MYC (FIGS. 4K and 6B) or c-MYC protein stability (FIGS. 4L and 6C) in both cell lines. To confirm that the regulation of PI3K signaling on c-MYC is indeed translational, polysome profiling experiments were performed on the HPB-ALL cell line using RAD001 and PF4708671. Significantly, the c-MYC mRNA profiling was moved to the lower fractions of polysomes upon the treatment of RAD001 or PF470861 (FIGS. 4M-4N), demonstrating that the mTORC1-S6K1 axis controls c-MYC protein de novo synthesis in human PTEN-deficient T-ALL cell lines.

Example 6

Figure 7:
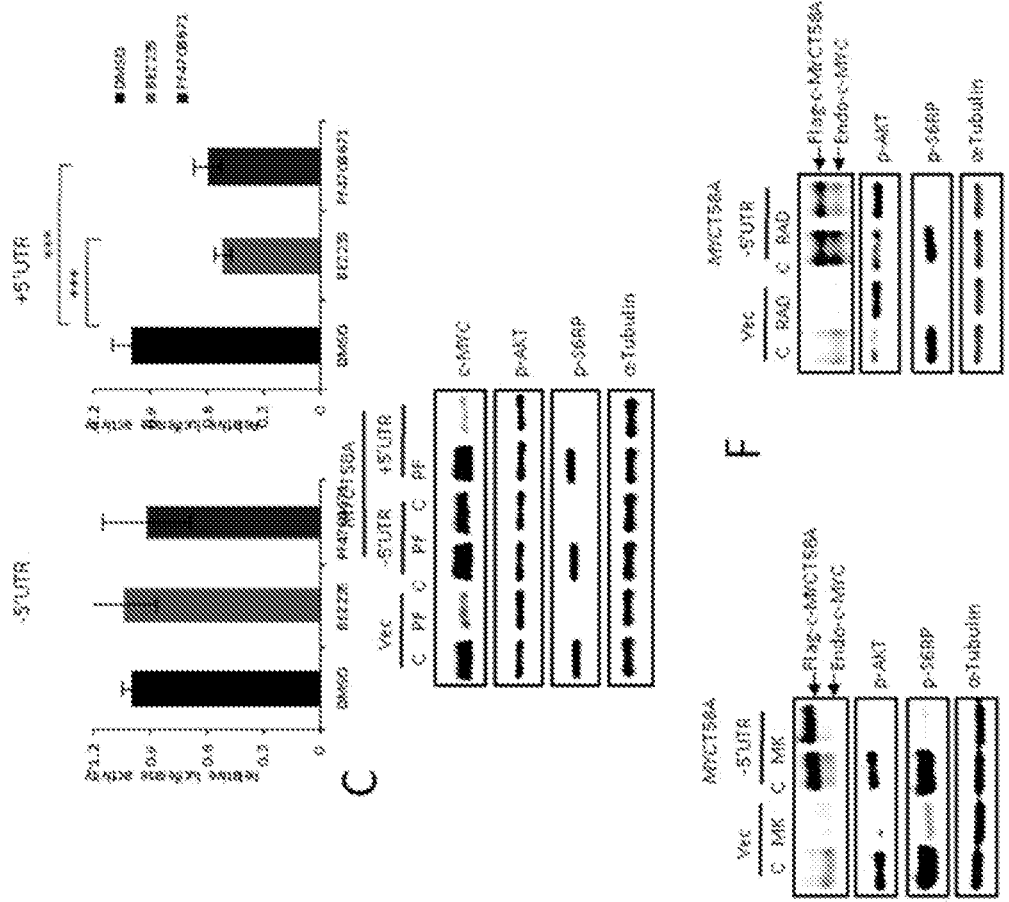
FIG. 7 includes 14 panels, identified as panels (A), (B), (C), (D), (E), (F), (G), (H), (I), (J), (K), (L), (M), and (N), which show that PI3K/mTOR/S6K1 signaling regulates the 5'UTR-dependent, eIF4B/4A-mediated translation of c-Myc. Panel A shows that the activity of firefly luciferase reporter in the construct carrying a MYC 5'UTR is sensitive to the inhibition of PI3K/mTORC1 or S6K1. Normalized units of luciferase activities in the cell lysates from co-transfection of the pGL3 with or without the 5'UTR of human MYC and the pRL renilla luciferase reporter as internal control are shown. Luciferase activities were measured in cells treated with BEZ235 or PF4708671 for four hours two days post transfection, *P<0.0005 (Student's t test). Panels B and C show the differential responses of c-MYC protein abundance in HPB-ALL cells expressing vector control, MYC T58A −5'UTR or MYC T58A +5'UTR upon BEZ235 or PF4708671 treatment, as indicated. Panels D and F show the response of Flag-tagged c-MYC T58A protein or endogenous c-MYC protein abundance in HPB-ALL cells upon BKM120, MK2206 or RAD001 treatment, as indicated. Panels G and H show the differential responses of the growth rate of HPB-ALL cells expressing vector, MYC T58A −5'UTR, or MYC T58A +5'UTR as indicated upon BEZ235 or PF4708671 treatment. P<0.005 (Student's t test). Panels I and J show the change of the abundance of c-MYC protein and growth rate of HPB-ALL cells in response to shRNA-mediated knockdown of eIF4B. Cells expressing scramble control (Scr), or five independent shRNA constructs against eIF4B, as indicated. *P<0.05, ***P<0.0005 (n=3 Student's t test). Panels K and L show the change of the abundance of c-MYC protein and growth rate of HPB-ALL cells in response to shRNA-mediated knockdown of eIF4A. Cells expressing scramble control (Scr), or five independent shRNA constructs against eIF4A, as indicated. *P<0.05, ***P<0.0005 (n=3, Student's t test). Panels M and N show that recipient mice transplanted with two million HPB-All cells showed prolonged survival (Panel M) and decreased c-Myc protein levels as detected by Western blotting (Panel N) after knocking-down eIF4A via two independent shRNAs, as compared to the scramble control.
Figure 7:
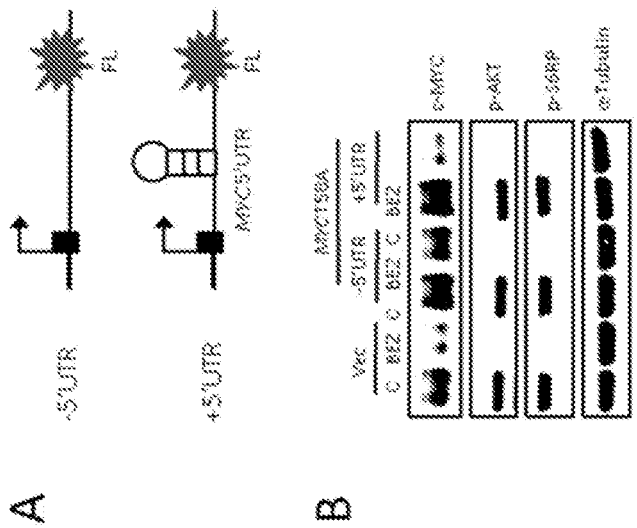
Figure 7:
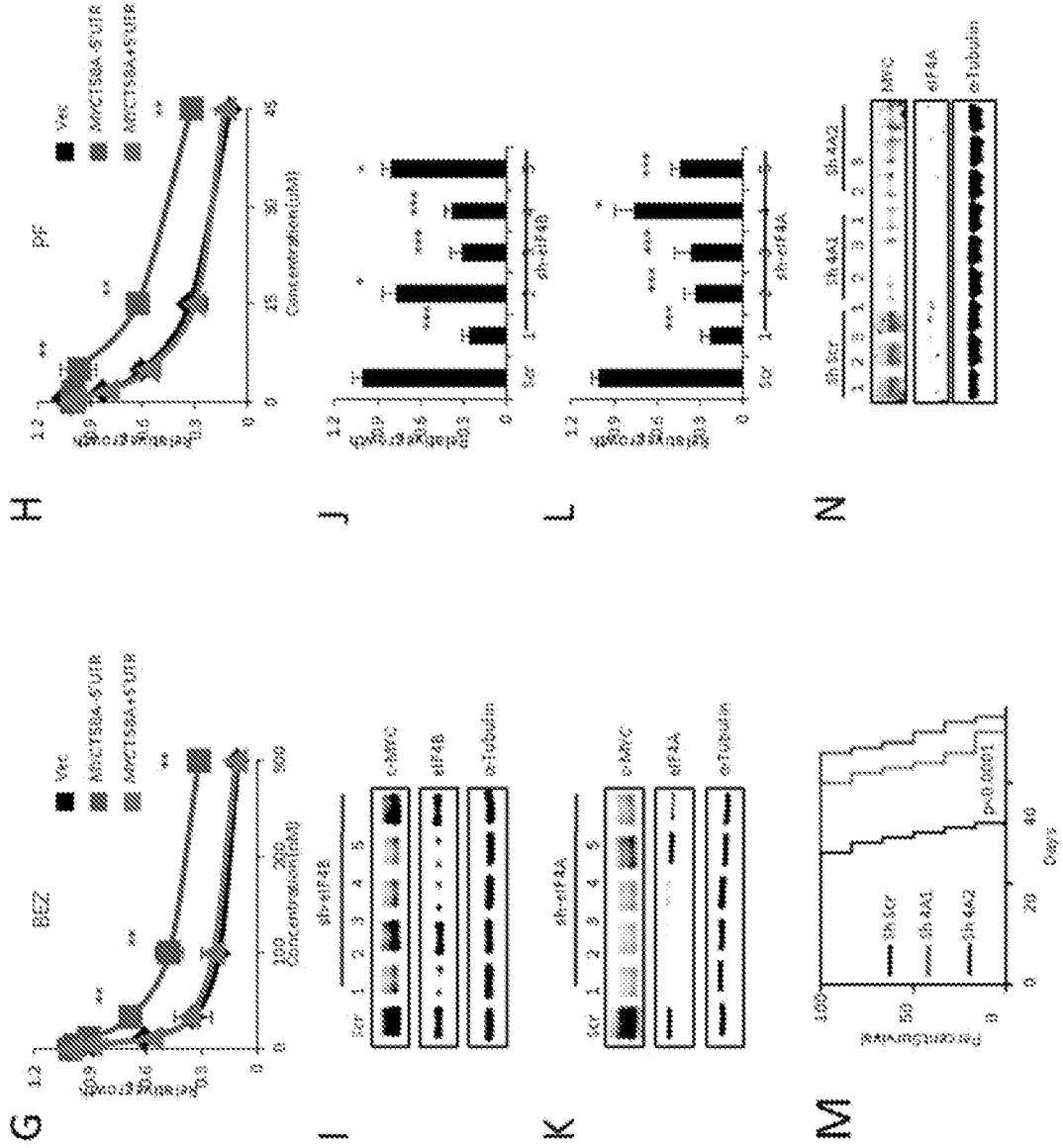
Figure 8:
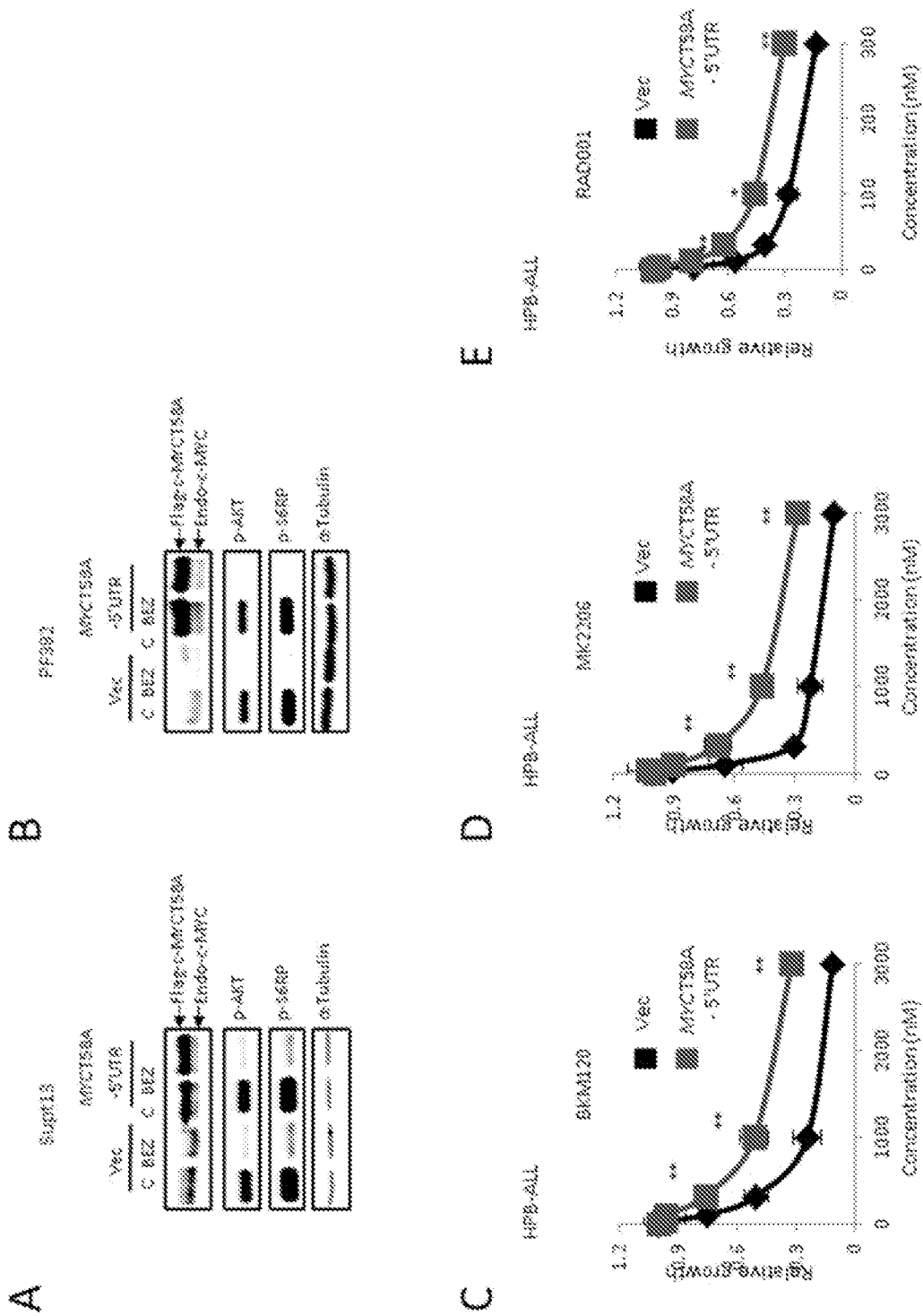
FIG. 8 includes 5 panels, identified as panels (A), (B), (C), (D), and (E), which show that c-MYC translation is regulated by PI3K signaling through the c-MYC 5'UTR. Panels A and B show the response of Flag-tagged c-MYC T58A protein or endogenous c-MYC protein abundance in PTEN-deficient T-ALL cells SuptI3 (Panel A) and PF382 (Panel B) upon BEZ235 treatment, as indicated. Panels C through E show the differential responses of the growth rate of HPB-ALL cells expressing vector, or MYC T58A −5'UTR as indicated upon BKM120 (Panel C), MK2206 (Panel D), or RAD001 (Panel E) treatment. *P<0.05, **P<0.005 (Student's t test).

The PI3K/mTORC1/S6K1 Signaling Axis Regulates a 5'UTR-Dependent Translation of c-MYC mRNA Via eIF4B/eIF4A It was next investigated how mTORC1/S6K1 regulates c-MYC protein synthesis. The mRNA of MYC contains a highly structured 5' untranslated region (5'UTR) (Stoneley et al. (1998) Oncogene 16:423-428) that has been implicated in regulating its translation (Galmozzi et al. (2004) J. Cell Physiol. 200:82-88). To test whether the MYC 5'UTR is critical for the translational control of c-MYC by the PI3K/mTORC1/S6K1 pathway, a luciferase construct in which the SV40 promoter drives firefly luciferase expression either with or without a MYC 5'UTR was used (FIG. 7A). A renilla luciferase construct was used as internal control. The response of luciferase reporter activity to inhibitors targeting the PI3K pathway was tested. Treatment with either BEZ235 or PF470861 significantly reduced the luciferase activity expressed from the construct containing the MYC 5'UTR, but not the one lacking a MYC 5'UTR (FIG. 7A). These data indicate that the PI3K/mTORC1/S6K1 pathway regulates MYC translation via its structured 5'UTR.

To further validate whether MYC 5'UTR is important for its translation regulated by the PI3K/mTORC1/S6K1 signaling axis in PTEN-deficient T-ALL, a retroviral expression vector was used to introduce a stabilized mutant allele of MYC, MYC T58A, with or without the MYC 5'UTR, into HPB-ALL cells, resulting in a pair of isogenic lines: HPB-ALL MYC T58A −5'UTR and HPB-ALL MYC T58A +5'UTR. While the abundance of c-MYC protein in HPB-ALL MYC T58A −5'UTR cells was little changed in response to either BEZ235 or PF4708671, it was markedly reduced in cells expressing HPB-ALL MYC T58A +5'UTR in response to inhibitors treatment despite the presence of the stabilizing mutant c-MYC T58A (FIGS. 7B-7C). The abundance of c-MYC protein in the parental cells expressing vector control was also dramatically reduced by the inhibitor treatments (FIGS. 7B-7C), indicating that endogenous MYC mRNAs in these T-ALL cells carrying a 5'UTR are subjected to the regulation by the PI3K/mTORC1/S6K activity. It was further confirmed that the 5'UTR was present in the Myc mRNA transcripts in the Pten-null T-ALL derived from LckCre⁺/Pten^f/f mice, as well as in a panel of human PTEN-deficient c-MYC high T-ALL lines described and tested herein.

Since the ectopically expressed MYC T58A constructs in this experiment had no tag attached, their protein bands were superimposed with endogenous c-MYC in the Western blotting analysis (FIGS. 7B-7C). A Flag-tagged MYC T58A −5'UTR was expressed in HPB-ALL and a number of additional T-ALL cell lines to display a Flag-tagged c-MYC T58A that is distinct from the endogenous c-MYC (FIGS. 7D-7F and 8A-8B). The results clearly show that, while the abundance of the Flag-tagged c-MYC T58A protein in cells remained unchanged in response to PI3K, AKT or mTORC1 inhibitors, the amount of endogenous c-MYC reduced dramatically upon treatment with these drugs (FIGS. 7D-7F and 8A-8B). Consistent with this finding, HPB-ALL MYC T58A −5'UTR cells have significantly reduced sensitivity to growth inhibition upon treatment with PI3K/mTORC1 or S6K1 inhibitors as compared to parental cells or the isogenic HPB-ALL MYC T58A +5'UTR cells (FIGS. 7G-7H and 8D-8E). Together, these data demonstrate that the PI3K/mTORC1/S6K1 signaling axis governs the translation of MYC mRNAs bearing 5'UTR.

Previous studies have shown that S6K1 can phosphorylate the translation initiation factor eIF4B (Raught et al. (2004) EMBO J. 23:1761-1769), which has been implicated in facilitating the helicase activity of the dead-box RNA helicase eIF4A (Rogers et al. (1999) J. Biol. Chem. 274:12236-12244; Csibi et al. (2014) Curr. Biol. 24:2274-2280; Andreou and Klostermeier (2013) J. Mol. Biol. 426:51-61). eIF4A has been shown to be important in the unwinding of structured 5'UTRs for translation initiation (Lawson et al. (1986) J. Biol. Chem. 261:13979-13989 and Parsyan et al. (2011) Nat. Rev. Mol. Cell Biol. 12:235-245). To test whether eIF4B and eIF4A are involved in the translational regulation of MYC in leukemic cells, multiple shRNAs were introduced against eIF4B or eIF4A into HPB-ALL cells. Notably, the knock-down efficiency of either eIF4B or eIF4A closely correlated with both the reduction of c-MYC protein levels in these cells, as well as the reduction of tumor cell proliferation (FIG. 7I-7L), indicating that both eIF4B and eIF4A are important in regulating the translation of c-MYC. To determine whether the phenotype observed in vitro can be replicated in vivo, the ability of the eIF4A shRNAs to suppress tumor growth and c-Myc protein levels in vivo was measured and confirmed (FIGS. 7M-7N). Taken together, the results demonstrate that in PTEN-deficient and c-MYC overexpressing T-ALL cells, the hyper-activated PI3K/mTORC1/S6K1 signaling axis is critical for the translation of elevated number of MYC transcripts bearing 5'UTR via an eIF4B/eIF4A mediated translational mechanism.

Example 7

Figure 9:
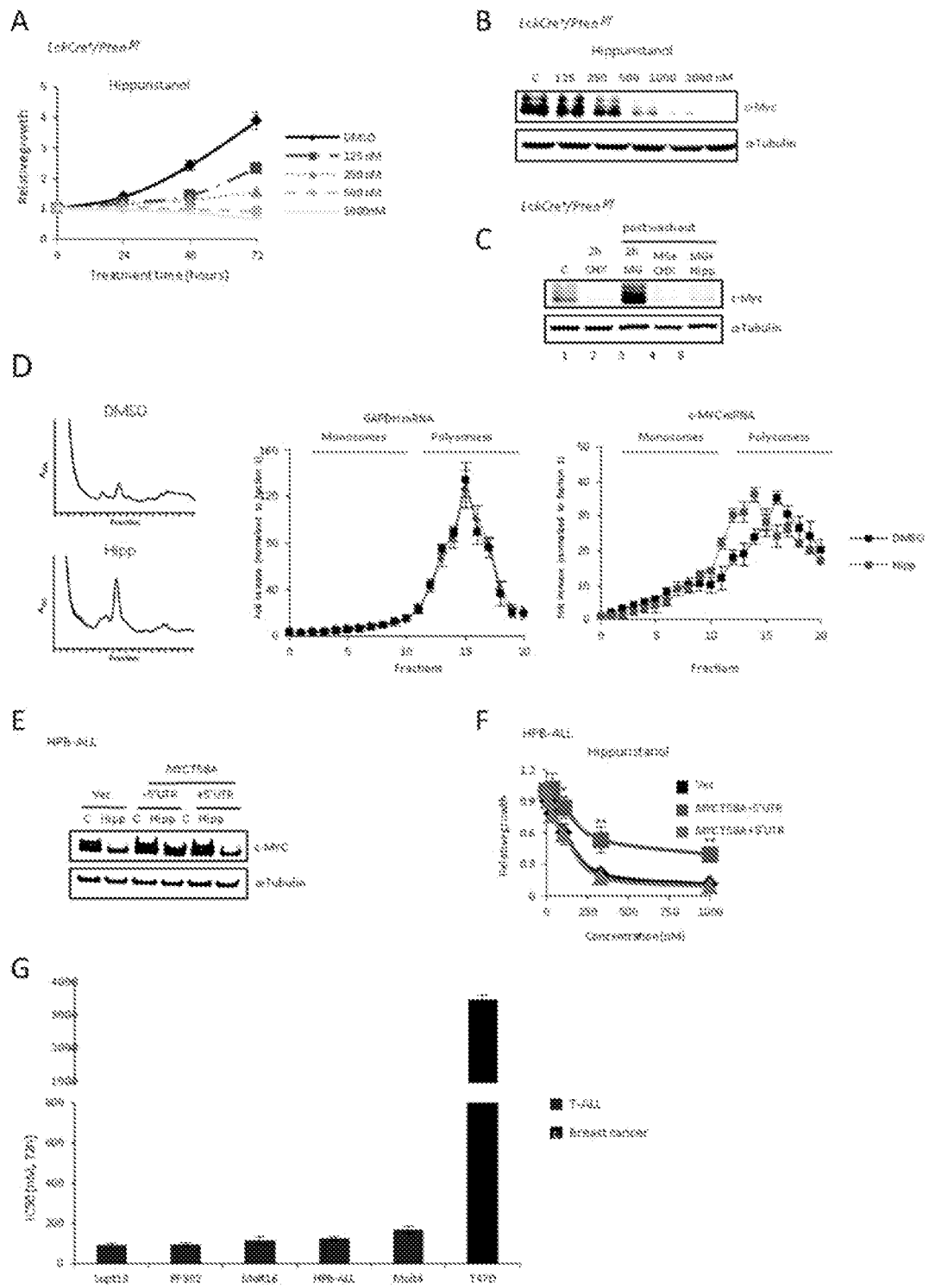
FIG. 9 includes 10 panels, identified as panels (A), (B), (C), (D), (E), (F), (G), (H), (I), and (J), which show that hippuristanol, a small molecule inhibitor of eIF4A, blocks the 5'UTR-dependent translation of c-MYC in T-ALL. Panel A shows the response of the growth rate of primary LckCre$^+$/Pten$^{f/f}$ T-ALL cells upon hippuristanol treatment. Hippuristanol was applied to cells at the indicated concentrations for the indicated hours before measurement. Panel B shows the response of the abundance of c-Myc in primary LckCre$^+$/Pten$^{f/f}$ T-ALL cells upon hippuristanol treatment. Hippuristanol was applied to cells at the indicated concentrations for two hours. DMSO treatment was used as negative control. Panel C shows that the de novo synthesis of c-Myc protein in primary LckCre$^+$/Pten$^{f/f}$ T-ALL cells is inhibited by hippuristanol treatment. Cells were pre-treated with 25 µg/ml CHX for two hours to deplete c-Myc protein (lanes 1-2), and subsequently washed three times with PBS to allow new biosynthesis. MG132 was then added at 10 µM either alone (lanes 3) or with 25 µg/ml CHX (lanes 4) or with 1 µM hippuristanol (lanes 5) for two hours. Panel D shows that c-MYC translation is inhibited by hippuristanol treatment. Polysome profiling assay was performed and fractions were collected. RT-PCR was performed to detect mRNA distribution. GAPDH mRNA was used as a control. Panel E shows the differential response of the c-MYC protein abundance in HPB-ALL cells expressing vector control, MYC T58A −5'UTR, or MYC T58A +5'UTR upon hippuristanol treatment. Cells were treated with 1 µM hippuristanol for two hours before being subjected to Western blotting analysis. Panel F shows the differential response of the growth rate of HPB-ALL cells expressing vector control, MYC T58A −5'UTR, or MYC T58A +5'UTR upon hippuristanol treatment. Cells were treated with 1 µM hippuristanol for seventy-two hours at indicated concentrations. DMSO treatment was used as a negative control. *P<0.05, **P<0.005 (n=3, Student's t test). Panel G shows that hippuristanol effectively inhibits cell proliferation of a panel of PTEN-deficient, c-MYC-high T-ALL cell lines with IC$_{50}$ in the nanomolar range. Cells were seeded into 96-well plates and hippuristanol was applied at concentration gradients. Seventy-two hours after the drug treatment, cell proliferation was measured by MTS assay with IC$_{50}$ values calculated using Prism 6. Panels H through J shows that recipient mice transplanted with two million primary human PTEN Mut T-All cells showed prolonged survival (Panel I) as compared to PTEN WT cells (Panel H) upon BKM120 treatment. c-Myc protein levels were also decreased as detected by Western blotting, (Panel J) after three days of BKM120 daily treatment (35 mg/kg), starting at 7 days post transplantation. PEG300 was used as control treatment for in vivo inhibitor administration.
Figure 9:
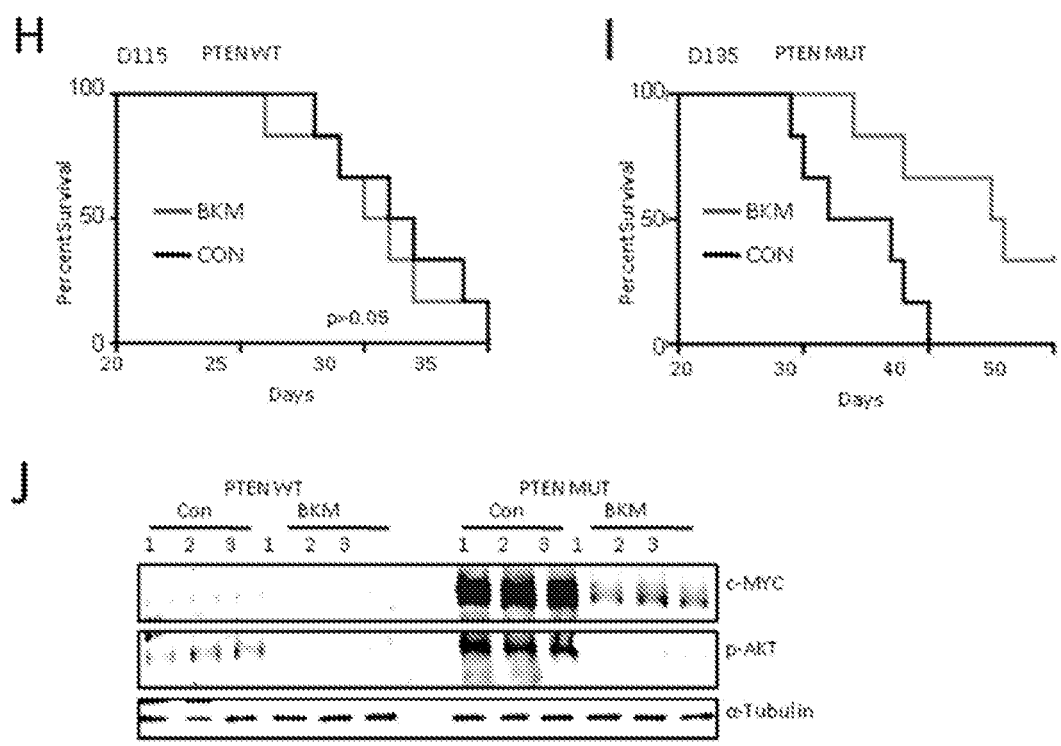

Hippuristanol, a Pharmacological Inhibitor of eIF4A, Blocks the Translation of c-MYC in Hematological Cancer Cells It was next determined whether the helicase activity of eIF4A is important for the translation control of MYC using hippuristanol, a selective enzymatic inhibitor of eIF4A (Bordeleau et al. (2006) Nat. Chem. Biol. 2:213-220). Primary Pten-null T-ALL cells isolated from LckCre⁺/Pten^f/f mice were tested and it was found that hippuristanol effectively reduced the c-Myc protein levels and the growth of these primary tumor cells in a dose-dependent manner (FIGS. 9A-9B). It was further confirmed that hippuristanol did not affect Myc transcription or degradation (FIGS. 10A-10B), but instead strongly blocked Myc translation (FIG. 9C).

Figure 10:
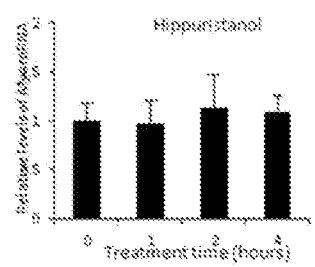
FIG. 10 includes 6 panels, identified as panels (A), (B), (C), (D), (E), and (F), which further show that hippuristanol, a small molecule inhibitor of eIF4A, blocks the 5'UTR-dependent translation of c-MYC in T-ALL. Panel A shows that the expression levels of c-Myc mRNA in primary T-ALL cells derived from LckCre$^+$/Pten$^{f/f}$ (mice remain unchanged upon 1 µM hippuristanol treatment at the indicated time points. c-Myc mRNA levels were measured by quantitative PCR. GAPDH was used as a control. Panel B shows that the c-Myc protein stability in primary T-ALL cells derived from LckCre$^+$/Pten$^{f/f}$ mice remained unchanged upon hippuristanol treatment for the indicated time points. Cells treated with 25 µg/ml cycloheximide (CHX) alone or with 1 µM hippuristanol are indicated. Panels C and D show the response of the abundance of c-Myc in PTEN-deficient T-ALL cells HPB-ALL (Panel C) and PF382 (Panel D) upon hippuristanol treatment. Hippuristanol was applied to cells at the indicated concentrations for two hours. DMSO treatment was used as a negative control. Panel E shows that the inhibition of eIF4A did not change the level of MYC transcription. HPB-ALL cells were treated with hippuristanol for one to four hours as indicated. c-MYC mRNA levels were measured by quantitative PCR. GAPDH was used as a control. Panel F shows that the c-MYC protein stability in HPB-ALL cells remained unchanged upon hippuristanol treatment for the indicated time points. Cells treated with 25 µg/ml cycloheximide (CHX) alone or with 1 µM hippuristanol are indicated.
Figure 10:
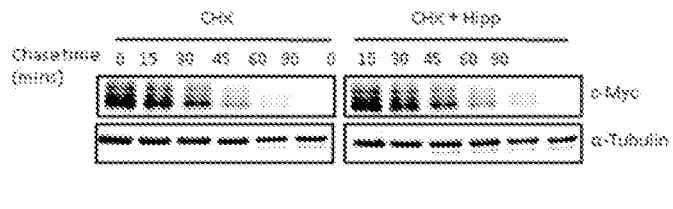
Figure 10:
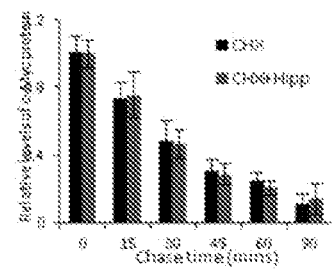
Figure 10:
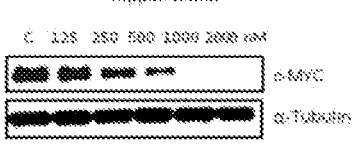
Figure 10:
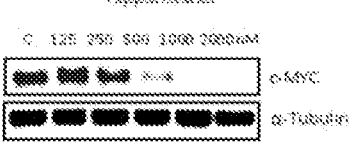
Figure 10:
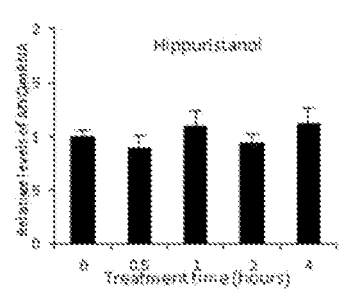
Figure 10:
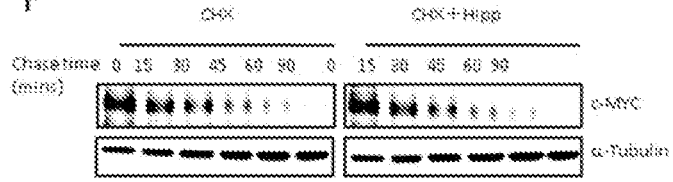
Figure 10:
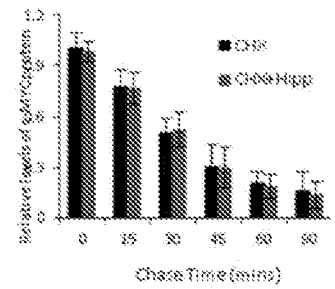

The results from the murine primary T-ALL model were also extended to human cancer cell lines. Consistent with the findings in primary LckCre⁺/Pten^f/f T-ALL, hippuristanol greatly reduced c-MYC protein levels in c-MYC dependent human T-ALL cell lines in a dose-dependent manner (FIGS. 10C-10D). It was also confirmed that hippuristanol prevented c-MYC translation without affecting its transcription or degradation (FIGS. 9D and 10E-10F).

To determine whether hippuristanol selectively targets the MYC 5'UTR, the isogenic cell lines, HPB-ALL MYC T58A −5'UTR and HPB-ALL MYC T58A +5'UTR, were treated with the inhibitor. While the c-MYC protein in HPB-ALL MYC T58A −5'UTR cells was little changed in response to hippuristanol treatment, c-MYC protein levels in both parental and HPB-ALL MYC T58A +5'UTR cells were markedly reduced in the presence of hippuristanol (FIG. 9E). Consistent with this finding, HPB-ALL MYC T58A −5'UTR cells were more resistant to growth inhibition induced by hippuristanol as compared to parental cells or the isogenic HPB-ALL MYC T58A +5'UTR (FIG. 9F). These data indicate that the unwinding of the structured 5'UTR of MYC mediated by the helicase activity of eIF4A is important for the translation of MYC. Furthermore, it was found that hippuristanol effectively inhibited the proliferation of a panel of human PTEN-deficient, c-MYC high T-ALL cell lines at relatively low concentrations (FIG. 9G).

To determine whether the phenotype observed in tumor models and cell lines can be replicated in human cell lines, the ability of the PI3K inhibitor BKM120 to suppress tumor growth and c-Myc protein levels in human patient samples in vivo was measured. As expected, the inhibition of PI3K in PTEN mutant primary patient line D135 prolonged mice survival and inhibited c-MYC protein level. In contrast, inhibition of PI3K doesn't affect mice survival in PTEN wide-type primary patient line D115 (FIGS. 9H-9J). These data collectively indicate the therapeutic potential of targeting eIF4A for T-ALLs dependent on pathologically activated c-MYC.

Most cases of T-ALL display upregulated expression of c-MYC, which frequently co-occurs with hyperactivation of the PI3K-AKT pathway, often through loss of PTEN (Gutierrez et al. (2009) *Blood* 114:647-650). However, the mechanistic link between the two events in this hematological malignancy has not been defined. Using a genetically engineered murine model of T-ALL driven by Pten-loss and featuring spontaneous overexpression of c-Myc, it has been determined herein that the abundance of c-Myc protein in this model is critically dependent on hyper-activated PI3K-Akt signaling. More specifically, it was found that the PI3K/mTORC1/S6K1 signaling axis robustly regulates the translation of MYC via a mechanism which requires the helicase activity of eIF4A to unwind the structured 5'UTR of MYC mRNA.

The results contrast with previous findings that c-MYC overexpression renders cells resistant to PI3K/mTOR inhibition (Clegg et al. (2011) *PLoS One* 6:e17449; Ilic et al. (2011) *Proc. Natl. Acad. Sci. U.S.A.* 108:E699-E708; and Liu et al. (2011) *Nat. Med.* 17:1116-1120). For example, in a murine model of breast cancer conditionally expressing human PIK3CA$^{H1047R}$, a fraction of the tumors which recurred after PIK3CA$^{H1047R}$ inactivation had focal amplifications of Myc, which led to independence of oncogenic PIK3CA and resistance to PI3K inhibition (Liu et al. (2011) *Nat. Med.* 17:1116-1120). The focal Myc amplicon in these recurrent tumors identified by a high density SNP analysis lacked exon 1 of Myc which encodes the Myc 5'UTR (Liu et al. (2011) *Nat. Med.* 17:1116-1120). Consistently, the c-Myc protein levels in these mammary tumor cells were not altered in response to PI3K inhibition. Together these findings indicate that the presence or absence of MYC 5'UTR serves as a biomarker for predicting drug responses of c-MYC-dependent tumors to inhibition of the PI3K/mTORC1/S6K1 signaling axis (e.g., PI3K inhibition) in human patients.

When activated, mTORC1 is known to regulate a number of translation initiation factors that are essential for translation, including eIF4E and eIF4B (Sonenberg and Hinnebusch (2009) *Cell* 136:731-745). mTORC1 phosphorylates eIF4E-binding protein (4EBP1), an event that renders eIF4E available for binding to eIF4G and consequently, recognition of 5' cap by the eIF4F complex (Sonenberg and Hinnebusch (2009) *Cell* 136:731-745 and Zoncu et al. (2011) *Nat. Rev. Mol. Cell Biol.* 12:21-35). Another critical downstream factor of mTORC1 is S6K1. Upon activation, S6K1 phosphorylates eIF4B on Ser 422 to facilitate the translation initiation (Holz et al. (2005) *Cell* 123:569-580; Raught et al. (2004) *EMBO J.* 23:1761-1769; Shahbazian et al. (2006) *EMBO J.* 25:2781-2791; and Shahbazian et al. (2010) *Mol. Cell Biol.* 30:1478-1485). eIF4B is a cofactor of the RNA helicase eIF4A which is known to be critical for unwinding structured 5'UTRs. It has been previously shown that eIF4A alone has low helicase activity but its activity can be significantly enhanced by binding to the phosphorylated eIF4B (Parsyan et al. (2011) *Nat. Rev. Mol. Cell Biol.* 12:235-245). In addition, S6K1 phosphorylates and destabilizes PDCD4 (Dorrello et al. (2006) *Science* 314:467-471), an eIF4A-binding protein that inhibits protein translation (Yang et al. (2003) *Mol. Cell Biol.* 23:26-37). While both eIF4E and eIF4B have been previously implicated in the regulation of c-Myc (Moerke et al. (2007) *Cell* 128:257-267 and Shahbazian et al. (2010) *Mol. Cell Biol.* 30:1478-1485), the results described herein demonstrate a robust translational regulation of MYC through the PI3K-mTORC1-S6K1 signaling axis that activates the eIF4B/eIF4A initiation complex generally in hematologic malignancies dependent on c-MYC overexpression.

Aberrant transcriptional overexpression of c-MYC occurs in most cases of both human T-ALL and murine T-ALL models, often downstream of mutational activation of NOTCH1 in humans or Myc chromosomal rearrangements in mice (Guo et al. (2008) *Nature* 453:529-533; Guo et al. (2011) *Proc. Natl. Acad. Sci. U.S.A.* 108:1409-1414; Liu et al. (2010) *J. Clin. Invest.* 120:2497-2507; Weng et al. (2006) *Genes Dev.* 20:2096-2109; and Zhang et al. (2011) *Leukemia* 25:1857-1868). However, the protein abundance of c-MYC is highly variable in T-ALL (Bonnet et al. (2011) *Blood* 117:6650-6659), indicating that post-transcriptional regulation of c-MYC constitutes a major alternative mechanism of c-MYC activation in T-ALL. In line with this, previous studies have indicated that upregulation of Myc mRNA expression was not sufficient to induce lymphomagenesis (Hemann et al. (2005) *Nature* 436:807-811). It has been proposed that c-MYC protein abundance can be modulated by stability of c-MYC via phosphorylation status of T58 regulated by GSK3β (Bonnet et al. (2011) *Blood* 117:6650-6659; Gulati et al. (2008) *Cell Metab.* 7:456-465; and Zhang et al. (2006) *Mol. Cell* 24:185-197). Despite the presence of overexpressed MYC transcripts or MYC stabilizing mutations, as found in Burkitt lymphomas (Albert et al. (1994) *Oncogene* 9:759-763; Bhatia et al. (1993) *Nat. Genet.* 5:56-61; Bhatia et al. (1994) *Blood* 84:883-888; Brennscheidt et al. (1994) *Leukemia* 8:897-902; Johnston et al. (1991) *Blood* 78:2419-2425; and Yano et al. (1993) *Oncogene* 8:2741-2748), it is demonstrated herein that PTEN-PI3K-dependent de novo synthesis of c-MYC protein is essential for sustaining the high abundance of c-MYC protein, as well as for proliferation of these leukemia cells. Thus, PTEN acts like a critical "gatekeeper" on this rate-limiting step in c-MYC biosynthesis.

Despite extensive efforts to target c-MYC for cancer therapy, direct inhibition of c-MYC protein has so far been unsuccessful (Darnell (2002) *Nat. Rev. Cancer* 2:740-749). Recent studies in hematological cancers have revealed a novel strategy of targeting c-MYC via suppression of its transcription through inactivation of BRD4 (Delmore et al. (2011) *Cell* 146:904-917 and Mertz et al. (2011) *Proc. Natl. Acad. Sci. U.S.A.* 108:16669-16674). These findings indicate that regulating MYC at the transcriptional level or other levels may result in clinical benefit. It is demonstrated herein that inhibition of c-MYC translation can also effectively suppress c-MYC protein synthesis and hematological tumor growth, providing novel avenues to target undruggable oncogenic lesions via suppression of their druggable regulators. Numerous pharmacological inhibitors targeting PI3K, AKT, mTORC1 or S6K1 are already in pre- and clinical development for cancer treatment (Liu et al. (2009) *Nat. Rev. Drug Discov.* 8:627-644). A number of mTOR inhibitors, e.g., rapamycin and RAD001, have received FDA approval for clinical use (Lebwohl et al. (2013) *Ann. N.Y. Acad. Sci.* 1291:14-32). Based on the results presented herein, it is believed that these drugs could be highly effective in treating T-ALL patients, an idea with the potential for a fast and meaningful translational outcome.

Such results also elucidate the effect of the eIF4A inhibitor, hippuristanol. Hippuristanol has been shown to inhibit the proliferation of HTLV-1-infected T-cell lines and ATL cells in vitro (Tsumuraya et al. (2011) *Biochem. Pharmacol.* 81:713-722) as well as to reduce the viability of primary effusion lymphoma cells both in vitro and in vivo (Ishikawa et al. (2013) *Mar. Drugs* 11:3410-3424). It was also reported to sensitize B cell malignancies to chemotherapy (Cencic et al. (2013) *Blood Cancer J.* 3:e128). Based on the results described herein, it is believed that these observed effects of hippuristanol are mediated via the translational inhibition of c-MYC. Other small molecules targeting eIF4A, such as pateamine A (Romo et al. (2000) *Ernst Schering Res. Found Workshop* 32:103-148), silvestrol (Hwang et al. (2004) *J. Org. Chem.* 69:3350-3358) and the rocaglamides (Sadlish et al. (2013) *ACS Chem. Biol.* 8:1519-1527) may therefore also inhibit c-MYC translation and targeting c-MYC translation through eIF4A may be applicable to solid tumors as well.

Targeting translational components for cancer therapy has received less attention compared to other molecular targets critical for transcriptional regulation or posttranslational modifications. One of the reasons might be the potential lack of selectivity of this approach (Robert and Pelletier (2009) *Expert Opin. Ther. Targets* 13:1279-1293). In the classic model of translational control by mTORC1, global translational regulation is achieved via phosphorylation of downstream factor 4EBP1, which binds to and inhibits the activity of eIF4E, a more general mechanism of translational control (Laplante and Sabatini (2012) *Cell* 149:274-293). The results described herein indicate that certain oncoproteins, such as c-MYC, contain specific structured 5'UTRs and selective targeting may be achievable by inhibiting a less general factor, eIF4A, in translational control. It is believed that targeting eIF4A would likely be more specific and less toxic, especially in tumors such as T-ALL where the MYC transcripts is greatly overexpressed.

The effective inhibition of PTEN-deficient hematological malignancies by suppression of eIF4A can also provide another therapeutic strategy to target PTEN-deficient tumors. PTEN is one of the most frequently deregulated tumor suppressors in various human cancers. Despite the large effort to target PTEN-deficient tumors using PI3K inhibitors, many PTEN-deficient tumors remain insensitive to PI3K inhibition or develop resistance after a short period of exposure (Ilic et al. (2011) *Proc. Natl. Acad. Sci. U.S.A.* 108:E699-E708; Liu et al. (2011) *Nat. Med.* 17:1116-1120; O'Brien et al. (2010) *Clin. Cancer Res.* 16:3670-3683; and Tenbaum et al. (2012) *Nat. Med.* 18:892-901). The results described herein demonstrate a promising alternative approach to target PTEN-deficient hematological malignancies.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a human subject afflicted with T cell acute lymphoblastic leukemia characterized by reduced Pten function and amplification or overexpression of a c-Myc transcript comprising a 5'-untranslated region (5'-UTR) relative to a normal control, comprising administering to the subject an inhibitor of eukaryotic initiation factor-4A (eIF4A) and/or an inhibitor of eukaryotic initiation factor-4B (eIF4B), wherein the inhibitor is selected from the group consisting of RNA interference-mediating nucleic acids that bind eIF4A or eIF4B, hippuristanol, pateamine A, silvestrol, and rocaglamides, thereby treating the subject.

2. The method of claim 1, wherein
   i) the efficacy of the treatment is measured by at least one criteria selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria; and/or ii) the inhibitor of eIF4A and/or eIF4B is administered in a pharmaceutically acceptable formulation.

3. The method of claim 1, wherein the eIF4A and/or eIF4B is selected from the group consisting of human eukaryotic initiation factor-4A (eIF4A) or an ortholog thereof, and human eukaryotic initiation factor-4B (eIF4B) or an ortholog thereof.

4. The method of claim 1, further comprising administering one or more additional anti-cancer agents.

* * * * *

SEQUENCE LISTING

```
<160> NUMBER OF SEQ ID NOS: 46

<210> SEQ ID NO 1
<211> LENGTH: 525
<212> TYPE: DNA
<213> ORGANISM: Homo sapiens

<400> SEQUENCE: 1 gaccccgag ctgtgctgct cgcggccgcc accgccgggc cccggccgtc cctggctccc      60
ctcctgcctc gagaagggca gggcttctca gaggcttggc gggaaaaaga acggagggag    120
```

```
ggatcgcgct gagtataaaa gccggttttc ggggctttat ctaactcgct gtagtaattc    180
cagcgagagg cagagggagc gagcgggcgg ccggctaggg tggaagagcc gggcgagcag    240
agctgcgctg cgggcgtcct gggaagggag atccggagcg aataggggc ttcgcctctg    300 gcccagccct cccgctgatc ccccagccag cggtccgcaa cccttgccgc atccacgaaa    360 cttttgcccat agcagcgggc gggcactttg cactggaact acaacaccc gagcaaggac    420 gcgactctcc cgacgcgggg aggctattct gcccatttgg ggacacttcc ccgccgctgc    480
caggacccgc ttctctgaaa ggctctcctt gcagctgctt agacg                   525
```

<210> SEQ ID NO 2
<211> LENGTH: 626
<212> TYPE: DNA
<213> ORGANISM: Mus musculus

<400> SEQUENCE: 2

```
cccgcccacc cgcccttat attccggggg tctgcgcggc cgaggacccc tgggctgcgc     60
tgctctcagc tgccgggtcc gactcgcctc actcagctcc cctcctgcct cctgaagggc    120
agggcttcgc cgacgcttgg cgggaaaaag aagggagggg agggatcctg agtcgcagta    180 taaagaagc ttttcgggcg ttttttttctg actcgctgta gtaattccag cgagagacag    240
agggagtgag cggacggttg gaagagccgt gtgtgcagag ccgcgctccg ggcgaccta    300 agaaggcagc tctggagtga gaggggcttt gcctccgagc ctgccgccca ctctccccaa    360
ccctgcgact gacccaacat cagcggccgc aaccctcgcc gccgctggga aactttgccc    420
attgcagcgg gcagacactt ctcactggaa cttacaatct gcgagccagg acaggactcc    480
ccaggctccg gggagggaat ttttgtctat ttggggacag tgttctctgc ctctgcccgc    540
gatcagctct cctgaaaaga gctcctcgag ctgtttgaag gctggatttc ctttgggcgt    600
tggaaacccc gcagacagcc acgacg                                         626
```

<210> SEQ ID NO 3
<211> LENGTH: 536
<212> TYPE: DNA
<213> ORGANISM: Rattus norvegicus

<400> SEQUENCE: 3

```
accccggggc tgcgctgctc tccgctgccg cctccgccgc gcccactccg ctcgcctcct     60
gcctccaaaa gggcagggct tcgccgaggc ttggcgggaa aaagaagcga ggggagggat    120
ccggagtcgc agtataaaag aagcttttcg ggcgtttttt ttctgactcg ctgtagtaat    180
tccagcgaga gacagaggga gtgagcggc gggttggaag agcccagtgt gcagagcccc    240
actccgggct tcctaggaag gcagctctgg agtgagaagg gctttgcctc caggcttgct    300
gcctcctcga cccaatcctc ccgctgaccc aacatcagcg gtcgcaaccc tcgccgcctc    360
tgggaaactt tgcccattgc aacgggcaga cacttctcac tggaacttac aatctgcgag    420
ccaggacagg actccccagg cgcaggggag ggaattttg tctatttggg gacagtgttc    480
tctgcctctg cccgcgatcg gctcccctga aaagagctcc tcgcgttatt tgaagc        536
```

<210> SEQ ID NO 4
<211> LENGTH: 592
<212> TYPE: DNA
<213> ORGANISM: Sus scrofa

<400> SEQUENCE: 4

```
tataggcgag ggtctgcgcg gctggggacc ctccggctgc gcatctctcg gctgccgccg     60
```

```
ccttttgccgc accccggcca ccgctaggct ccccactgcc tctggaaggg cagggctata    120
cagaggcttg gcgggaaaaa gagcacggag gggaggggtg ttcctagcag tataaaagcc    180
ggttttctgg gctttctctg actcgctgta gtaattccag cgagaggcag agggagcgag    240
cgggcgggcc ctccagggtg gaagagcaga gccggccgca caatctgagt cgcgctctgg    300
gcgcccgggg gaagggagat ccggagtgaa agagggtctt cgcctccgtc ccggccgccc    360
ccaccccacc ctgcccgccg acccctgcca gcggtccgcc accgcgccg catccacgaa      420 actttgccca ctgcagcggg cgggtacttt ccactggaac ttacaacacc cgagcgacaa    480
cgcgactctc cggacgcgga gaggctattc tgcctatttg gggagacact tttccctgtc    540
gctgcccacg actcgctcct ctgaaaggcg ctcctcgccg cttttttggac gc            592
```

```
<210> SEQ ID NO 5
<211> LENGTH: 1221
<212> TYPE: DNA
<213> ORGANISM: Homo sapiens

<400> SEQUENCE: 5
atgtctgcga gccaggattc ccgatccaga gacaatggcc ccgatgggat ggagcccgaa     60
ggcgtcatcg agagtaactg gaatgagatt gttgacagct ttgatgacat gaacctctcg    120
gagtcccttc tccgtggcat ctacgcgtat ggtttttgaga agccctctgc catccagcag    180
cgagccattc taccttgtat caagggttat gatgtgattg ctcaagccca atctgggact    240
gggaaaacgg ccacatttgc catatcgatt ctgcagcaga ttgaattaga tctaaaagcc    300
acccaggcct tggtcctagc acccactcga gaattggctc agcagataca gaaggtggtc    360
atggcactag gagactacat gggcgcctcc tgtcacgcct gtatcggggg caccaacgtg    420
cgtgctgagg tgcagaaact gcagatgaaa gctccccaca tcatcgtggg tacccctggc    480 cgtgtgttg atatgcttaa ccggagatac ctgtccccca aatacatcaa gatgtttgta    540
ctggatgaag ctgacgaaat gttaagccgt ggattcaagg accagatcta tgacatattc    600
caaaagctca acagcaacac ccaggtagtt ttgctgtcag ccacaatgcc ttctgatgtg    660
cttgaggtga ccaagaagtt catgaggggac cccattcgga ttcttgtcaa gaaggaagag    720
ttgaccctgg agggtatccg ccagttctac atcaacgtgg aacgagagga gtggaagctg    780
gacacactat gtgacttgta tgaaaccctg accatcaccc aggcagtcat cttcatcaac    840
acccggagga aggtggactg gctcaccgag aagatgcatg ctcgagattt cactgtatcc    900
gccatgcatg gagatatgga ccaaaaggaa cgagacgtga ttatgaggga gtttcgttct    960
ggctctagca gagttttgat taccactgac ctgctggcca gaggcattga tgtgcagcag   1020
gtttctttag tcatcaacta tgaccttccc accaacaggg aaaactatat ccacagaatc   1080
ggtcgaggtg gacggtttgg ccgtaaaggt gtggctatta catggtgacg agaagaagac   1140
aagaggactc ttcgagacat tgagaccttc tacaacacct ccattgagga aatgccctc    1200 aatgttgctg acctcatctg a                                              1221
```

```
<210> SEQ ID NO 6
<211> LENGTH: 406
<212> TYPE: PRT
<213> ORGANISM: Homo sapiens

<400> SEQUENCE: 6

Met Ser Ala Ser Gln Asp Ser Arg Ser Arg Asp Asn Gly Pro Asp Gly
 1               5                  10                  15
```

Met Glu Pro Glu Gly Val Ile Glu Ser Asn Trp Asn Glu Ile Val Asp
            20                  25                  30

Ser Phe Asp Asp Met Asn Leu Ser Glu Ser Leu Leu Arg Gly Ile Tyr
        35                  40                  45

Ala Tyr Gly Phe Glu Lys Pro Ser Ala Ile Gln Gln Arg Ala Ile Leu
    50                  55                  60

Pro Cys Ile Lys Gly Tyr Asp Val Ile Ala Gln Ala Gln Ser Gly Thr
65                  70                  75                  80

Gly Lys Thr Ala Thr Phe Ala Ile Ser Ile Leu Gln Gln Ile Glu Leu
                85                  90                  95

Asp Leu Lys Ala Thr Gln Ala Leu Val Leu Ala Pro Thr Arg Glu Leu
            100                 105                 110

Ala Gln Gln Ile Gln Lys Val Val Met Ala Leu Gly Asp Tyr Met Gly
        115                 120                 125

Ala Ser Cys His Ala Cys Ile Gly Gly Thr Asn Val Arg Ala Glu Val
    130                 135                 140

Gln Lys Leu Gln Met Glu Ala Pro His Ile Ile Val Gly Thr Pro Gly
145                 150                 155                 160

Arg Val Phe Asp Met Leu Asn Arg Arg Tyr Leu Ser Pro Lys Tyr Ile
                165                 170                 175

Lys Met Phe Val Leu Asp Glu Ala Asp Glu Met Leu Ser Arg Gly Phe
            180                 185                 190

Lys Asp Gln Ile Tyr Asp Ile Phe Gln Lys Leu Asn Ser Asn Thr Gln
        195                 200                 205

Val Val Leu Leu Ser Ala Thr Met Pro Ser Asp Val Leu Glu Val Thr
    210                 215                 220

Lys Lys Phe Met Arg Asp Pro Ile Arg Ile Leu Val Lys Lys Glu Glu
225                 230                 235                 240

Leu Thr Leu Glu Gly Ile Arg Gln Phe Tyr Ile Asn Val Glu Arg Glu
                245                 250                 255

Glu Trp Lys Leu Asp Thr Leu Cys Asp Leu Tyr Glu Thr Leu Thr Ile
            260                 265                 270

Thr Gln Ala Val Ile Phe Ile Asn Thr Arg Arg Lys Val Asp Trp Leu
        275                 280                 285

Thr Glu Lys Met His Ala Arg Asp Phe Thr Val Ser Ala Met His Gly
    290                 295                 300

Asp Met Asp Gln Lys Glu Arg Asp Val Ile Met Arg Glu Phe Arg Ser
305                 310                 315                 320

Gly Ser Ser Arg Val Leu Ile Thr Thr Asp Leu Leu Ala Arg Gly Ile
                325                 330                 335

Asp Val Gln Gln Val Ser Leu Val Ile Asn Tyr Asp Leu Pro Thr Asn
            340                 345                 350

Arg Glu Asn Tyr Ile His Arg Ile Gly Arg Gly Gly Arg Phe Gly Arg
        355                 360                 365

Lys Gly Val Ala Ile Asn Met Val Thr Glu Glu Asp Lys Arg Thr Leu
    370                 375                 380

Arg Asp Ile Glu Thr Phe Tyr Asn Thr Ser Ile Glu Glu Met Pro Leu
385                 390                 395                 400

Asn Val Ala Asp Leu Ile
            405

<210> SEQ ID NO 7
<211> LENGTH: 1044

<212> TYPE: DNA
<213> ORGANISM: Homo sapiens

<400> SEQUENCE: 7

```
atgtctgcga gccaggattc ccgatccaga gacaatggcc ccgatgggat ggagcccgaa      60
ggcgtcatcg agagtaactg gaatgagatt gttgacagct tgatgacat gaacctctcg     120
gagtcccttc tccgtggcat ctacgcgtat ggttttgaga agccctctgc catccagcag    180
cgagccattc taccttgtat caagggttat gatgtgattg ctcaagccca atctgggact    240
gggaaaacgg ccacatttgc catatcgatt ctgcagcaga ttgaattaga tctaaaagcc    300
acccaggcct tggtcctagc acccactcga gaattggctc agcagataca aaggtggtc     360
atggcactag gagactacat gggcgcctcc tgtcacgcct gtatcggggg caccaacgtg    420
cgtgctgagg tgcagaaact gcagatggaa gctccccaca tcatcgtggg tacccctggc    480
cgtgtgtttg atatgcttaa ccggagatac ctgtccccca atacatcaa gatgtttgta     540
ctggatgaag ctgacgaaat gttaagccgt ggattcaagg accagatcta tgacatattc    600
caaaagctca acagcaacac ccaggtagtt ttgctgtcag ccacaatgcc ttctgatgtg    660
cttgaggtga ccaagaagtt catgagggac cccattcgga ttcttgtcaa gaaggaagag    720
ttgaccctgg agggtatccg ccagttctac atcaacgtgg aacgagagga gtggaagctg    780
gacacactat gtgacttgta tgaaaccctg accatcaccc aggcagtcat cttcatcaac    840
acccggagga aggtggactg gctcaccgag aagatgcatg ctcgagattt cactgtatcc    900
gccatgcatg gagatatgga ccaaaaggaa cgagacgtga ttatgaggga gtttcgttct    960
ggctctagca gagttttgat taccactgac ctgctgggaa aactatatcc acagaatcgg   1020
tcgaggtgga cggtttggcc gtaa                                            1044
```

<210> SEQ ID NO 8
<211> LENGTH: 347
<212> TYPE: PRT
<213> ORGANISM: Homo sapiens

<400> SEQUENCE: 8

```
Met Ser Ala Ser Gln Asp Ser Arg Ser Arg Asp Asn Gly Pro Asp Gly
1               5                   10                  15

Met Glu Pro Glu Gly Val Ile Glu Ser Asn Trp Asn Glu Ile Val Asp
                20                  25                  30

Ser Phe Asp Asp Met Asn Leu Ser Glu Ser Leu Leu Arg Gly Ile Tyr
            35                  40                  45

Ala Tyr Gly Phe Glu Lys Pro Ser Ala Ile Gln Gln Arg Ala Ile Leu
        50                  55                  60

Pro Cys Ile Lys Gly Tyr Asp Val Ile Ala Gln Ala Gln Ser Gly Thr
65                  70                  75                  80

Gly Lys Thr Ala Thr Phe Ala Ile Ser Ile Leu Gln Gln Ile Glu Leu
                85                  90                  95

Asp Leu Lys Ala Thr Gln Ala Leu Val Leu Ala Pro Thr Arg Glu Leu
            100                 105                 110

Ala Gln Gln Ile Gln Lys Val Val Met Ala Leu Gly Asp Tyr Met Gly
        115                 120                 125

Ala Ser Cys His Ala Cys Ile Gly Gly Thr Asn Val Arg Ala Glu Val
    130                 135                 140

Gln Lys Leu Gln Met Glu Ala Pro His Ile Ile Val Gly Thr Pro Gly
145                 150                 155                 160
```

```
Arg Val Phe Asp Met Leu Asn Arg Arg Tyr Leu Ser Pro Lys Tyr Ile
            165                 170                 175

Lys Met Phe Val Leu Asp Glu Ala Asp Glu Met Leu Ser Arg Gly Phe
        180                 185                 190

Lys Asp Gln Ile Tyr Asp Ile Phe Gln Lys Leu Asn Ser Asn Thr Gln
            195                 200                 205

Val Val Leu Leu Ser Ala Thr Met Pro Ser Asp Val Leu Glu Val Thr
        210                 215                 220

Lys Lys Phe Met Arg Asp Pro Ile Arg Ile Leu Val Lys Lys Glu Glu
225                 230                 235                 240

Leu Thr Leu Glu Gly Ile Arg Gln Phe Tyr Ile Asn Val Glu Arg Glu
                245                 250                 255

Glu Trp Lys Leu Asp Thr Leu Cys Asp Leu Tyr Glu Thr Leu Thr Ile
            260                 265                 270

Thr Gln Ala Val Ile Phe Ile Asn Thr Arg Arg Lys Val Asp Trp Leu
        275                 280                 285

Thr Glu Lys Met His Ala Arg Asp Phe Thr Val Ser Ala Met His Gly
    290                 295                 300

Asp Met Asp Gln Lys Glu Arg Asp Val Ile Met Arg Glu Phe Arg Ser
305                 310                 315                 320

Gly Ser Ser Arg Val Leu Ile Thr Thr Asp Leu Leu Gly Lys Leu Tyr
                325                 330                 335

Pro Gln Asn Arg Ser Arg Trp Thr Val Trp Pro
            340                 345
```

```
<210> SEQ ID NO 9
<211> LENGTH: 1221
<212> TYPE: DNA
<213> ORGANISM: Mus musculus

<400> SEQUENCE: 9
atgtctgcga gtcaggattc tcgatccaga gacaatggcc ccgacgggat ggagccggaa      60
ggcgtcatcg agagtaactg aacgagatt gtggatagct ttgatgacat gaatctctca     120
gagtccctcc tccgtggtat ttatgccat ggttttgaga agccctctgc catccagcag     180
cgagctattc ttccttgtat caagggttat gatgtgattg ctcaagccca gtctgggact     240
gggaaaacag ctacatttgc catatcaatt ctgcagcaga ttgaattaga tctaaaggcc     300
actcaggctt tggttctggc acccacacgt gaattggctc agcagataca aaaggtggtt     360
atggcattag agactacat gggtgcctct tgtcatgcct gcattggggg caccaatgtg     420
cgtgctgagg tgcagaagct gcagatggaa gctccccata tcatcgtggg taccctggc     480 cgggtgtttg acatgcttaa ccggagatac ctgtccccca aatacatcaa gatgttcgta     540
ctggatgaag cagatgaaat gttaagccga gggttcaagg atcagatcta tgacatattc     600
cagaagctca cagcaacac acaggtagtt ttgttgtctg ctacaatgcc ttctgatgtc     660
cttgaggtga ccaagaaatt tatgagagac cctattcgga ttcttgtcaa gaaggaagaa     720
ttgaccctgg agggtatccg ccaattctac atcaatgtgg aacgagagga gtggaagctt     780
gacacattgt gtgacttgta tgagacgctg accatcaccc aggcagtcat ctttatcaac     840
accagaagga aggtggactg gctcaccgag aagatgcatg cccgagattt cactgtttct     900
gccatgcacg gagatatgga ccaaaaggaa cgagatgtga tcatgaggga gttccggtct     960
ggctctagca gagtattaat taccactgac ctgttggcca gagcattga tgtgcagcag    1020 gtctccttag tcatcaacta tgaccttccc accaacaggg aaaactacat ccacagaatc    1080
```

```
ggtcgaggtg gtcggtttgg tcgtaagggt gtggctatta acatggtgac cgaagaagac    1140
aagaggactc ttcgagacat tgagactttc tacaacacct ccattgaaga gatgcccctc    1200
aacgttgctg acctcatttg a                                              1221
```

<210> SEQ ID NO 10
<211> LENGTH: 406
<212> TYPE: PRT
<213> ORGANISM: Mus musculus

<400> SEQUENCE: 10

```
Met Ser Ala Ser Gln Asp Ser Arg Ser Arg Asp Asn Gly Pro Asp Gly
1               5                   10                  15

Met Glu Pro Glu Gly Val Ile Glu Ser Asn Trp Asn Glu Ile Val Asp
                20                  25                  30

Ser Phe Asp Asp Met Asn Leu Ser Glu Ser Leu Leu Arg Gly Ile Tyr
            35                  40                  45

Ala Tyr Gly Phe Glu Lys Pro Ser Ala Ile Gln Gln Arg Ala Ile Leu
        50                  55                  60

Pro Cys Ile Lys Gly Tyr Asp Val Ile Ala Gln Ala Gln Ser Gly Thr
65                  70                  75                  80

Gly Lys Thr Ala Thr Phe Ala Ile Ser Ile Leu Gln Gln Ile Glu Leu
                85                  90                  95

Asp Leu Lys Ala Thr Gln Ala Leu Val Leu Ala Pro Thr Arg Glu Leu
            100                 105                 110

Ala Gln Gln Ile Gln Lys Val Val Met Ala Leu Gly Asp Tyr Met Gly
        115                 120                 125

Ala Ser Cys His Ala Cys Ile Gly Gly Thr Asn Val Arg Ala Glu Val
    130                 135                 140

Gln Lys Leu Gln Met Glu Ala Pro His Ile Ile Val Gly Thr Pro Gly
145                 150                 155                 160

Arg Val Phe Asp Met Leu Asn Arg Arg Tyr Leu Ser Pro Lys Tyr Ile
                165                 170                 175

Lys Met Phe Val Leu Asp Glu Ala Asp Glu Met Leu Ser Arg Gly Phe
            180                 185                 190

Lys Asp Gln Ile Tyr Asp Ile Phe Gln Lys Leu Asn Ser Asn Thr Gln
        195                 200                 205

Val Val Leu Leu Ser Ala Thr Met Pro Ser Asp Val Leu Glu Val Thr
    210                 215                 220

Lys Lys Phe Met Arg Asp Pro Ile Arg Ile Leu Val Lys Lys Glu Glu
225                 230                 235                 240

Leu Thr Leu Glu Gly Ile Arg Gln Phe Tyr Ile Asn Val Glu Arg Glu
                245                 250                 255

Glu Trp Lys Leu Asp Thr Leu Cys Asp Leu Tyr Glu Thr Leu Thr Ile
            260                 265                 270

Thr Gln Ala Val Ile Phe Ile Asn Thr Arg Arg Lys Val Asp Trp Leu
        275                 280                 285

Thr Glu Lys Met His Ala Arg Asp Phe Thr Val Ser Ala Met His Gly
    290                 295                 300

Asp Met Asp Gln Lys Glu Arg Asp Val Ile Met Arg Glu Phe Arg Ser
305                 310                 315                 320

Gly Ser Ser Arg Val Leu Ile Thr Thr Asp Leu Leu Ala Arg Gly Ile
                325                 330                 335

Asp Val Gln Gln Val Ser Leu Val Ile Asn Tyr Asp Leu Pro Thr Asn
```

```
                340             345             350
Arg Glu Asn Tyr Ile His Arg Ile Gly Arg Gly Gly Arg Phe Gly Arg
            355             360             365

Lys Gly Val Ala Ile Asn Met Val Thr Glu Glu Asp Lys Arg Thr Leu
        370             375             380

Arg Asp Ile Glu Thr Phe Tyr Asn Thr Ser Ile Glu Glu Met Pro Leu
385             390             395             400

Asn Val Ala Asp Leu Ile
            405

<210> SEQ ID NO 11
<211> LENGTH: 1221
<212> TYPE: DNA
<213> ORGANISM: Pan troglodytes

<400> SEQUENCE: 11
atgtctgcga gccaggattc ccgatccaga gacaatggcc ccgatgggat ggagcccgaa      60
ggcgtcatcg agagtaactg gaatgagatt gttgacagct tgatgacat gaacctctcg     120
gagtcccttc tccgtggtat ctacgcctat ggttttgaga agccctctgc catccagcag     180
cgagccattc taccttgtat caagggttat gatgtgattg ctcaagccca atctgggact     240
gggaaaacgg ccacatttgc catatcgatt ctgcagcaga ttgaattaga tctaaaagcc     300
acccaggcct tggtcctagc acccactcga gaattggctc agcagataca aaggtggtc     360
atggcattag agactacat gggcgcctcc tgtcacgcct gtatcggggg caccaacgtg     420
cgtgctgagt gcagaaaact gcagatggaa gctccccaca tcatcgtggg tacccctggc     480
cgtgtgtttg atatgcttaa ccggagatac ctgtcccccca gtacatcaa gatgtttgta     540
ctggatgaag ctgacgaaat gttaagccgt ggattcaagg accagatcta tgacatattc     600
caaaagctca acagcaacac ccaggtagtt ttgctgtcag ccacaatgcc ttctgatgtg     660
cttgaggtga ccaagaagtt catgagggac cccattcgga ttctcgtcaa gaaggaagag     720
ttgaccctgg agggtatccg ccagttctac atcaacgtgg aacgagagga gtggaagctg     780
gacacactat gtgacttgta tgaaaccctg accatcaccc aggcagtcat cttcatcaac     840
acccggagga aggtggactg gctcaccgag aagatgcatg ctcgagattt cactgtatcc     900
gccatgcatg gagatatgga ccaaaaggaa cgagacgtga tcatgaggga gtttcgttct     960
ggctctagca gagttttgat taccactgac ctgctggcca gaggcattga tgtgcagcag    1020
gtttctttag tcatcaacta tgaccttccc ccaacagggg aaaactatat ccacagaatc    1080
ggtcgaggtg gacggttcgg ccgtaaaggt gtgactatta acatggtgac agaagaagac    1140
aagaggactc ttcgagacat tgagaccttt tacaacacct ccattgagga aatgcccctc    1200
aatgttgctg acctcatctg a                                              1221

<210> SEQ ID NO 12
<211> LENGTH: 406
<212> TYPE: PRT
<213> ORGANISM: Pan troglodytes

<400> SEQUENCE: 12

Met Ser Ala Ser Gln Asp Ser Arg Ser Arg Asp Asn Gly Pro Asp Gly
1               5                   10                  15

Met Glu Pro Glu Gly Val Ile Glu Ser Asn Trp Asn Glu Ile Val Asp
            20                  25                  30

Ser Phe Asp Asp Met Asn Leu Ser Glu Ser Leu Leu Arg Gly Ile Tyr
```

```
                35                  40                  45
Ala Tyr Gly Phe Glu Lys Pro Ser Ala Ile Gln Gln Arg Ala Ile Leu
 50                  55                  60

Pro Cys Ile Lys Gly Tyr Asp Val Ile Ala Gln Ala Gln Ser Gly Thr
 65                  70                  75                  80

Gly Lys Thr Ala Thr Phe Ala Ile Ser Ile Leu Gln Gln Ile Glu Leu
                 85                  90                  95

Asp Leu Lys Ala Thr Gln Ala Leu Val Leu Ala Pro Thr Arg Glu Leu
                100                 105                 110

Ala Gln Gln Ile Gln Lys Val Val Met Ala Leu Gly Asp Tyr Met Gly
                115                 120                 125

Ala Ser Cys His Ala Cys Ile Gly Gly Thr Asn Val Arg Ala Glu Val
         130                 135                 140

Gln Lys Leu Gln Met Glu Ala Pro His Ile Ile Val Gly Thr Pro Gly
145                 150                 155                 160

Arg Val Phe Asp Met Leu Asn Arg Arg Tyr Leu Ser Pro Lys Tyr Ile
                165                 170                 175

Lys Met Phe Val Leu Asp Glu Ala Asp Glu Met Leu Ser Arg Gly Phe
                180                 185                 190

Lys Asp Gln Ile Tyr Asp Ile Phe Gln Lys Leu Asn Ser Asn Thr Gln
                195                 200                 205

Val Val Leu Leu Ser Ala Thr Met Pro Ser Asp Val Leu Glu Val Thr
210                 215                 220

Lys Lys Phe Met Arg Asp Pro Ile Arg Ile Leu Val Lys Lys Glu Glu
225                 230                 235                 240

Leu Thr Leu Glu Gly Ile Arg Gln Phe Tyr Ile Asn Val Glu Arg Glu
                245                 250                 255

Glu Trp Lys Leu Asp Thr Leu Cys Asp Leu Tyr Glu Thr Leu Thr Ile
                260                 265                 270

Thr Gln Ala Val Ile Phe Ile Asn Thr Arg Arg Lys Val Asp Trp Leu
         275                 280                 285

Thr Glu Lys Met His Ala Arg Asp Phe Thr Val Ser Ala Met His Gly
290                 295                 300

Asp Met Asp Gln Lys Glu Arg Asp Val Ile Met Arg Glu Phe Arg Ser
305                 310                 315                 320

Gly Ser Ser Arg Val Leu Ile Thr Thr Asp Leu Leu Ala Arg Gly Ile
                325                 330                 335

Asp Val Gln Gln Val Ser Leu Val Ile Asn Tyr Asp Leu Pro Thr Asn
                340                 345                 350

Arg Glu Asn Tyr Ile His Arg Ile Gly Arg Gly Gly Arg Phe Gly Arg
                355                 360                 365

Lys Gly Val Thr Ile Asn Met Val Thr Glu Glu Asp Lys Arg Thr Leu
         370                 375                 380

Arg Asp Ile Glu Thr Phe Tyr Asn Thr Ser Ile Glu Glu Met Pro Leu
385                 390                 395                 400

Asn Val Ala Asp Leu Ile
                405

<210> SEQ ID NO 13
<211> LENGTH: 1221
<212> TYPE: DNA
<213> ORGANISM: Macaca mulatta

<400> SEQUENCE: 13
```

```
atgtctgcga gccaggattc ccgatccaga gacaatggcc ccgatggaat ggagcccgaa    60
ggcgtcatcg agagtaactg gaatgagatt gttgacagct tgatgacat gaacctctca    120
gagtctcttc tccgtggcat ctacgcctat ggttttgaga agccgtctgc catccagcag    180
cgagccattc taccttgtat caagggttac gatgtgatcg ctcaagccca atctgggact    240
gggaaaacgg ccacatttgc catatcaatt ctgcagcaga tcgaattaga tctaaaagcc    300
acccaggcct tggtcctggc acccactcga gaattggctc agcagataca gaaggtggtc    360
atggcactag gagactacat gggtgcctcc tgtcatgcct gtattggggg caccaacgtg    420
cgtgctgagg tgcagaaact gcagatggaa gccccccaca taatcatggg gacccctggc    480
cgagtgtttg atatgcttaa ccggagatac ctgtctccca aatacatcaa gatgtttgta    540
ctggacgaag ctgatgaaat gttaagccgt ggattcaagg accagatcta tgacatattc    600
caaaagctca acagcaacac ccaggtagtt ttgctgtcag ctacaatgcc ttctgatgtg    660
cttgaggtga ccaagaagtt catgagggac cccattcgga ttcttgtcaa gaaggaagag    720
ttgaccctgg agggtatctg ccaattctac atcaacgtgg aacgagagga gtggaagctg    780
gacacactat gtgacttgta tgaaacgctg accatcaccc aggcagtcat cttcatcaac    840
acccagagga aggtggactg gctcaccgag aagatgcatg ctcgagattt cactgtctct    900
gccatgcatg gagatatgga ccaaaaggaa cgagacgtga tcatgaggga gtttcgttct    960
ggctctagca gagttttgat taccactgac ctgctggcca gaggcattga tgtgcagcag    1020
gtttctttag tcatcaacta tgaccttccc ccaacaggg aaaactatat ccacagaatc    1080
ggtcgaggtg gacggtttgg ccgtaaaggt gtggctatta acatggtgac agaagaagac    1140
aagaggactc ttcgagacat cgagaccttc tataacacct ccattgagga aatgcccctc    1200
aatgttgccg acctcatctg a                                              1221
```

<210> SEQ ID NO 14
<211> LENGTH: 406
<212> TYPE: PRT
<213> ORGANISM: Macaca mulatta

<400> SEQUENCE: 14

```
Met Ser Ala Ser Gln Asp Ser Arg Ser Arg Asp Asn Gly Pro Asp Gly
1               5                   10                  15

Met Glu Pro Glu Gly Val Ile Glu Ser Asn Trp Asn Glu Ile Val Asp
            20                  25                  30

Ser Phe Asp Asp Met Asn Leu Ser Glu Ser Leu Leu Arg Gly Ile Tyr
        35                  40                  45

Ala Tyr Gly Phe Glu Lys Pro Ser Ala Ile Gln Gln Arg Ala Ile Leu
    50                  55                  60

Pro Cys Ile Lys Gly Tyr Asp Val Ile Ala Gln Ala Gln Ser Gly Thr
65                  70                  75                  80

Gly Lys Thr Ala Thr Phe Ala Ile Ser Ile Leu Gln Gln Ile Glu Leu
                85                  90                  95

Asp Leu Lys Ala Thr Gln Ala Leu Val Leu Ala Pro Thr Arg Glu Leu
            100                 105                 110

Ala Gln Gln Ile Gln Lys Val Val Met Ala Leu Gly Asp Tyr Met Gly
        115                 120                 125

Ala Ser Cys His Ala Cys Ile Gly Gly Thr Asn Val Arg Ala Glu Val
    130                 135                 140

Gln Lys Leu Gln Met Glu Ala Pro His Ile Ile Met Gly Thr Pro Gly
145                 150                 155                 160
```

```
Arg Val Phe Asp Met Leu Asn Arg Arg Tyr Leu Ser Pro Lys Tyr Ile
                165                 170                 175
Lys Met Phe Val Leu Asp Glu Ala Asp Glu Met Leu Ser Arg Gly Phe
            180                 185                 190
Lys Asp Gln Ile Tyr Asp Ile Phe Gln Lys Leu Asn Ser Asn Thr Gln
        195                 200                 205
Val Val Leu Leu Ser Ala Thr Met Pro Ser Asp Val Leu Glu Val Thr
    210                 215                 220
Lys Lys Phe Met Arg Asp Pro Ile Arg Ile Leu Val Lys Lys Glu Glu
225                 230                 235                 240
Leu Thr Leu Glu Gly Ile Cys Gln Phe Tyr Ile Asn Val Glu Arg Glu
                245                 250                 255
Glu Trp Lys Leu Asp Thr Leu Cys Asp Leu Tyr Glu Thr Leu Thr Ile
            260                 265                 270
Thr Gln Ala Val Ile Phe Ile Asn Thr Gln Arg Lys Val Asp Trp Leu
        275                 280                 285
Thr Glu Lys Met His Ala Arg Asp Phe Thr Val Ser Ala Met His Gly
    290                 295                 300
Asp Met Asp Gln Lys Glu Arg Asp Val Ile Met Arg Glu Phe Arg Ser
305                 310                 315                 320
Gly Ser Ser Arg Val Leu Ile Thr Thr Asp Leu Leu Ala Arg Gly Ile
                325                 330                 335
Asp Val Gln Gln Val Ser Leu Val Ile Asn Tyr Asp Leu Pro Thr Asn
        340                 345                 350
Arg Glu Asn Tyr Ile His Arg Ile Gly Arg Gly Arg Phe Gly Arg
    355                 360                 365
Lys Gly Val Ala Ile Asn Met Val Thr Glu Glu Asp Lys Arg Thr Leu
370                 375                 380
Arg Asp Ile Glu Thr Phe Tyr Asn Thr Ser Ile Glu Glu Met Pro Leu
385                 390                 395                 400
Asn Val Ala Asp Leu Ile
                405

<210> SEQ ID NO 15
<211> LENGTH: 1221
<212> TYPE: DNA
<213> ORGANISM: Canis familiaris

<400> SEQUENCE: 15
atgtctgcga gtcaggattc ccgatccaga gacaatggcc ccgatgggat ggagcccgaa      60
ggcgtcatcg agagtaactg gaatgagatt gttgacagct tgatgacat gaacctctcc     120 gagtcccttc tccgtggcat ctatgcttat ggtttcgaga agccttctgc catccagcag     180
cgagccattc ttccttgtat caagggttat gatgtgatcg ctcaagccca atctgggact     240
gggaaaacag ccactttttgc catatcgatt ctgcaacaaa ttgaattgga tctaaaggct     300
acacaggcct tggtcctggc acccactagg gagttggctc agcagataca gaaggtagtc     360
atggcattag agattacat gggtgcttcc tgccatgcct gcattggggg gaccaatgta      420
cgtgctgagg tgcagaagct tcagatggag gctcctcata tcatcgtggg caccccgggt     480
cgtgtgtttg acatgctgaa ccggagatac ctatctccca atatatcaa gatgtttgta     540 ctggacgaag ctgatgagat gttaagccgt ggattcaagg accagatcta tgacatattc     600
caaaagctca acagcaacac ccaggtggtt ttgctgtctg ccacgatgcc ttctgacgtg     660
```

```
cttgaggtga ccaagaagtt catgagggac cccattcgga ttctggtcaa gaaagaagag      720
ttgaccctcg agggcatccg ccagttctac atcaacgtgg agcgagagga gtggaagctg      780
gacacgctgt gtgacttgta cgagactctg accatcacac aggcagtcat tttcatcaac      840
acccgaagga aggtggattg gctcaccgag aagatgcacg cccgagactt caccgtgtct      900
gccatgcacg gagacatgga ccagaaggag cgagatgtta tcatgaggga gttccgctcg      960
ggctctagca gagtactgat taccactgac ttgctggcca gaggcatcga tgtgcagcag     1020
gtgtctctag tcatcaacta tgaccttcct accaacaggg aaaactatat ccacagaatc     1080
ggccgtggtg gacgatttgg ccggaagggt gtggctatta acatggtgac agaagaagac     1140
aagaggactc ttcgagacat cgagactttc tacaacacct ccattgagga aatgcccctc     1200
aatgttgctg acctcatctg a                                               1221
```

<210> SEQ ID NO 16
<211> LENGTH: 406
<212> TYPE: PRT
<213> ORGANISM: Canis familiaris

<400> SEQUENCE: 16

```
Met Ser Ala Ser Gln Asp Ser Arg Ser Arg Asp Asn Gly Pro Asp Gly
1               5                   10                  15

Met Glu Pro Glu Gly Val Ile Glu Ser Asn Trp Asn Glu Ile Val Asp
            20                  25                  30

Ser Phe Asp Asp Met Asn Leu Ser Glu Ser Leu Leu Arg Gly Ile Tyr
        35                  40                  45

Ala Tyr Gly Phe Glu Lys Pro Ser Ala Ile Gln Gln Arg Ala Ile Leu
    50                  55                  60

Pro Cys Ile Lys Gly Tyr Asp Val Ile Ala Gln Ala Gln Ser Gly Thr
65                  70                  75                  80

Gly Lys Thr Ala Thr Phe Ala Ile Ser Ile Leu Gln Gln Ile Glu Leu
                85                  90                  95

Asp Leu Lys Ala Thr Gln Ala Leu Val Leu Ala Pro Thr Arg Glu Leu
            100                 105                 110

Ala Gln Gln Ile Gln Lys Val Val Met Ala Leu Gly Asp Tyr Met Gly
        115                 120                 125

Ala Ser Cys His Ala Cys Ile Gly Gly Thr Asn Val Arg Ala Glu Val
    130                 135                 140

Gln Lys Leu Gln Met Glu Ala Pro His Ile Ile Val Gly Thr Pro Gly
145                 150                 155                 160

Arg Val Phe Asp Met Leu Asn Arg Arg Tyr Leu Ser Pro Lys Tyr Ile
                165                 170                 175

Lys Met Phe Val Leu Asp Glu Ala Asp Glu Met Leu Ser Arg Gly Phe
            180                 185                 190

Lys Asp Gln Ile Tyr Asp Ile Phe Gln Lys Leu Asn Ser Asn Thr Gln
        195                 200                 205

Val Val Leu Leu Ser Ala Thr Met Pro Ser Asp Val Leu Glu Val Thr
    210                 215                 220

Lys Lys Phe Met Arg Asp Pro Ile Arg Ile Leu Val Lys Lys Glu Glu
225                 230                 235                 240

Leu Thr Leu Glu Gly Ile Arg Gln Phe Tyr Ile Asn Val Glu Arg Glu
                245                 250                 255

Glu Trp Lys Leu Asp Thr Leu Cys Asp Leu Tyr Glu Thr Leu Thr Ile
            260                 265                 270
```

Thr Gln Ala Val Ile Phe Ile Asn Thr Arg Arg Lys Val Asp Trp Leu
                275                 280                 285

Thr Glu Lys Met His Ala Arg Asp Phe Thr Val Ser Ala Met His Gly
        290                 295                 300

Asp Met Asp Gln Lys Glu Arg Asp Val Ile Met Arg Glu Phe Arg Ser
305                 310                 315                 320

Gly Ser Ser Arg Val Leu Ile Thr Thr Asp Leu Leu Ala Arg Gly Ile
                325                 330                 335

Asp Val Gln Gln Val Ser Leu Val Ile Asn Tyr Asp Leu Pro Thr Asn
                340                 345                 350

Arg Glu Asn Tyr Ile His Arg Ile Gly Arg Gly Gly Arg Phe Gly Arg
                355                 360                 365

Lys Gly Val Ala Ile Asn Met Val Thr Glu Glu Asp Lys Arg Thr Leu
                370                 375                 380

Arg Asp Ile Glu Thr Phe Tyr Asn Thr Ser Ile Glu Glu Met Pro Leu
385                 390                 395                 400

Asn Val Ala Asp Leu Ile
            405

<210> SEQ ID NO 17
<211> LENGTH: 1221
<212> TYPE: DNA
<213> ORGANISM: Bos taurus

<400> SEQUENCE: 17

```
atgtctgcga gtcaggattc ccgatctaga gacaatggcc ccgatgggat ggaacccgaa      60
ggcgtcatcg agagtaactg gaatgagatt gtcgacagct tgatgacat gaacctctca      120
gagtcactcc tccgtggcat atatgcctat ggttttgaga agccctctgc cattcagcag      180
cgagccattc ttccttgtat caagggttat gatgtgattg ctcaagccca atctgggact      240
gggaaaacgg ccacttttgc catatcaatt ctgcaacaga ttgaattaga tctaaaggcc      300
acccaggcct tggtcctggc acccactaga gagttggccc agcagataca gaaggtagta      360
atggccttag agattacatg ggtgcctcg tgccatgcct gcattggggg taccaatgta      420
cgtgctgagg tgcagaagct gcagatggaa gccccccata tcatcgtggg taccccaggc      480
cgtgtgttcg acatgcttaa ccggagatac ttgtctccca aatacatcaa gatgtttgta      540
ctggatgaag ctgatgaaat gttaagccgt ggattcaagg accagatcta tgacatattc      600
cagaagctca acagcaacac ccaggtggtt ttgctgtcag ctacaatgcc ttctgatgtg      660
cttgaggtga ccaagaagtt catgagggac ccaattagaa ttcttgtcaa gaaggaagag      720
ttgacgctgg agggtatccg tcagttctac atcaatgtgg aacgagagga gtggaagctg      780
gacacactgt gcgacttgta tgaaaccctg accattaccc aggcagtcat cttcatcaac      840
acccgaagga aggtggattg gctcaccgag aagatgcatg cccgagactt caccgtctct      900
gccatgcacg gagacatgga ccaaaaagaa cgagacgtta tcatgaggga gttccgctct      960
ggctctagca gagtattgat taccactgac ctactggcca gaggtattga tgtacagcaa     1020
gtttccttag tcatcaacta tgacctcccc accaataggg aaaactatat ccacagaatt     1080
ggtcgtggcg gacgtttcgg ccgtaagggt gtggctatta acatggtgac agaagaggac     1140
aagaggactc ttcgagacat cgaaaccttc tacaacacct ccattgagga aatgcccctc     1200
aatgttgctg acctcatctg a                                              1221
```

<210> SEQ ID NO 18

```
<211> LENGTH: 406
<212> TYPE: PRT
<213> ORGANISM: Bos taurus

<400> SEQUENCE: 18

Met Ser Ala Ser Gln Asp Ser Arg Ser Arg Asp Asn Gly Pro Asp Gly
1               5                   10                  15

Met Glu Pro Glu Gly Val Ile Glu Ser Asn Trp Asn Glu Ile Val Asp
            20                  25                  30

Ser Phe Asp Asp Met Asn Leu Ser Glu Ser Leu Leu Arg Gly Ile Tyr
        35                  40                  45

Ala Tyr Gly Phe Glu Lys Pro Ser Ala Ile Gln Gln Arg Ala Ile Leu
    50                  55                  60

Pro Cys Ile Lys Gly Tyr Asp Val Ile Ala Gln Ala Gln Ser Gly Thr
65                  70                  75                  80

Gly Lys Thr Ala Thr Phe Ala Ile Ser Ile Leu Gln Gln Ile Glu Leu
                85                  90                  95

Asp Leu Lys Ala Thr Gln Ala Leu Val Leu Ala Pro Thr Arg Glu Leu
            100                 105                 110

Ala Gln Gln Ile Gln Lys Val Val Met Ala Leu Gly Asp Tyr Met Gly
        115                 120                 125

Ala Ser Cys His Ala Cys Ile Gly Gly Thr Asn Val Arg Ala Glu Val
    130                 135                 140

Gln Lys Leu Gln Met Glu Ala Pro His Ile Ile Val Gly Thr Pro Gly
145                 150                 155                 160

Arg Val Phe Asp Met Leu Asn Arg Arg Tyr Leu Ser Pro Lys Tyr Ile
                165                 170                 175

Lys Met Phe Val Leu Asp Glu Ala Asp Glu Met Leu Ser Arg Gly Phe
            180                 185                 190

Lys Asp Gln Ile Tyr Asp Ile Phe Gln Lys Leu Asn Ser Asn Thr Gln
        195                 200                 205

Val Val Leu Leu Ser Ala Thr Met Pro Ser Asp Val Leu Glu Val Thr
    210                 215                 220

Lys Lys Phe Met Arg Asp Pro Ile Arg Ile Leu Val Lys Lys Glu Glu
225                 230                 235                 240

Leu Thr Leu Glu Gly Ile Arg Gln Phe Tyr Ile Asn Val Glu Arg Glu
                245                 250                 255

Glu Trp Lys Leu Asp Thr Leu Cys Asp Leu Tyr Glu Thr Leu Thr Ile
            260                 265                 270

Thr Gln Ala Val Ile Phe Ile Asn Thr Arg Arg Lys Val Asp Trp Leu
        275                 280                 285

Thr Glu Lys Met His Ala Arg Asp Phe Thr Val Ser Ala Met His Gly
    290                 295                 300

Asp Met Asp Gln Lys Glu Arg Asp Val Ile Met Arg Glu Phe Arg Ser
305                 310                 315                 320

Gly Ser Ser Arg Val Leu Ile Thr Thr Asp Leu Leu Ala Arg Gly Ile
                325                 330                 335

Asp Val Gln Gln Val Ser Leu Val Ile Asn Tyr Asp Leu Pro Thr Asn
            340                 345                 350

Arg Glu Asn Tyr Ile His Arg Ile Gly Arg Gly Arg Phe Gly Arg
        355                 360                 365

Lys Gly Val Ala Ile Asn Met Val Thr Glu Glu Asp Lys Arg Thr Leu
    370                 375                 380

Arg Asp Ile Glu Thr Phe Tyr Asn Thr Ser Ile Glu Glu Met Pro Leu
```

Asn Val Ala Asp Leu Ile
                405

<210> SEQ ID NO 19
<211> LENGTH: 1221
<212> TYPE: DNA
<213> ORGANISM: Rattus norvegicus

<400> SEQUENCE: 19

```
atgtctgcga gtcaggattc tcgatccaga gacaatgggcc ccgatgggat ggagccggaa    60
ggcgtcatcg agagtaactg gaatgagatt gtggatagct tcgatgacat gaatctctca   120
gaatccctcc tccgtggtat ttatgcctat ggttttgaga agccctctgc catccagcag   180
cgagctattc ttccttgtat caagggttat gatgtgattg ctcaagccca gtctgggact   240
gggaaaacag ctacatttgc catatccatt ctgcagcaga ttgaattaga tctaaaggcc   300
actcaggctt tggttctggc acccactcgt gaattggctc agcagattca aaaggtggtt   360
atggcactgg gagactacat gggtgcctct tgtcatgcct gtattggggg caccaacgtg   420
cgtgctgagg tgcagaagct gcaaatggaa gctccccata tcatcgtggg cacccctggc   480
cgggtgttcg atatgcttaa ccggagatac ctgtcaccca atacatcaa gatgttcgtc    540
ctggatgaag cagatgaaat gctaagccgt gggttcaagg atcagatcta tgatatattc   600
caaaagctca cagcaacac acaggtagtt ttgctgtctg ccacaatgcc ttctgatgtc    660
cttgaggtga ctaagaagtt catgagagac cctattcgga ttcttgtcaa gaaggaagag   720
ttgaccctgg agggtatccg ccaattctac atcaatgtgg aacgagagga gtggaagctc   780
gacacattgt gtgacttgta tgaaacactg accatcaccc caggcagtaa tctttattaa    840
accagaagga aggtggactg gctcactgag aagatgcatg cccgggattt cacagtttct   900
gccatgcatg gagatatgga ccaaaaggaa cgagacgtga tcatgaggga gttccggtct   960
ggctctagca gagtattaat taccactgac ctgttggcca gaggcattga tgtgcagcag  1020
gtctccctag tcatcaatta tgaccttccc ccaacagggg aaaactacat ccacagaatt  1080
ggtcgaggtg gtcggtttgg ccggaaaggt gtggctatta acatggtgac agaagaagac  1140
aagaggactc ttcgagacat tgagactttc tacaacacct ccattgaaga gatgccctc   1200
aacgttgctg acctcatttg a                                           1221
```

<210> SEQ ID NO 20
<211> LENGTH: 406
<212> TYPE: PRT
<213> ORGANISM: Rattus norvegicus

<400> SEQUENCE: 20

Met Ser Ala Ser Gln Asp Ser Arg Ser Arg Asp Asn Gly Pro Asp Gly
1               5                   10                  15

Met Glu Pro Glu Gly Val Ile Glu Ser Asn Trp Asn Glu Ile Val Asp
            20                  25                  30

Ser Phe Asp Asp Met Asn Leu Ser Glu Ser Leu Leu Arg Gly Ile Tyr
        35                  40                  45

Ala Tyr Gly Phe Glu Lys Pro Ser Ala Ile Gln Gln Arg Ala Ile Leu
    50                  55                  60

Pro Cys Ile Lys Gly Tyr Asp Val Ile Ala Gln Ala Gln Ser Gly Thr
65                  70                  75                  80

Gly Lys Thr Ala Thr Phe Ala Ile Ser Ile Leu Gln Gln Ile Glu Leu

```
                          85                  90                  95
Asp Leu Lys Ala Thr Gln Ala Leu Val Leu Ala Pro Thr Arg Glu Leu
                100                 105                 110

Ala Gln Gln Ile Gln Lys Val Val Met Ala Leu Gly Asp Tyr Met Gly
            115                 120                 125

Ala Ser Cys His Ala Cys Ile Gly Gly Thr Asn Val Arg Ala Glu Val
        130                 135                 140

Gln Lys Leu Gln Met Glu Ala Pro His Ile Ile Val Gly Thr Pro Gly
145                 150                 155                 160

Arg Val Phe Asp Met Leu Asn Arg Arg Tyr Leu Ser Pro Lys Tyr Ile
                165                 170                 175

Lys Met Phe Val Leu Asp Glu Ala Asp Glu Met Leu Ser Arg Gly Phe
            180                 185                 190

Lys Asp Gln Ile Tyr Asp Ile Phe Gln Lys Leu Asn Ser Asn Thr Gln
        195                 200                 205

Val Val Leu Leu Ser Ala Thr Met Pro Ser Asp Val Leu Glu Val Thr
210                 215                 220

Lys Lys Phe Met Arg Asp Pro Ile Arg Ile Leu Val Lys Lys Glu Glu
225                 230                 235                 240

Leu Thr Leu Glu Gly Ile Arg Gln Phe Tyr Ile Asn Val Glu Arg Glu
                245                 250                 255

Glu Trp Lys Leu Asp Thr Leu Cys Asp Leu Tyr Glu Thr Leu Thr Ile
            260                 265                 270

Thr Gln Ala Val Ile Phe Ile Asn Thr Arg Arg Lys Val Asp Trp Leu
        275                 280                 285

Thr Glu Lys Met His Ala Arg Asp Phe Thr Val Ser Ala Met His Gly
290                 295                 300

Asp Met Asp Gln Lys Glu Arg Asp Val Ile Met Arg Glu Phe Arg Ser
305                 310                 315                 320

Gly Ser Ser Arg Val Leu Ile Thr Thr Asp Leu Leu Ala Arg Gly Ile
                325                 330                 335

Asp Val Gln Gln Val Ser Leu Val Ile Asn Tyr Asp Leu Pro Thr Asn
            340                 345                 350

Arg Glu Asn Tyr Ile His Arg Ile Gly Arg Gly Gly Arg Phe Gly Arg
        355                 360                 365

Lys Gly Val Ala Ile Asn Met Val Thr Glu Glu Asp Lys Arg Thr Leu
370                 375                 380

Arg Asp Ile Glu Thr Phe Tyr Asn Thr Ser Ile Glu Glu Met Pro Leu
385                 390                 395                 400

Asn Val Ala Asp Leu Ile
                405

<210> SEQ ID NO 21
<211> LENGTH: 1836
<212> TYPE: DNA
<213> ORGANISM: Homo sapiens

<400> SEQUENCE: 21
atggcggcct cagcaaaaaa gaagaataag aagggggaaga ctatctccct aacagacttt       60
ctggctgagg atgggggtac tggtggagga agcacctatg tttccaaacc agtcagctgg      120
gctgatgaaa cggatgacct ggaaggagat gtttcgacca cttggcacag taacgatgac      180
gatgtgtata gggcgcctcc aattgaccgt tccatccttc ccactgctcc acgggctgct      240
cgggaaccca atatcgaccg gagccgtctt cccaaatcgc caccctacac tgcttttcta      300
```

```
ggaaacctac cctatgatgt tacagaagag tcaattaagg aattctttcg aggattaaat      360
atcagtgcag tgcgtttacc acgtgaaccc agcaatccag agaggttgaa aggttttggt      420
tatgctgaat ttgaggacct ggattccctg ctcagtgccc tgagtctcaa tgaagagtct      480
ctaggtaaca ggagaattcg agtggacgtt gctgatcaag cacaggataa agacagggat      540
gatcgttctt ttggccgtga tagaaatcgg gattctgaca aaacagatac agactggagg      600
gctcgtcctg ctacagacag ctttgatgac tacccaccta agagaggtga tgatagcttt      660
ggagacaagt atcgagatcg ttatgattca gaccggtatc gggatgggta tcgggatggg      720
tatcgggatg gcccacgccg ggatatggat cgatatggtg gccgggatcg ctatgatgac      780
cgaggcagca gagactatga tagaggctat gattcccgga taggcagtgg cagaagagca      840
tttggcagtg ggtatcgcag ggatgatgac tacagaggag gcggggaccg ctatgaagac      900
cgatatgaca gacgggatga tcggtcgtgg agctccagag atgattactc tcgggatgat      960
tataggcgtg atgatagagg tcccccccaa agacccaaac tgaatctaaa gcctcggagt     1020
actcctaagg aagatgattc ctctgctagt acctcccagt ccactcgagc tgcttctatc     1080
tttggagggg caaagcctgt tgacacagct gctagagaaa gagaagtaga agaacggcta     1140
cagaaggaac aagagaagtt gcagcgtcag ctggatgagc aaaactaga acgacggcct     1200 cgggagagac acccaagctg gcgaagtgaa gaaactcagg aacgggaacg gtcgaggaca     1260
ggaagtgagt catcacaaac tgggacctcc accacatcta gcagaaatgc acgaaggaga     1320
gagagtgaga agtctctaga aaatgaaaca ctcaataagg aggaagattg ccactctcca     1380
acttctaaac ctcccaaacc tgatcagccc ctaaaggtaa tgccagcccc tccaccaaag     1440
gagaatgctt gggtgaagcg aagttctaac cctcctgctc gatctcagag ctcagacaca     1500
gagcagcagt cccctacaag tggtggggga aaagtagctc cagctcaacc atctgaggaa     1560
ggaccaggaa ggaaagatga aaataaagta gatgggatga atgccccaaa aggccaaact     1620
gggaactcta gccgtggtcc aggagacgga gggaacagag accactggaa ggagtcagat     1680
aggaaagatg gcaaaaagga tcaagactcc agatctgcac ctgagccaaa gaaacctgag     1740
gaaaatccag cttccaagtt cagttctgca agcaagtatg ctgctctctc tgttgatggt     1800
gaagatgaaa atgagggaga agattatgcc gaatag                               1836
```

<210> SEQ ID NO 22
<211> LENGTH: 611
<212> TYPE: PRT
<213> ORGANISM: Homo sapiens

<400> SEQUENCE: 22

```
Met Ala Ala Ser Ala Lys Lys Lys Asn Lys Lys Gly Lys Thr Ile Ser
1               5                   10                  15

Leu Thr Asp Phe Leu Ala Glu Asp Gly Gly Thr Gly Gly Gly Ser Thr
                20                  25                  30

Tyr Val Ser Lys Pro Val Ser Trp Ala Asp Glu Thr Asp Asp Leu Glu
            35                  40                  45

Gly Asp Val Ser Thr Thr Trp His Ser Asn Asp Asp Val Tyr Arg
        50                  55                  60

Ala Pro Pro Ile Asp Arg Ser Ile Leu Pro Thr Ala Pro Arg Ala Ala
65                  70                  75                  80

Arg Glu Pro Asn Ile Asp Arg Ser Arg Leu Pro Lys Ser Pro Pro Tyr
                85                  90                  95
```

```
Thr Ala Phe Leu Gly Asn Leu Pro Tyr Asp Val Thr Glu Ser Ile
            100                 105                 110

Lys Glu Phe Phe Arg Gly Leu Asn Ile Ser Ala Val Arg Leu Pro Arg
        115                 120                 125

Glu Pro Ser Asn Pro Glu Arg Leu Lys Gly Phe Gly Tyr Ala Glu Phe
    130                 135                 140

Glu Asp Leu Asp Ser Leu Leu Ser Ala Leu Ser Leu Asn Glu Glu Ser
145                 150                 155                 160

Leu Gly Asn Arg Arg Ile Arg Val Asp Val Ala Asp Gln Ala Gln Asp
                165                 170                 175

Lys Asp Arg Asp Arg Ser Phe Gly Arg Asp Arg Asn Arg Asp Ser
        180                 185                 190

Asp Lys Thr Asp Thr Asp Trp Arg Ala Arg Pro Ala Thr Asp Ser Phe
        195                 200                 205

Asp Asp Tyr Pro Pro Arg Arg Gly Asp Asp Ser Phe Gly Asp Lys Tyr
    210                 215                 220

Arg Asp Arg Tyr Asp Ser Asp Arg Tyr Arg Asp Gly Tyr Arg Asp Gly
225                 230                 235                 240

Tyr Arg Asp Gly Pro Arg Arg Asp Met Asp Arg Tyr Gly Gly Arg Asp
                245                 250                 255

Arg Tyr Asp Asp Arg Gly Ser Arg Asp Tyr Asp Arg Gly Tyr Asp Ser
                260                 265                 270

Arg Ile Gly Ser Gly Arg Arg Ala Phe Gly Ser Gly Tyr Arg Arg Asp
        275                 280                 285

Asp Asp Tyr Arg Gly Gly Gly Asp Arg Tyr Glu Asp Arg Tyr Asp Arg
    290                 295                 300

Arg Asp Asp Arg Ser Trp Ser Ser Arg Asp Asp Tyr Ser Arg Asp Asp
305                 310                 315                 320

Tyr Arg Arg Asp Asp Arg Gly Pro Pro Gln Arg Pro Lys Leu Asn Leu
                325                 330                 335

Lys Pro Arg Ser Thr Pro Lys Glu Asp Asp Ser Ser Ala Ser Thr Ser
        340                 345                 350

Gln Ser Thr Arg Ala Ala Ser Ile Phe Gly Gly Ala Lys Pro Val Asp
    355                 360                 365

Thr Ala Ala Arg Glu Arg Glu Val Glu Glu Arg Leu Gln Lys Glu Gln
    370                 375                 380

Glu Lys Leu Gln Arg Gln Leu Asp Glu Pro Lys Leu Glu Arg Arg Pro
385                 390                 395                 400

Arg Glu Arg His Pro Ser Trp Arg Ser Glu Glu Thr Gln Glu Arg Glu
                405                 410                 415

Arg Ser Arg Thr Gly Ser Glu Ser Ser Gln Thr Gly Thr Ser Thr Thr
                420                 425                 430

Ser Ser Arg Asn Ala Arg Arg Glu Ser Glu Lys Ser Leu Glu Asn
        435                 440                 445

Glu Thr Leu Asn Lys Glu Glu Asp Cys His Ser Pro Thr Ser Lys Pro
    450                 455                 460

Pro Lys Pro Asp Gln Pro Leu Lys Val Met Pro Ala Pro Pro Lys
465                 470                 475                 480

Glu Asn Ala Trp Val Lys Arg Ser Ser Asn Pro Ala Arg Ser Gln
                485                 490                 495

Ser Ser Asp Thr Glu Gln Gln Ser Pro Thr Ser Gly Gly Lys Val
        500                 505                 510

Ala Pro Ala Gln Pro Ser Glu Glu Gly Pro Gly Arg Lys Asp Glu Asn
```

|     | 515 |     |     |     | 520 |     |     |     | 525 |     |     |
| --- | --- | --- | --- | --- | --- | --- | --- | --- | --- | --- | --- |

Lys Val Asp Gly Met Asn Ala Pro Lys Gly Gln Thr Gly Asn Ser Ser
530                     535                     540

Arg Gly Pro Gly Asp Gly Asn Arg Asp His Trp Lys Glu Ser Asp
545                 550                     555                     560

Arg Lys Asp Gly Lys Asp Gln Asp Ser Arg Ser Ala Pro Glu Pro
                565                     570                     575

Lys Lys Pro Glu Glu Asn Pro Ala Ser Lys Phe Ser Ser Ala Ser Lys
            580                     585                     590

Tyr Ala Ala Leu Ser Val Asp Gly Glu Asp Glu Asn Glu Gly Glu Asp
                595                     600                     605

Tyr Ala Glu
610

<210> SEQ ID NO 23
<211> LENGTH: 1836
<212> TYPE: DNA
<213> ORGANISM: Mus musculus

<400> SEQUENCE: 23

| | | | | | |
|---|---|---|---|---|---|
| atggcggcct | cagcaaaaaa | gaagaataag | aaggggaaga | ccatctccct | aacggacttt | 60 |
| ctagctgagg | atggaggaac | tggtggagga | agcacctatg | tccccaaacc | agtcagctgg | 120 |
| gctgatgaaa | cagacgatct | ggaaggagat | gtgtcaacaa | cttggcatag | taacgatgat | 180 |
| gacgtgtaca | gggcgcctcc | aattgaccgt | tccatccttc | ccactgctcc | acgggctgct | 240 |
| cgggaaccca | atattgaccg | gagccgtctt | cccaagtcgc | cacctacac | tgctttccta | 300 |
| gggaatctgc | cctatgatgt | gacagaagac | tccattaagg | atttctttag | aggattaaat | 360 |
| atcagcgctg | tacgcttacc | acgggaaccc | agcaatccag | acaggttgaa | aggtttcggc | 420 |
| tacgcagaat | ttgaggacct | ggattctctg | ctcagtgctc | tgagtctcaa | tgaagagtct | 480 |
| ctaggtaaca | ggagaattcg | tgtggatgtt | gctgatcaag | cacaggataa | agacagggat | 540 |
| gaccgttctt | ttggtcgaga | tagaaatcgg | gattctgaca | aaacagacac | agactggagg | 600 |
| gcccgtccca | ccacagacag | ttttgatgac | tacccaccta | agagaggcga | tgatagcttt | 660 |
| ggagacaagt | atcgagatcg | ttacgattca | gaccggtatc | gggatgggta | tagggacgga | 720 |
| tatcgggacg | gccacgcag | agacatggac | cgctatgggg | gccgggatcg | ctatgatgac | 780 |
| cgaggcagca | gagactatga | ccgaggctat | gactccagga | taggcagtgg | cagaagggca | 840 |
| tttggaagtg | ggtaccggag | agatgatgac | tacagaggag | gtgggggaccg | ctatgaagac | 900 |
| cgctatgaca | gacgggatga | tcggtcgtgg | agctccaggg | atgactactc | tcgggatgat | 960 |
| tataggcgtg | atgacagagg | tccccccag | agacccagac | tgaacctcaa | gcctcgaagc | 1020 |
| gctcctaagg | aggatgacgc | ctccgccagc | acctcccagt | ccagccgggc | agcctccatc | 1080 |
| tttgagggg | cgaagcctgt | tgacacagct | gctagggaaa | gagaagtaga | ggagcggcta | 1140 |
| cagaaggagc | aggagaagct | gcagcgtcag | ctggatgagc | aaaactaga | ccgccggccc | 1200 |
| cgggagagac | acccaagctg | gcgaagtgaa | gaaactcagg | aaagagaacg | gtcaaggaca | 1260 |
| ggaagtgagt | catcgcagac | tggggcctca | gccacatctg | gcagaaatac | acgaaggaga | 1320 |
| gagagtgaga | agtctctaga | aaatgaaacc | ctcaataaag | aagaagactg | tcactctcca | 1380 |
| acctctaagc | tcctaaaacc | tgaccagcct | ctaaaggtaa | tgccagcccc | tccaccaaag | 1440 |
| gagaatgcgt | gggtgaagcg | aagctctaac | cctcctgccc | gatctcagag | ctcagacaca | 1500 |
| gagcagccgt | cccctacaag | tggtggaggg | aaagtagctg | cagtccagcc | ccctgaggaa | 1560 |

```
ggaccatcaa gaaaagatgg aaataaagtg gatgtggtgg gtgccacaca aggccaagct    1620
ggaagctgca gccgtggtcc cggggatgga gggagcagag accactggaa ggacttggat    1680
aggaaggatg gcaaaaaaga tcaagactcc agatctgcgc ctgagccaaa gaaacctgag    1740
gagaacccag cctctaagtt cagctctgca agcaagtacg ctgctctgtc tgtggatggc    1800
gaggatgagg atgagggcga cgactgcact gagtag                              1836
```

```
<210> SEQ ID NO 24
<211> LENGTH: 611
<212> TYPE: PRT
<213> ORGANISM: Mus musculus

<400> SEQUENCE: 24
```

```
Met Ala Ala Ser Ala Lys Lys Asn Lys Lys Gly Lys Thr Ile Ser
1               5                   10                  15

Leu Thr Asp Phe Leu Ala Glu Asp Gly Thr Gly Gly Gly Ser Thr
                20                  25                  30

Tyr Val Pro Lys Pro Val Ser Trp Ala Asp Glu Thr Asp Asp Leu Glu
                35                  40                  45

Gly Asp Val Ser Thr Thr Trp His Ser Asn Asp Asp Val Tyr Arg
    50                  55                  60

Ala Pro Pro Ile Asp Arg Ser Ile Leu Pro Thr Ala Pro Arg Ala Ala
65                  70                  75                  80

Arg Glu Pro Asn Ile Asp Arg Ser Arg Leu Pro Lys Ser Pro Pro Tyr
                85                  90                  95

Thr Ala Phe Leu Gly Asn Leu Pro Tyr Asp Val Thr Glu Asp Ser Ile
                100                 105                 110

Lys Asp Phe Phe Arg Gly Leu Asn Ile Ser Ala Val Arg Leu Pro Arg
                115                 120                 125

Glu Pro Ser Asn Pro Asp Arg Leu Lys Gly Phe Gly Tyr Ala Glu Phe
                130                 135                 140

Glu Asp Leu Asp Ser Leu Leu Ser Ala Leu Ser Leu Asn Glu Glu Ser
145                 150                 155                 160

Leu Gly Asn Arg Arg Ile Arg Val Asp Val Ala Asp Gln Ala Gln Asp
                165                 170                 175

Lys Asp Arg Asp Arg Ser Phe Gly Arg Asp Arg Asn Arg Asp Ser
                180                 185                 190

Asp Lys Thr Asp Thr Asp Trp Arg Ala Arg Pro Thr Thr Asp Ser Phe
                195                 200                 205

Asp Asp Tyr Pro Pro Arg Arg Gly Asp Asp Ser Phe Gly Asp Lys Tyr
                210                 215                 220

Arg Asp Arg Tyr Asp Ser Asp Arg Tyr Arg Asp Gly Tyr Arg Asp Gly
225                 230                 235                 240

Tyr Arg Asp Gly Pro Arg Arg Asp Met Asp Arg Tyr Gly Gly Arg Asp
                245                 250                 255

Arg Tyr Asp Asp Arg Gly Ser Arg Asp Tyr Asp Arg Gly Tyr Asp Ser
                260                 265                 270

Arg Ile Gly Ser Gly Arg Arg Ala Phe Gly Ser Gly Tyr Arg Arg Asp
                275                 280                 285

Asp Asp Tyr Arg Gly Gly Gly Asp Arg Tyr Glu Asp Arg Tyr Asp Arg
                290                 295                 300

Arg Asp Asp Arg Ser Trp Ser Ser Arg Asp Asp Tyr Ser Arg Asp Asp
305                 310                 315                 320
```

Tyr Arg Arg Asp Asp Arg Gly Pro Pro Gln Arg Pro Arg Leu Asn Leu
                325                 330                 335

Lys Pro Arg Ser Ala Pro Lys Glu Asp Ala Ser Ala Ser Thr Ser
            340                 345                 350

Gln Ser Ser Arg Ala Ala Ser Ile Phe Gly Gly Ala Lys Pro Val Asp
            355                 360                 365

Thr Ala Ala Arg Glu Arg Glu Val Glu Glu Arg Leu Gln Lys Glu Gln
            370                 375                 380

Glu Lys Leu Gln Arg Gln Leu Asp Glu Pro Lys Leu Asp Arg Arg Pro
385                 390                 395                 400

Arg Glu Arg His Pro Ser Trp Arg Ser Glu Glu Thr Gln Glu Arg Glu
                405                 410                 415

Arg Ser Arg Thr Gly Ser Glu Ser Ser Gln Thr Gly Ala Ser Ala Thr
            420                 425                 430

Ser Gly Arg Asn Thr Arg Arg Glu Ser Glu Lys Ser Leu Glu Asn
            435                 440                 445

Glu Thr Leu Asn Lys Glu Asp Cys His Ser Pro Thr Ser Lys Pro
    450                 455                 460

Pro Lys Pro Asp Gln Pro Leu Lys Val Met Pro Ala Pro Pro Lys
465                 470                 475                 480

Glu Asn Ala Trp Val Lys Arg Ser Ser Asn Pro Pro Ala Arg Ser Gln
                485                 490                 495

Ser Ser Asp Thr Glu Gln Pro Ser Pro Thr Ser Gly Gly Lys Val
            500                 505                 510

Ala Ala Val Gln Pro Pro Glu Glu Gly Pro Ser Arg Lys Asp Gly Asn
            515                 520                 525

Lys Val Asp Val Val Gly Ala Thr Gln Gly Gln Ala Gly Ser Cys Ser
    530                 535                 540

Arg Gly Pro Gly Asp Gly Gly Ser Arg Asp His Trp Lys Asp Leu Asp
545                 550                 555                 560

Arg Lys Asp Gly Lys Lys Asp Gln Asp Ser Arg Ser Ala Pro Glu Pro
                565                 570                 575

Lys Lys Pro Glu Glu Asn Pro Ala Ser Lys Phe Ser Ser Ala Ser Lys
            580                 585                 590

Tyr Ala Ala Leu Ser Val Asp Gly Glu Asp Glu Asp Glu Gly Asp Asp
            595                 600                 605

Cys Thr Glu
    610

<210> SEQ ID NO 25
<211> LENGTH: 2090
<212> TYPE: DNA
<213> ORGANISM: Macaca mulatta

<400> SEQUENCE: 25
ctctcccaac atggcggcct cagcaaaaaa gaagaataag aaggggaaga ctatctccct    60
aacagacttt ctggctgagg atgggggtac tggtggagga agcacctatg tttccaaacc   120
agtcagctgg gctgatgaaa cggatgacct ggaaggagat gtttcaacaa cgtggcacag   180
taatgacgac gatgtgtaca gggcgcctcc aattgaccgt tccatccttc ccactgctcc   240
acgggctgct cgggaaccca atatcgaccg gagccgtctt cccaaatcgc accctacac   300 tgcttttcta gggaacctac cctatgatgt gacagaagaa tcaattaagg aattctttag   360
aggattaaat atcagtgcag tgcgtttacc acgtgaaccc agcaatccag agaggttgaa   420

|  |  |
|---|---|
| aggtttggt tatgctgaat ttgaggacct ggattccctg ctcagtgccc tgagtctcaa | 480 |
| tgaagagtct ctaggtaaca ggagaattcg agtggacgtt gctgatcaag cacaggataa | 540 |
| agacagggat gatcgttctt ttggccgtga tagaaatcgg gattctgaca aaacagatac | 600 |
| agactggagg gctcgtcctg ctacagacag ctttgatgac tacccaccta aagaggtga | 660 |
| tgatagcttt ggagacaagt atcgagatcg ttatgattca gaccggtatc gggatgggta | 720 |
| tcgggatggc ccacgccggg atatggatcg atatggtggc cgggatcgct atgatgaccg | 780 |
| aggcagcaga gactatgata gaggctatga ttcccggata ggcagtggca gaagagcatt | 840 |
| tggcagtggg tatcgcaggg atgatgacta cagaggaggc ggggaccgat atgaagaccg | 900 |
| atacgacaga cgggatgatc ggtcgtggag ctccagagat gattactctc gggatgatta | 960 |
| taggcgcgat gacagaggtc cccctcaaag acccaaactg aatctaaagc ctcggagtac | 1020 |
| tcctaaggaa gatgattcct ctgctagtac ctcccagtcc agtcgagctg cttctatctt | 1080 |
| tggaggggca aagcctgttg acacagctgc tagagaaaga gaagtagaag aacggctaca | 1140 |
| gaaggaacaa gagaagttgc agcgtcagct ggatgagcca aaactagaac gacggcctcg | 1200 |
| ggagagacac ccaagctggc gaagtgaaga aactcaggaa cgggaacggt cgaggacagg | 1260 |
| aagtgagtca tcacagactg ggacctccgc cacatctggc agaaatgcac gaaggagaga | 1320 |
| gagtgagaag tctctagaaa atgaaacact caataaggag gaagattgtc actctccaac | 1380 |
| ttctaaacct cccaaacctg atcagcccct aaaggtaatg ccagcccctc caccaaagga | 1440 |
| gaatgcttgg gtgaagcgaa gttctaaccc tccagctcga tctcagagct cagacacaga | 1500 |
| gcagcaatcc cctacaagtg gtggggaaa agtagctcca gctcaaccat ctgaggaagg | 1560 |
| accagcaagg aaagatgaaa ataaagtaga tgggatgaat gtcccaaaag gccaaactgg | 1620 |
| gacctctagc cgtggaccag gagacggagg gaacaaagac cactggaagg agtcagatag | 1680 |
| gaaagatggc aaaaaggatc aagactccag atctgcacct gagccaaaga aacctgagga | 1740 |
| aaatccagct tcgaagttca gttctgcaag caagtatgct gctctctctg ttgatggtga | 1800 |
| agatgaaaac gagggagaag attatgccga atagacctct acatcctgtg ctttctccta | 1860 |
| gtttctctcc accctggaac attcgagagc aaatcaaaac ctctatccag acaagacaaa | 1920 |
| ataaaactca ccatctcctg aagacctttc ttacctttt ttaaaaacaa aaatgaaat | 1980 |
| tattttgcat gctgctgcag cctttaaagt attaaagtaa ctggagaatc gccaatatag | 2040 |
| ccagagagaa agggactaca gctttttaga ggaagagttg tggtgtgtta | 2090 |

<210> SEQ ID NO 26
<211> LENGTH: 607
<212> TYPE: PRT
<213> ORGANISM: Macaca mulatta

<400> SEQUENCE: 26

Met Ala Ala Ser Ala Lys Lys Asn Lys Lys Gly Lys Thr Ile Ser
1               5                   10                  15

Leu Thr Asp Phe Leu Ala Glu Asp Gly Gly Thr Gly Gly Gly Ser Thr
                20                  25                  30

Tyr Val Ser Lys Pro Val Ser Trp Ala Asp Glu Thr Asp Asp Leu Glu
            35                  40                  45

Gly Asp Val Ser Thr Thr Trp His Ser Asn Asp Asp Val Tyr Arg
        50                  55                  60

Ala Pro Pro Ile Asp Arg Ser Ile Leu Pro Thr Ala Pro Arg Ala Ala
65                  70                  75                  80

Arg Glu Pro Asn Ile Asp Arg Ser Arg Leu Pro Lys Ser Pro Pro Tyr
                    85                  90                  95

Thr Ala Phe Leu Gly Asn Leu Pro Tyr Asp Val Thr Glu Glu Ser Ile
            100                 105                 110

Lys Glu Phe Phe Arg Gly Leu Asn Ile Ser Ala Val Arg Leu Pro Arg
            115                 120                 125

Glu Pro Ser Asn Pro Glu Arg Leu Lys Gly Phe Gly Tyr Ala Glu Phe
            130                 135                 140

Glu Asp Leu Asp Ser Leu Leu Ser Ala Leu Ser Leu Asn Glu Glu Ser
145                 150                 155                 160

Leu Gly Asn Arg Arg Ile Arg Val Asp Val Ala Asp Gln Ala Gln Asp
                165                 170                 175

Lys Asp Arg Asp Asp Arg Ser Phe Gly Arg Asp Arg Asn Arg Asp Ser
            180                 185                 190

Asp Lys Thr Asp Thr Asp Trp Arg Ala Arg Pro Ala Thr Asp Ser Phe
            195                 200                 205

Asp Asp Tyr Pro Pro Arg Arg Gly Asp Asp Ser Phe Gly Asp Lys Tyr
            210                 215                 220

Arg Asp Arg Tyr Asp Ser Asp Arg Tyr Arg Asp Gly Tyr Arg Asp Gly
225                 230                 235                 240

Pro Arg Arg Asp Met Asp Arg Tyr Gly Gly Arg Asp Arg Tyr Asp Asp
                245                 250                 255

Arg Gly Ser Arg Asp Tyr Asp Arg Gly Tyr Asp Ser Arg Ile Gly Ser
                260                 265                 270

Gly Arg Arg Ala Phe Gly Ser Gly Tyr Arg Arg Asp Asp Asp Tyr Arg
                275                 280                 285

Gly Gly Gly Asp Arg Tyr Glu Asp Arg Tyr Asp Arg Arg Asp Asp Arg
            290                 295                 300

Ser Trp Ser Ser Arg Asp Asp Tyr Ser Arg Asp Asp Tyr Arg Arg Asp
305                 310                 315                 320

Asp Arg Gly Pro Pro Gln Arg Pro Lys Leu Asn Leu Lys Pro Arg Ser
                325                 330                 335

Thr Pro Lys Glu Asp Asp Ser Ser Ala Ser Thr Ser Gln Ser Ser Arg
            340                 345                 350

Ala Ala Ser Ile Phe Gly Gly Ala Lys Pro Val Asp Thr Ala Ala Arg
            355                 360                 365

Glu Arg Glu Val Glu Glu Arg Leu Gln Lys Glu Gln Glu Lys Leu Gln
            370                 375                 380

Arg Gln Leu Asp Glu Pro Lys Leu Glu Arg Arg Pro Arg Glu Arg His
385                 390                 395                 400

Pro Ser Trp Arg Ser Glu Glu Thr Gln Glu Arg Glu Arg Ser Arg Thr
                405                 410                 415

Gly Ser Glu Ser Ser Gln Thr Gly Thr Ser Ala Thr Ser Gly Arg Asn
            420                 425                 430

Ala Arg Arg Arg Glu Ser Glu Lys Ser Leu Glu Asn Glu Thr Leu Asn
                435                 440                 445

Lys Glu Glu Asp Cys His Ser Pro Thr Ser Lys Pro Pro Lys Pro Asp
            450                 455                 460

Gln Pro Leu Lys Val Met Pro Ala Pro Pro Lys Glu Asn Ala Trp
465                 470                 475                 480

Val Lys Arg Ser Ser Asn Pro Pro Ala Arg Ser Gln Ser Ser Asp Thr
                485                 490                 495

Glu Gln Gln Ser Pro Thr Ser Gly Gly Gly Lys Val Ala Pro Ala Gln

```
                500             505             510
Pro Ser Glu Glu Gly Pro Ala Arg Lys Asp Glu Asn Lys Val Asp Gly
        515                 520                 525

Met Asn Val Pro Lys Gly Gln Thr Gly Thr Ser Ser Arg Gly Pro Gly
    530                 535                 540

Asp Gly Gly Asn Lys Asp His Trp Lys Glu Ser Asp Arg Lys Asp Gly
545                 550                 555                 560

Lys Lys Asp Gln Asp Ser Arg Ser Ala Pro Glu Pro Lys Lys Pro Glu
                565                 570                 575

Glu Asn Pro Ala Ser Lys Phe Ser Ser Ala Ser Lys Tyr Ala Ala Leu
            580                 585                 590

Ser Val Asp Gly Glu Asp Glu Asn Glu Gly Glu Asp Tyr Ala Glu
            595                 600                 605

<210> SEQ ID NO 27
<211> LENGTH: 1833
<212> TYPE: DNA
<213> ORGANISM: Bos taurus

<400> SEQUENCE: 27
```

| | | | | | |
|---|---|---|---|---|---|
| atggcggcct | cagcgaaaaa | gaagaataag | aaggggaaga | ctatctccct | aacagacttt | 60 |
| ctggctgagg | atggagggac | tggtggaggc | agcacctatg | tccccaaacc | agtcagctgg | 120 |
| gctgatgaaa | cagacgatct | ggaagggat | gtttcaacca | cttggcatag | taatgatgat | 180 |
| gatgtgtatc | gggcacctcc | aattgaccgt | tccatcctgc | ccactgctcc | acgggctgct | 240 |
| cgggaaccca | atatcgaccg | gagccgtctt | cccaaatctc | cacccacac | tgcttttcta | 300 |
| gggaacctgc | cctatgatgt | gacagaagac | tccattaagg | aattctttag | aggattaaat | 360 |
| atcagtgcag | tgcgtttacc | gcgtgaaccc | agcaatcctg | agaggttaaa | aggttttggt | 420 |
| tatgcagagt | ttgaggacct | ggattccttg | ctcagtgcct | tgagcctcaa | cgaagagtct | 480 |
| ctaggtaaca | ggagaattcg | agtggacgtt | gctgatcaag | cacaggataa | agacagggat | 540 |
| gatcgttctt | ttggccgaga | tagaaatcgt | gattctgaca | aaacagatac | agactggagg | 600 |
| gcccgtcctg | ctgcagacag | ctttgatgac | taccgcccca | aaggggtga | tgatagcttt | 660 |
| ggagacaagt | atcgagatcg | ttacgattca | gacagatatc | gtgatgggta | tcggacagt | 720 |
| taccgtgatg | gcccacgccg | ggacatggat | cgatacgggg | gccgagatcg | ctatgatgac | 780 |
| cgaggtggca | gagactatga | cagaggctac | gattccagga | taggcagtgg | cagaagagca | 840 |
| ttcggtagcg | ggtaccggag | ggatgatgac | tacagaggag | gcgggaccg | ctatgaagac | 900 |
| agatacgaca | gacgagatga | ccggtcctgg | agttccagag | atgattactc | tcgggatgat | 960 |
| tacaggcggg | atgatagagg | tcccccctcaa | agacccaaac | tgaacctaaa | gcctcggagt | 1020 |
| actcctaagg | aagatgattc | ctccgctagc | acctcccagt | ccagtcgtgc | agcctctatc | 1080 |
| tttggagggg | caaagcctgt | tgacacagct | gctagagaac | gagaagtaga | gagcggcta | 1140 |
| cagaaggaac | aggagaaact | gcagcgtcag | ctggatgagc | aaaactaga | acgacggcct | 1200 |
| cgggagagac | acccaagctg | gcgaagtgaa | gaaactcagg | aacgggaacg | atcgaggaca | 1260 |
| ggaagtgagt | catcacagac | tgggacctca | gccacatctg | gcagaaatgc | aagaagaaga | 1320 |
| gagagtgaga | agtcttaga | aaatgaaacc | cccaataaag | aggaagactg | tcagtctcca | 1380 |
| acttctaagc | ctcccaaacc | tgaacagcct | ctaaaggtaa | tgccagcccc | tccaccaaag | 1440 |
| gagaatgctt | gggtgaagcg | aagttctaac | cctcctgctc | gatctcagag | ctcagacaca | 1500 |
| gagcagcagt | cccctacaag | tggtggaggg | aaagtagttc | cagctcaact | atctgaggaa | 1560 |

-continued

```
ggatcagcaa ggaaagatga aaataaagta gatggggtga gtgccccaaa aggccaaagt    1620
gggagctcca gccgtggtcc gggagatggg gggaacaaag accactggaa ggaggcagac    1680
aggaaagatg gcaaaaagga tcacgactcc agatctgcac ctgagccaaa gaaagctgaa    1740
gaaaatccag cctcgaagtt cagatctgca agcaagtacg ctactctcgc cattgacggt    1800
gaagatgaaa atgagggaga ttacaccgaa tag                                  1833
```

<210> SEQ ID NO 28
<211> LENGTH: 610
<212> TYPE: PRT
<213> ORGANISM: Bos taurus

<400> SEQUENCE: 28

```
Met Ala Ala Ser Ala Lys Lys Asn Lys Lys Gly Lys Thr Ile Ser
1               5                   10                  15

Leu Thr Asp Phe Leu Ala Glu Asp Gly Thr Gly Gly Gly Ser Thr
                20                  25                  30

Tyr Val Pro Lys Pro Val Ser Trp Ala Asp Glu Thr Asp Asp Leu Glu
                35                  40                  45

Gly Asp Val Ser Thr Thr Trp His Ser Asn Asp Asp Val Tyr Arg
    50                  55                  60

Ala Pro Pro Ile Asp Arg Ser Ile Leu Pro Thr Ala Pro Arg Ala Ala
65                  70                  75                  80

Arg Glu Pro Asn Ile Asp Arg Ser Arg Leu Pro Lys Ser Pro Pro Tyr
                85                  90                  95

Thr Ala Phe Leu Gly Asn Leu Pro Tyr Asp Val Thr Glu Asp Ser Ile
                100                 105                 110

Lys Glu Phe Phe Arg Gly Leu Asn Ile Ser Ala Val Arg Leu Pro Arg
                115                 120                 125

Glu Pro Ser Asn Pro Glu Arg Leu Lys Gly Phe Gly Tyr Ala Glu Phe
            130                 135                 140

Glu Asp Leu Asp Ser Leu Leu Ser Ala Leu Ser Leu Asn Glu Glu Ser
145                 150                 155                 160

Leu Gly Asn Arg Arg Ile Arg Val Asp Val Ala Asp Gln Ala Gln Asp
                165                 170                 175

Lys Asp Arg Asp Asp Arg Ser Phe Gly Arg Asp Arg Asn Arg Asp Ser
            180                 185                 190

Asp Lys Thr Asp Thr Asp Trp Arg Ala Arg Pro Ala Ala Asp Ser Phe
        195                 200                 205

Asp Asp Tyr Pro Pro Arg Arg Gly Asp Asp Ser Phe Gly Asp Lys Tyr
    210                 215                 220

Arg Asp Arg Tyr Asp Ser Asp Arg Tyr Arg Asp Gly Tyr Arg Asp Ser
225                 230                 235                 240

Tyr Arg Asp Gly Pro Arg Arg Asp Met Asp Arg Tyr Gly Gly Arg Asp
                245                 250                 255

Arg Tyr Asp Asp Arg Gly Gly Arg Asp Tyr Asp Arg Gly Tyr Asp Ser
            260                 265                 270

Arg Ile Gly Ser Gly Arg Arg Ala Phe Gly Ser Gly Tyr Arg Arg Asp
        275                 280                 285

Asp Asp Tyr Arg Gly Gly Gly Asp Arg Tyr Glu Asp Arg Tyr Asp Arg
    290                 295                 300

Arg Asp Asp Arg Ser Trp Ser Ser Arg Asp Asp Tyr Ser Arg Asp Asp
305                 310                 315                 320
```

Tyr Arg Arg Asp Asp Arg Gly Pro Pro Gln Arg Pro Lys Leu Asn Leu
             325                 330                 335

Lys Pro Arg Ser Thr Pro Lys Glu Asp Asp Ser Ser Ala Ser Thr Ser
         340                 345                 350

Gln Ser Ser Arg Ala Ala Ser Ile Phe Gly Gly Ala Lys Pro Val Asp
     355                 360                 365

Thr Ala Ala Arg Glu Arg Glu Val Glu Glu Arg Leu Gln Lys Glu Gln
 370                 375                 380

Glu Lys Leu Gln Arg Gln Leu Asp Glu Pro Lys Leu Glu Arg Arg Pro
385                 390                 395                 400

Arg Glu Arg His Pro Ser Trp Arg Ser Glu Glu Thr Gln Glu Arg Glu
             405                 410                 415

Arg Ser Arg Thr Gly Ser Glu Ser Ser Gln Thr Gly Thr Ser Ala Thr
         420                 425                 430

Ser Gly Arg Asn Ala Arg Arg Glu Ser Glu Lys Ser Leu Glu Asn
     435                 440                 445

Glu Thr Pro Asn Lys Glu Asp Cys Gln Ser Pro Thr Ser Lys Pro
 450                 455                 460

Pro Lys Pro Glu Gln Pro Leu Lys Val Met Pro Ala Pro Pro Lys
465                 470                 475                 480

Glu Asn Ala Trp Val Lys Arg Ser Ser Asn Pro Pro Ala Arg Ser Gln
             485                 490                 495

Ser Ser Asp Thr Glu Gln Gln Ser Pro Thr Ser Gly Gly Gly Lys Val
         500                 505                 510

Val Pro Ala Gln Leu Ser Glu Glu Gly Ser Ala Arg Lys Asp Glu Asn
     515                 520                 525

Lys Val Asp Gly Val Ser Ala Pro Lys Gly Gln Ser Gly Ser Ser Ser
 530                 535                 540

Arg Gly Pro Gly Asp Gly Gly Asn Lys Asp His Trp Lys Glu Ala Asp
545                 550                 555                 560

Arg Lys Asp Gly Lys Lys Asp His Asp Ser Arg Ser Ala Pro Glu Pro
             565                 570                 575

Lys Lys Ala Glu Glu Asn Pro Ala Ser Lys Phe Arg Ser Ala Ser Lys
         580                 585                 590

Tyr Ala Thr Leu Ala Ile Asp Gly Glu Asp Glu Asn Glu Gly Asp Tyr
     595                 600                 605

Thr Glu
    610

<210> SEQ ID NO 29
<211> LENGTH: 1836
<212> TYPE: DNA
<213> ORGANISM: Rattus norvegicus

<400> SEQUENCE: 29
atggcggcct cagcaaaaaa gaagaataag aagggaaga ccatctccct aacagacttt      60
ctagctgagg atgggggaac tggtggagga agcacctatg tccccaaacc agtcagctgg    120
gctgatgaaa cagacgatct ggaaggagat gtgtcaacaa cttggcatag taacgatgac    180
gatgtgtaca gggcacctcc tattgaccgt tccatccttc ccactgctcc acgggctgct    240
cgggaaccca atattgatcg gagccgtctt cccaagtcac caccctacac tgctttccta    300
gggaatctgc cctatgatgt gacagaagac tctattaagg atttctttag aggattaaat    360
atcagcgctg tacgcttgcc gcgtgagccc agcaatccag acaggttgaa aggttttggc    420

| | | |
|---|---|---|
| tatgccgaat tgaggatct ggattctctg ctcagtgctc tgagtctcaa tgaagagtct | 480 | |
| ctaggtaaca ggagaattcg ggtggatgtt gctgatcaag cacaggataa agacagggat | 540 | |
| gaccgttctt ttggtcgaga tagaaatcgg gattctgaca agacagacac agactggagg | 600 | |
| gcccgtcctg ccacagacag ctttgatgac tacccaccta gacgaggtga tgacagcttc | 660 | |
| ggagacaagt atcgagatcg ttacgagtca gaccggtatc gggatgggta tagggacgga | 720 | |
| tatcgggacg gccacgcag agacatggac cgctatgggg gccgggatcg ctatgatgac | 780 | |
| cgaggcagca gagactatga ccgaggctat gactccagga taggcagtgg cagaagagca | 840 | |
| tttggaagtg ggtaccggag ggatgacgac tacagaggag gtggggaccg ctatgaagat | 900 | |
| cgctatgaca gacgggacga tcggtcatgg agctccaggg acgattactc tcgggacgat | 960 | |
| tacaggcgtg atgacagagg tccccccaa agacccaaac tgaatctaaa gcctcggagt | 1020 | |
| actcctaaag aagatgattc ctctgctagc acctcccagt ccagccgagc ggcttctatc | 1080 | |
| tttgagggg cgaagcctgt tgacacagct gctagagaaa gagaagtaga ggagcggcta | 1140 | |
| cagaaggagc aggagaagct gcagcgtcag ctggatgagc aaaactaga ccgccggccc | 1200 | |
| cgggagagac acccaagttg gcgaagtgaa gaaactcagg aaagagaacg gtcgaggaca | 1260 | |
| ggaagtgagt catcgcagac tgggacctca gccacatctg gcagaaatac acgaaggaga | 1320 | |
| gagagtgaga agtctctaga aaatgaaacc ctcaataaag aagaagactg tcactctcca | 1380 | |
| acctctaagc ctcctaaacc tgaccagcct ctaaaggtaa tgccagcccc tccaccaaag | 1440 | |
| gagaatgcgt gggtgaagcg aagctctaac cctcctgctc gatctcagag ctcagacaca | 1500 | |
| gagcagccgt cccctacaag tggtggaggg aaagttgctc cagctcagcc ctctgaggaa | 1560 | |
| ggaccatcaa ggaaagatga actaaagtg gatggggtga gcaccaccaa aggccagact | 1620 | |
| ggacactcca gccgtggtcc tggggatgga gggagcagag accactggaa ggagttggat | 1680 | |
| aggaaggacg gcaaaaaaga tcaagactcc agatctgcac ctgagccaaa gaaatctgag | 1740 | |
| gagaaccgag cctctaagtt cagttctgca agcaagtacg ctgctctgtc tgtggacggt | 1800 | |
| gaggatgagg atgagggaga cgactgcact gagtag | 1836 | |

<210> SEQ ID NO 30
<211> LENGTH: 611
<212> TYPE: PRT
<213> ORGANISM: Rattus norvegicus

<400> SEQUENCE: 30

Met Ala Ala Ser Ala Lys Lys Lys Asn Lys Gly Lys Thr Ile Ser
1               5                   10                  15

Leu Thr Asp Phe Leu Ala Glu Asp Gly Gly Thr Gly Gly Ser Thr
                20                  25                  30

Tyr Val Pro Lys Pro Val Ser Trp Ala Asp Glu Thr Asp Asp Leu Glu
            35                  40                  45

Gly Asp Val Ser Thr Thr Trp His Ser Asn Asp Asp Val Tyr Arg
        50                  55                  60

Ala Pro Pro Ile Asp Arg Ser Ile Leu Pro Thr Ala Pro Arg Ala Ala
65                  70                  75                  80

Arg Glu Pro Asn Ile Asp Arg Ser Arg Leu Pro Lys Ser Pro Pro Tyr
                85                  90                  95

Thr Ala Phe Leu Gly Asn Leu Pro Tyr Asp Val Thr Glu Asp Ser Ile
            100                 105                 110

Lys Asp Phe Phe Arg Gly Leu Asn Ile Ser Ala Val Arg Leu Pro Arg
        115                 120                 125

```
Glu Pro Ser Asn Pro Asp Arg Leu Lys Gly Phe Gly Tyr Ala Glu Phe
    130                 135                 140

Glu Asp Leu Asp Ser Leu Leu Ser Ala Leu Ser Leu Asn Glu Glu Ser
145                 150                 155                 160

Leu Gly Asn Arg Arg Ile Arg Val Asp Val Ala Asp Gln Ala Gln Asp
                165                 170                 175

Lys Asp Arg Asp Asp Arg Ser Phe Gly Arg Asp Arg Asn Arg Asp Ser
            180                 185                 190

Asp Lys Thr Asp Thr Asp Trp Arg Ala Arg Pro Ala Thr Asp Ser Phe
        195                 200                 205

Asp Asp Tyr Pro Pro Arg Arg Gly Asp Asp Ser Phe Gly Asp Lys Tyr
    210                 215                 220

Arg Asp Arg Tyr Glu Ser Asp Arg Tyr Arg Asp Gly Tyr Arg Asp Gly
225                 230                 235                 240

Tyr Arg Asp Gly Pro Arg Arg Asp Met Asp Arg Tyr Gly Gly Arg Asp
                245                 250                 255

Arg Tyr Asp Asp Arg Gly Ser Arg Asp Tyr Asp Arg Gly Tyr Asp Ser
            260                 265                 270

Arg Ile Gly Ser Gly Arg Arg Ala Phe Gly Ser Gly Tyr Arg Arg Asp
        275                 280                 285

Asp Asp Tyr Arg Gly Gly Gly Asp Arg Tyr Glu Asp Arg Tyr Asp Arg
    290                 295                 300

Arg Asp Asp Arg Ser Trp Ser Ser Arg Asp Asp Tyr Ser Arg Asp Asp
305                 310                 315                 320

Tyr Arg Arg Asp Asp Arg Gly Pro Pro Gln Arg Pro Lys Leu Asn Leu
                325                 330                 335

Lys Pro Arg Ser Thr Pro Lys Glu Asp Asp Ser Ser Ala Ser Thr Ser
            340                 345                 350

Gln Ser Ser Arg Ala Ala Ser Ile Phe Gly Gly Ala Lys Pro Val Asp
        355                 360                 365

Thr Ala Ala Arg Glu Arg Glu Val Glu Glu Arg Leu Gln Lys Glu Gln
    370                 375                 380

Glu Lys Leu Gln Arg Gln Leu Asp Glu Pro Lys Leu Asp Arg Arg Pro
385                 390                 395                 400

Arg Glu Arg His Pro Ser Trp Arg Ser Glu Glu Thr Gln Glu Arg Glu
                405                 410                 415

Arg Ser Arg Thr Gly Ser Glu Ser Ser Gln Thr Gly Thr Ser Ala Thr
            420                 425                 430

Ser Gly Arg Asn Thr Arg Arg Glu Ser Glu Lys Ser Leu Glu Asn
        435                 440                 445

Glu Thr Leu Asn Lys Glu Glu Asp Cys His Ser Pro Thr Ser Lys Pro
    450                 455                 460

Pro Lys Pro Asp Gln Pro Leu Lys Val Met Pro Ala Pro Pro Lys
465                 470                 475                 480

Glu Asn Ala Trp Val Lys Arg Ser Ser Asn Pro Ala Arg Ser Gln
                485                 490                 495

Ser Ser Asp Thr Glu Gln Pro Ser Pro Thr Ser Gly Gly Lys Val
            500                 505                 510

Ala Pro Ala Gln Pro Ser Glu Glu Gly Pro Ser Arg Lys Asp Glu Thr
        515                 520                 525

Lys Val Asp Gly Val Ser Thr Thr Lys Gly Gln Thr Gly His Ser Ser
    530                 535                 540
```

```
Arg Gly Pro Gly Asp Gly Gly Ser Arg Asp His Trp Lys Glu Leu Asp
545                 550                 555                 560

Arg Lys Asp Gly Lys Lys Asp Gln Asp Ser Arg Ser Ala Pro Glu Pro
            565                 570                 575

Lys Lys Ser Glu Glu Asn Arg Ala Ser Lys Phe Ser Ser Ala Ser Lys
        580                 585                 590

Tyr Ala Ala Leu Ser Val Asp Gly Glu Asp Glu Asp Glu Gly Asp Asp
    595                 600                 605

Cys Thr Glu
    610

<210> SEQ ID NO 31
<211> LENGTH: 21
<212> TYPE: DNA
<213> ORGANISM: Artificial Sequence
<220> FEATURE:
<223> OTHER INFORMATION: /note="Description of Artificial Sequence:
      sh-eIF4A #1 shRNA target sequence"

<400> SEQUENCE: 31
gccgtgtgtt tgatatgctt a                                          21

<210> SEQ ID NO 32
<211> LENGTH: 21
<212> TYPE: DNA
<213> ORGANISM: Artificial Sequence
<220> FEATURE:
<223> OTHER INFORMATION: /note="Description of Artificial Sequence:
      sh-eIF4A #2 shRNA target sequence"

<400> SEQUENCE: 32
gccgtaaagg tgtggctatt a                                          21

<210> SEQ ID NO 33
<211> LENGTH: 21
<212> TYPE: DNA
<213> ORGANISM: Artificial Sequence
<220> FEATURE:
<223> OTHER INFORMATION: /note="Description of Artificial Sequence:
      sh-eIF4A #3 shRNA target sequence"

<400> SEQUENCE: 33
ccttgtatca agggttatga t                                          21

<210> SEQ ID NO 34
<211> LENGTH: 21
<212> TYPE: DNA
<213> ORGANISM: Artificial Sequence
<220> FEATURE:
<223> OTHER INFORMATION: /note="Description of Artificial Sequence:
      sh-eIF4A #4 shRNA target sequence"

<400> SEQUENCE: 34
cgaaatgtta agccgtggat t                                          21

<210> SEQ ID NO 35
<211> LENGTH: 21
<212> TYPE: DNA
<213> ORGANISM: Artificial Sequence
<220> FEATURE:
<223> OTHER INFORMATION: /note="Description of Artificial Sequence:
      sh-eIF4A #5 shRNA target sequence"

<400> SEQUENCE: 35
gcagcaggtt tctttagtca t                                          21
```

```
<210> SEQ ID NO 36
<211> LENGTH: 21
<212> TYPE: DNA
<213> ORGANISM: Artificial Sequence
<220> FEATURE:
<223> OTHER INFORMATION: /note="Description of Artificial Sequence:
      sh-eIF4B #1 shRNA target sequence"

<400> SEQUENCE: 36
gcggagaaac accttgatct t                                              21

<210> SEQ ID NO 37
<211> LENGTH: 21
<212> TYPE: DNA
<213> ORGANISM: Artificial Sequence
<220> FEATURE:
<223> OTHER INFORMATION: /note="Description of Artificial Sequence:
      sh-eIF4B #2 shRNA target sequence"

<400> SEQUENCE: 37
gccgtgatag aaatcgggat t                                              21

<210> SEQ ID NO 38
<211> LENGTH: 21
<212> TYPE: DNA
<213> ORGANISM: Artificial Sequence
<220> FEATURE:
<223> OTHER INFORMATION: /note="Description of Artificial Sequence:
      sh-eIF4B #3 shRNA target sequence"

<400> SEQUENCE: 38
ccaacttcta aacctcccaa a                                              21

<210> SEQ ID NO 39
<211> LENGTH: 21
<212> TYPE: DNA
<213> ORGANISM: Artificial Sequence
<220> FEATURE:
<223> OTHER INFORMATION: /note="Description of Artificial Sequence:
      sh-eIF4B #4 shRNA target sequence"

<400> SEQUENCE: 39
ctaccctatg atgttacaga a                                              21

<210> SEQ ID NO 40
<211> LENGTH: 21
<212> TYPE: DNA
<213> ORGANISM: Artificial Sequence
<220> FEATURE:
<223> OTHER INFORMATION: /note="Description of Artificial Sequence:
      sh-eIF4B #5 shRNA target sequence"

<400> SEQUENCE: 40
cgggatgatt ataggcgtga t                                              21

<210> SEQ ID NO 41
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 41
acccccgagc tgtgctgctc g                                              21
```

```
<210> SEQ ID NO 42
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 42
cgtcgcggga ggctgctggt t                                              21

<210> SEQ ID NO 43
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 43
ctaccctctc aacgacagca                                                20

<210> SEQ ID NO 44
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 44
agagcagaga atccgaggac                                                20

<210> SEQ ID NO 45
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 45
gtgctgcatg aggagacacc                                                20

<210> SEQ ID NO 46
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 46
tttgcctctt ctccacagac a                                              21
```